US011858993B2

(12) United States Patent
Cheal et al.

(10) Patent No.: US 11,858,993 B2
(45) Date of Patent: Jan. 2, 2024

(54) MULTI-SPECIFIC ANTIBODIES WITH AFFINITY FOR HUMAN A33 ANTIGEN AND DOTA METAL COMPLEX AND USES THEREOF

(71) Applicants: Memorial Sloan Kettering Cancer Center, New York, NY (US); Massachusetts Institute of Technology, Cambridge, MA (US)

(72) Inventors: Sarah Cheal, New York, NY (US); Hong Xu, New York, NY (US); Steven Larson, New York, NY (US); Nai-Kong Cheung, New York, NY (US); Karl Dane Wittrup, Cambridge, MA (US); Alice Tzeng, Beachwood, OH (US)

(73) Assignees: Memorial Sloan Kettering Cancer Center, New York, NY (US); Massachusetts Institute of Technology, Cambridge, MA (US)

( * ) Notice: Subject to any disclaimer, the term of this patent is extended or adjusted under 35 U.S.C. 154(b) by 346 days.

(21) Appl. No.: 17/229,007

(22) Filed: Apr. 13, 2021

(65) Prior Publication Data
US 2021/0301014 A1 Sep. 30, 2021

Related U.S. Application Data

(62) Division of application No. 15/549,638, filed as application No. PCT/US2016/017141 on Feb. 9, 2016, now Pat. No. 10,988,534.

(60) Provisional application No. 62/113,988, filed on Feb. 9, 2015.

(51) Int. Cl.
*A61P 35/00* (2006.01)
*A61K 51/04* (2006.01)
*A61K 39/00* (2006.01)
*C07K 16/28* (2006.01)

(52) U.S. Cl.
CPC ...... *C07K 16/2803* (2013.01); *A61K 51/0482* (2013.01); *A61P 35/00* (2018.01); *A61K 2039/505* (2013.01); *C07K 2317/24* (2013.01); *C07K 2317/31* (2013.01); *C07K 2317/622* (2013.01)

(58) Field of Classification Search
CPC ............ C07K 16/2803; C07K 2317/24; C07K 2317/31; C07K 2317/622; C07K 2317/73; C07K 2319/33; C07K 16/44; A61K 51/00; A61K 51/04; A61K 51/0482; A61K 2039/505; A61K 2039/545; A61K 39/39575; A61K 39/00; A61K 47/00; A61K 47/6879; A61K 47/6897; A61K 45/06; A61K 45/00; A61K 39/395; A61P 35/00; A61P 1/00; A61P 1/18; A61P 43/00

USPC ............................. 424/1.11, 1.65, 1.69, 1.73
See application file for complete search history.

(56) References Cited

U.S. PATENT DOCUMENTS

| | | | |
|---|---|---|---|
| 4,444,887 A | 4/1984 | Hoffmann | |
| 4,472,509 A | 9/1984 | Gansow et al. | |
| 4,716,111 A | 12/1987 | Osband et al. | |
| 4,938,948 A | 7/1990 | Ring et al. | |
| 5,021,236 A | 6/1991 | Gries et al. | |
| 5,413,823 A | 5/1995 | Lo Presti et al. | |
| 5,545,806 A | 8/1996 | Lonberg et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,641,870 A | 6/1997 | Rinderknecht et al. | |
| 5,661,016 A | 8/1997 | Lonberg et al. | |
| 5,670,356 A | 9/1997 | Sherf et al. | |
| 5,814,318 A | 9/1998 | Lonberg et al. | |
| 5,874,304 A | 2/1999 | Zolotukhin et al. | |
| 5,886,793 A | 3/1999 | Satou | |
| 5,916,771 A | 6/1999 | Hori et al. | |
| 5,939,598 A | 8/1999 | Kucherlapati et al. | |
| 6,180,370 B1 | 1/2001 | Queen et al. | |
| 6,218,149 B1 | 4/2001 | Morrison et al. | |
| 6,472,511 B1 | 10/2002 | Leung et al. | |
| 6,602,684 B1 | 8/2003 | Umana et al. | |
| 8,502,018 B2 | 8/2013 | Murphy et al. | |
| 10,988,534 B2 * | 4/2021 | Cheal ........................ | A61P 1/00 |
| 2002/0028486 A1 | 3/2002 | Morrison et al. | |
| 2003/0115614 A1 | 6/2003 | Kanda et al. | |
| 2010/0254987 A1 | 10/2010 | Davis et al. | |
| 2013/0216528 A1 | 8/2013 | Cheung et al. | |
| 2014/0105889 A1 | 4/2014 | Igawa et al. | |
| 2014/0294835 A1 | 10/2014 | Moore et al. | |

FOREIGN PATENT DOCUMENTS

| | | |
|---|---|---|
| EP | 0 239 400 | 9/1987 |
| EP | 0 359 096 A1 | 3/1990 |
| EP | 0 598 877 A1 | 12/1993 |
| EP | 2 698 431 B1 | 2/2014 |
| JP | AH11-506435 A | 6/1999 |
| JP | 2007-527391 A | 9/2007 |
| WO | WO-91/10741 A1 | 7/1991 |
| WO | WO-92/01047 A1 | 1/1992 |
| WO | WO-96/33735 A1 | 10/1996 |
| WO | WO-96/34096 A1 | 10/1996 |

(Continued)

OTHER PUBLICATIONS

U.S. Appl. No. 10/113,929.

(Continued)

*Primary Examiner* — D. L. Jones
(74) *Attorney, Agent, or Firm* — Foley & Lardner LLP

(57) ABSTRACT

Described herein are multi-specific binding agents that bind A33 and 1,4,7,10-tetraazacyclododecane-1,4,7,10-tetraacetic acid. Also provided herein are methods of using multi-specific binding agents or compositions thereof for the detection, prevention, and/or therapeutic treatment of diseases characterized by expression of the A33 glycoprotein antigen, in particular, colorectal cancer.

3 Claims, 10 Drawing Sheets
Specification includes a Sequence Listing.

(56) References Cited

FOREIGN PATENT DOCUMENTS

| | | |
|---|---|---|
| WO | WO-96/37224 A1 | 11/1996 |
| WO | WO-98/00433 | 1/1998 |
| WO | WO-98/16664 A1 | 4/1998 |
| WO | WO-98/22149 A1 | 5/1998 |
| WO | WO-98/24893 A1 | 6/1998 |
| WO | WO-98/46645 A1 | 10/1998 |
| WO | WO-00/61739 A1 | 10/2000 |
| WO | WO-02/30954 A1 | 4/2002 |
| WO | WO-03/035835 A2 | 5/2003 |
| WO | WO-2005/004809 | 1/2005 |
| WO | WO-2010/099536 A2 | 9/2010 |
| WO | WO-2012/133782 A1 | 10/2012 |
| WO | WO-2014/144763 A2 | 9/2014 |
| WO | WO-2021/133782 A1 | 7/2021 |

OTHER PUBLICATIONS

U.S. Appl. No. 10/277,370.

Cheal S.M. et al.: "Curative Multicycle Radioimmunotherapy Monitored by Quantitative SPEC/CT-Based Theranostics, Using Bispecific Antibody Pretargeting Strategy in Colorectal Cancer.", J. Nucl. Med., vol. 58, No. 11, Nov. 2017 (Nov. 2017), pp. 1735-1742, XP002781616, *the whole document*.

Cheal S.M. et al.: "Preclinical evaluation of multistep targeting of diasialoganglioside GD2 and DOTA metal complex", Mol. Cancer Ther., vol. 13, No. 7, Jun. 18, 2014 (Jun. 18, 2014), pp. 1803-1812, XP002781612, *the whole document*.

Cheal, et al., 2014, "Preclinical evaluation of multistep targeting of diasialoganglioside GD2 using an IgG-scFv bispecific antibody with high affinity for GD2 and DOTA metal complex," Mol Cancer Ther, 13(7):1803-1812.

Heal J.K. et al.: "The human A33 antigen is a transmembrane glycoprotein and a novel member of the immunoglobulin superfamily.", PNAS, vol. 94, Jan. 1997 (Jan. 1997), pp. 469-474, XP002781613, *the whole document*.

International Search Report and Written Opinion, PCT/US2016/017141, Memorial Sloan Kettering Cancer Center, 18 pages (dated Aug. 4, 2016).

King et al., "Preparation and preclinical evaluation of humanized A33 immunoconjugates for radioimmunotherapy," British Journal of Cancer, 72, pp. 1364-1372 (1995).

Orcutt, K., et al., "A modular IgG-scFv bispecific antibody topology," Protein Engineering, Design and Selection, vol. 23, No. 4, pp. 221-228 (Apr. 1, 2010).

* cited by examiner

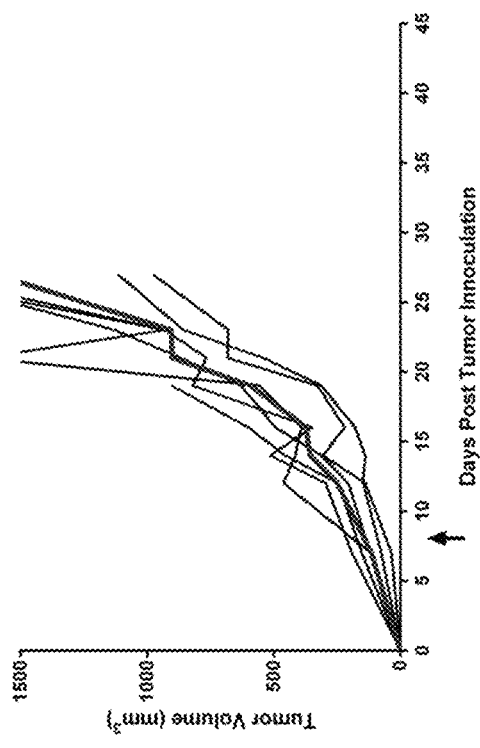
Fig. 5A
Fig. 5B
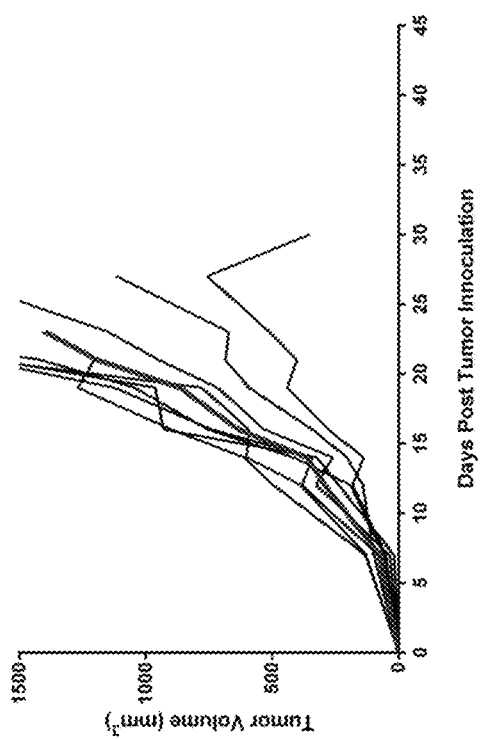
Fig. 5C
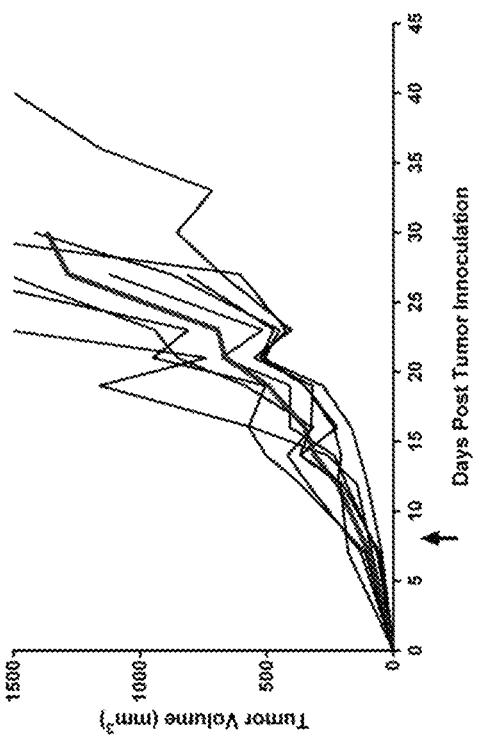
Fig. 5D

MULTI-SPECIFIC ANTIBODIES WITH AFFINITY FOR HUMAN A33 ANTIGEN AND DOTA METAL COMPLEX AND USES THEREOF

CROSS REFERENCE TO RELATED APPLICATIONS

This application is a divisional of U.S. Non-Provisional patent application Ser. No. 15/549,638, filed on Aug. 8, 2017, which is a U.S. national stage application of PCT/US2016/017141, filed Feb. 9, 2016, which claims the benefit of U.S. Provisional Application Ser. No. 62/113,988, filed on Feb. 9, 2015, the contents of which are herein incorporated by reference in their entireties.

SEQUENCE LISTING

The instant application contains a Sequence Listing which has been submitted electronically in ASCII format and is hereby incorporated by reference in its entirety. Said, ASCII copy, created on Apr. 12, 2021 is named 115872-2184 SL.txt and is 26 bytes in size.

BACKGROUND

Antibody-based therapeutics offer significant promise, particularly in the treatment of cancer. A variety of formats, including monoclonal, murine, chimeric, humanized, human, full-length, Fab, pegylated, radiolabeled, drug-conjugated, multi-specific, etc. are being developed. Of the more than 30 therapeutic antibody agents that have received marketing approval in the United States or Europe (see e.g., Reichert, mAbs 4:3, 413, May/June 2012, incorporated herein by reference), two bispecific antibodies (Catumaxomab and Blinatumomab) made using different technologies have been approved for use in humans. Still, development of particular effective antibody agents remains a challenge.

SUMMARY OF INVENTION

The present invention provides, among other things, multispecific binding agents that include binding moieties that interact with a particular target. In many embodiments, such binding moieties are or comprise antibody components. In some embodiments, multispecific binding agents of the present invention comprise binding elements of humanized antibody A33 (referred to herein as huA33). In some embodiments, multispecific binding agents of the present invention comprise a first binding moiety based on huA33 and a second binding moiety that interacts with an organic or inorganic compound. Such provided agents have improved functional characteristics as compared to parental binding agents that lack such components described herein.

In particular, the present invention provides improved multi-specific (e.g., bispecific) antibody agents that bind A33 glycoprotein and Benzyl-1,4,7,10-tetraazacyclododecane-1,4,7,10-tetraacetic acid (DOTA-Bn), wherein said multi-specific binding agents contain one or more structural features (e.g., one or more CDRs) of humanized antibody A33 and one or more structural features (e.g., one or more CDRs) of monoclonal antibody 2D12.5. In some embodiments, provided multi-specific binding agents demonstrate high tumor uptake and low toxicity to normal tissues (e.g., bone marrow and kidney) as compared to parental antibodies A33 and 2D12.5. In some embodiments, provided multispecific binding agents overcome suboptimal tumor dose and therapeutic index deficiencies when employed in a pre-targeted radioimmunotherapy approach to ameliorate A33-positive tumors.

In some embodiments, the present invention provides a bispecific antibody comprising a first antigen-binding site based on humanized antibody A33 (huA33) and a second antigen-binding site based on monoclonal antibody 2D12.5. In some embodiments, the 2D12.5 antibody is humanized.

In some embodiments, first antigen-binding sites and/or second antigen-binding sites are or comprise a polypeptide chain or chains.

In some embodiments, a polypeptide chain or chains include heavy chain CDRs found in a sequence that appears in Table 8. In some certain embodiments, heavy chain CDRs are found in humanized A33 antibody (huA33). In some embodiments, a polypeptide chain or chains include light chain CDRs found in a sequence that appears in Table 8. In some certain embodiments, light chain CDRs are found in humanized A33 antibody (huA33). In some embodiments, a polypeptide chain or chains include heavy and light chain CDRs found in one or more sequences that appears in Table 8. In some certain embodiments, heavy and light chain CDRs are found in humanized A33 antibody (huA33).

In some embodiments, first and/or second antigen-binding sites are or comprise single chain variable fragments (scFvs). In some embodiments, a first antigen-binding site is composed of an immunoglobulin molecule and the second antigen-binding site is composed of an scFv, scFab, Fab or Fv. In some embodiments, a second antigen-binding site is an scFv. In some certain embodiments, a second antigen-binding site is C825 scFv. In some embodiments, the C825 scFv is humanized. In some embodiments, an scFv is linked to the C-terminal end of the heavy chain of the immunoglobulin molecule. In some embodiments, an scFv is linked to the C-terminal end of the light chain of the immunoglobulin molecule.

In some embodiments, the present invention provides a bispecific antibody comprised of an immunoglobulin molecule based on humanized antibody A33 (huA33), and an scFv that binds benzyl-1,4,7,10-tetraazacyclododecane-1,4,7,10-tetraacetic acid (DOTA-Bn), wherein the scFv is based on C825 and is linked to the C-terminal end of the light chain of huA33 and the bispecific antibody is characterized by limited immunological impact when administered to an organism.

In some embodiments, an immunoglobulin molecule is an IgG. In some embodiments, an immunoglobulin molecule is an aglycosylated IgG. In some embodiments, an immunoglobulin molecule is an IgG having a K322A substitution. In some embodiments, an immunoglobulin molecule is an aglycosylated IgG having a K322 substitution.

In various embodiments, a bispecific antibody of the present invention comprises SEQ ID NO:2, SEQ ID NO:3 or SEQ ID NO: 4. In various embodiments, a bispecific antibody of the present invention comprises SEQ ID NO:6 or SEQ ID NO: 7. In various embodiments, a bispecific antibody of the present invention comprises SEQ ID NO:2, SEQ ID NO:3 or SEQ ID NO: 4 and further comprises SEQ ID NO:6 or SEQ ID NO: 7.

In various embodiments, a bispecific antibody of the present invention comprises SEQ ID NO:2 and SEQ ID NO:6, SEQ ID NO:2 and SEQ ID NO:7, SEQ ID NO:3 and SEQ ID NO:6, SEQ ID NO:3 and SEQ ID NO:7, SEQ ID NO:4 and SEQ ID NO:6, or SEQ ID NO:4 and SEQ ID NO:7.

In some embodiments, the present invention provides an isolated nucleic acid molecule comprising a coding sequence for part or all of a polypeptide chain of a bispecific antibody as described herein. In some certain embodiments, the coding sequence is codon-optimized.

In some embodiments, the present invention provides an expression vector comprising a nucleic acid molecule as described herein.

In some embodiments, the present invention provides a host cell comprising a host cell as described herein.

In some embodiments, the present invention provides a method of producing a bispecific antibody as described herein, the method comprising the steps of culturing a host cell as described herein in a culture medium under conditions allowing the expression of the bispecific antibody, and separating the bispecific antibody from the culture medium.

In some embodiments, the present invention provides a composition comprising a bispecific antibody as described herein.

In some embodiments, the present invention provides a pharmaceutical composition comprising a composition as described herein or a bispecific antibody as described herein.

In some embodiments, the present invention provides use of a pharmaceutical composition as described herein or a composition as described herein for the treatment or diagnosis of cancer.

In some embodiments, the present invention provides use of a bispecific antibody, composition or pharmaceutical composition as described herein for the treatment or detection of a condition related to A33 expression.

In some embodiments, the present invention provides a kit comprising a bispecific antibody described herein.

In some embodiments, the present invention provides use of a bispecific antibody described herein in the manufacture of a medicament for use in medicine.

In some embodiments, the present invention provides use of a bispecific antibody described herein in the manufacture of a medicament for use in a diagnostic test or assay.

In some embodiments, the present invention provides use of a bispecific antibody described herein in the manufacture of a medicament for the diagnosis of cancer.

In some embodiments, the present invention provides use of a bispecific antibody described herein in the manufacture of a medicament for the treatment of cancer.

In some embodiments, the present invention provides use of a bispecific antibody described herein in the manufacture of a medicament for the treatment of colorectal cancer, gastric cancer or pancreatic cancer.

In some embodiments, the present invention provides a method of treating a medical condition in a subject, wherein the medical condition is characterized by A33 expression, comprising administering a therapeutically effective amount of a bispecific antibody as described herein to said subject. In some embodiments, a medical condition includes an A33-positive tumor. In some certain embodiments, a medical condition is colorectal cancer, gastric cancer or pancreatic cancer.

In some embodiments, the present invention provides a method of killing tumor cells, the method comprising steps of contacting tumor cells with a bispecific antibody, which bispecific antibody is composed of a first antigen-binding site based on humanized antibody A33 (huA33) and a second antigen-binding site that binds benzyl-1,4,7,10-tetraazacyclododecane-1,4,7,10-tetraacetic acid (DOTA-Bn), the contacting being performed under conditions and for a time sufficient so that tumor cell killing is observed.

In some embodiments, the present invention provides a method of inhibiting tumor growth, the method comprising the steps of contacting tumor cells with a bispecific antibody, which bispecific antibody is composed of a first antigen-binding site based on humanized antibody A33 and a second antigen-binding site that binds benzyl-1,4,7,10-tetraazacyclododecane-1,4,7,10-tetraacetic acid (DOTA), the contacting being performed under conditions and for a time sufficient for the non-binding bispecific antibody to clear the blood, to permit the last step of DOTA-Bn conjugated to a poison to kill tumor cells.

In some embodiments, a step of contacting comprises administering a bispecific antibody as described herein to an organism, and the administering is performed so that unbound bispecific antibody is cleared from the blood. In some embodiments, a step of administering comprises administering a bispecific antibody as described herein in combination with a conjugate comprising DOTA-Bn conjugated to a payload, the administering being performed so that the payload is delivered to tumor cells. In some embodiments, administering is performed so that tumor cells are substantially saturated with a bispecific antibody as described herein. In some embodiments, administering is performed so that tumor cells are substantially saturated by a bispecific antibody as described herein prior to administration of a conjugate. In some embodiments, administering is performed according to a combination regimen characterized by a therapeutic index for the conjugate that is at least 10 fold better than that observed for a reference regimen in which the conjugate is administered as a single-step monotherapy.

In some embodiments, administering is by a regimen that includes one or more cycles. In some embodiments, administering is by a regimen that includes, for example, 1, 2, 3, 4, 5, 6, 7, 8, 9, 10 or more cycles.

In some embodiments, administering is by a regimen that includes one or more cycles of a first administration step in which a bispecific antibody is administered, a second administration step in which a conjugate is administered, and at least one third administration step in which the same conjugate or a different conjugate DOTA-Bn conjugated to a payload is administered. In some embodiments, a first administration step is performed so that tumor cells are substantially saturated with a bispecific antibody. In some embodiments, a first administration step is performed prior to a second administration step and to any third administration step, and no further administration of a bispecific antibody is performed within the cycle. In some certain embodiments, no cycle after a first cycle includes any administration of a bispecific antibody. In some embodiments, administering is performed over a period of hours to days.

In some embodiments, a conjugate is administered over minutes.

In some embodiments, a second antigen-binding site is based on monoclonal antibody 2D12.5. In some embodiments, the second antigen-binding site is based on humanized 2D12.5.

In some embodiments, the present invention provides a method of treating or diagnosing an A33-positive cancer in a subject, the method comprising administering a bispecific antibody described herein to a subject, the administering being performed under conditions and for a time sufficient for the bispecific antibody to localize to one or more tumors that express the A33 antigen, followed by administering a clearing agent to the subject, wherein the clearing agent removes unbound bispecific antibody, followed by administering radiolabeled DOTA-Bn to the subject. In some certain embodiments, the method further comprises administering the bispecific antibody a second time to the subject.

In some embodiments, administering the bispecific antibody a second time to the subject is performed after administering a clearing agent. In some embodiments, administering the bispecific antibody a second time to the subject is followed by administering a clearing agent a second time to the subject.

In some embodiments, a method of treating as described herein results in substantially no radiation toxicity to normal tissues. In some embodiments, a method of treating as described herein results in greater than 10-fold increase in therapeutic index. In some embodiments, a method of treating as described herein is curative.

In many embodiments, a clearing agent is a dextran-based clearing agent. In many embodiments, a radiolabeled DOTA is $^{177}$Lu-DOTA-Bn, $^{90}$Y-DOTA-Bn or $^{86}$Y-DOTA-Bn.

In some embodiments, a payload is a toxic payload. In some embodiments, a payload is a biologic response modifier. In some embodiments, a payload is selected from the group consisting of detectable moieties and active moieties. In some embodiments, a payload is or comprises a group selected from the group consisting of radioisotopes, peptides, nucleic acids, small molecules, nanoparticles, viruses, and combinations thereof.

BRIEF DESCRIPTION OF THE DRAWING

The Drawing included herein, which is composed of the following Figures, is for illustration purposes only and not for limitation.

(FIG. 4A) uptake of amounts of $^{177}$Lu-DOTA-Bn in various tissues. (FIG. 4B) Uptake of amounts of $^{177}$Lu-DOTA-Bn in SW1222 tumors; (FIG. 4C) activity of $^{177}$Lu-DOTA-Bn in SW1222 tumors and kidneys 24 hours post injection per amount of injected $^{177}$Lu-DOTA-Bn; (FIG. 4D) pmoles of $^{177}$Lu-DOTA-Bn binding in the tumor 24 hours post injection per amount of injected $^{177}$Lu-DOTA-Bn. Saturation was achieved after approximately 40 MBq of injected activity.

FIGS. 5A-5D show exemplary tumor growth measurements (mm$^3$) in groups of mice receiving single-cycle PRIT; (FIG. 5A) control (no treatment, n=8), (FIG. 5B) 0.9 mCi (33.3 MBq; 1 mCi=37 MBq)$^{177}$Lu-DOTA-Bn only (n=6); (FIG. 5C) huA33-C825+0.3 mCi $^{177}$Lu-DOTA-Bn (n=8), (FIG. 5D) huA33-C825+0.9 mCi $^{177}$Lu-DOTA-Bn (n=8). Control and treated (huA33-C825) SW1222 tumors demonstrate that the growth pattern of SW1222 tumors is only minimally affected by the radioactivity with a single dose, even with dose escalation. The highest dose (0.9 mCi) demonstrates some effect. The arrow indicates the day that $^{177}$Lu-DOTA-Bn was administered. The dose of huA33-C825 was given at t=−24 hours, followed by a dextran-clearing agent at t=−4 hours, and $^{177}$Lu-DOTA-Bn at t=0 hours.

(FIG. 6A) 2×huA33-C825 PRIT+11.1 MBq (total: 22.2 MBq), (FIG. 6B) 2×huA33-C825 PRIT+33.3 MBq (total: 66.6 MBq), (FIG. 6C) 2×huA33-C825 PRIT+55.5 MBq (total: 111 MBq), (FIG. 6D) 1x huA33-C825 PRIT+111 MBq (total: 111 MBq). For dual-cycle PRIT given at 10 and 17 days post tumor inoculation, there is marked response at all dose levels with complete responses observed in a dose dependent manner. In FIG. 6C (2×huA33-C825 PRIT+55.5 MBq (total: 111 MBq)), all the tumors have responded to treatment. Toxicity was determined by monitoring weight and overall appearance at least three times per week, as well as histopathologic assessment of liver, kidney, spleen and bone marrow by MSKCC Lab of Comparative Pathology. There was no detectable toxicity in the mice.

DEFINITIONS

Figure 1:
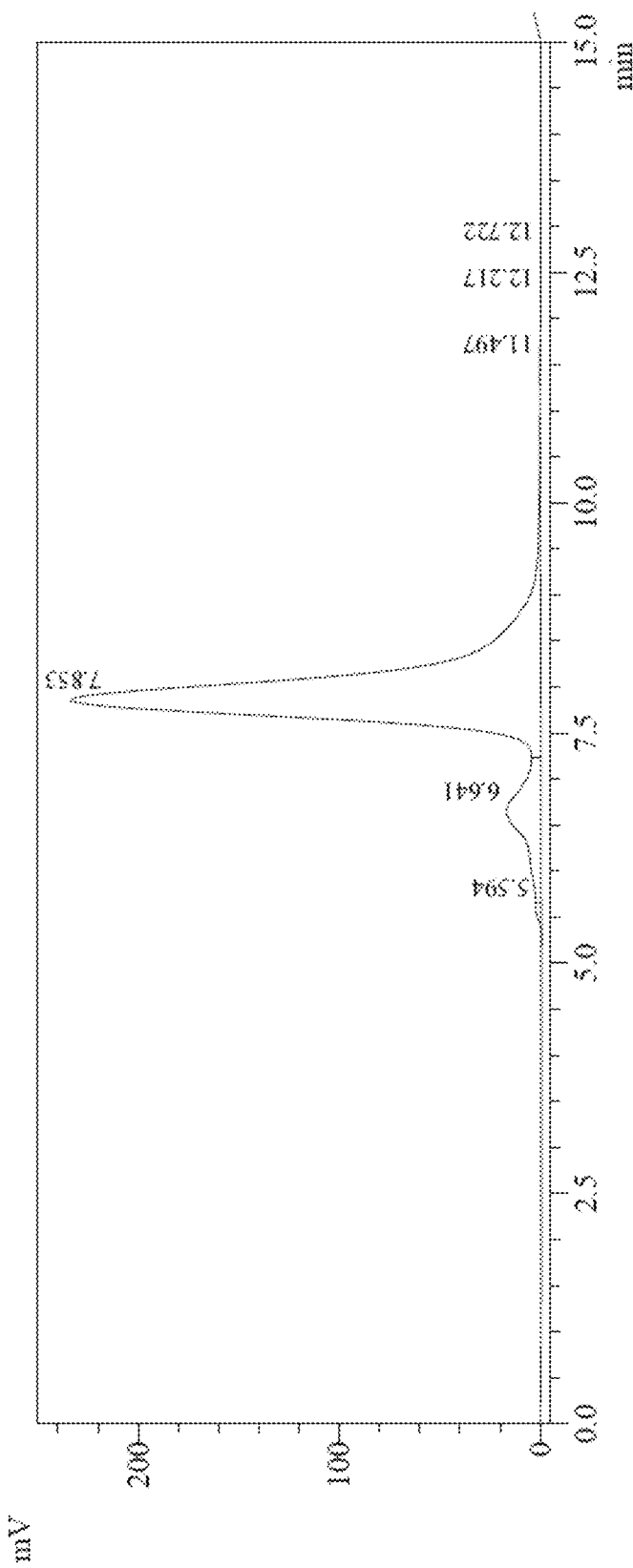
FIG. 1 shows in vitro evaluation of huA33-C825 biochemical purity by SE-HPLC chromatogram (UV 280 nm). The major peak at 7.853 minutes is the fully-paired bispecific antibody with an approximate molecular weight of 210 KDa.

The scope of present invention is defined by the claims appended hereto and is not limited by particular embodiments described herein; those skilled in the art, reading the present disclosure, will be aware of various modifications that may be equivalent to such described embodiments, or otherwise within the scope of the claims.

In general, terminology used herein is in accordance with its understood meaning in the art, unless clearly indicated otherwise. Explicit definitions of certain terms are provided below; meanings of these and other terms in particular instances throughout this specification will be clear to those skilled in the art from context.

References cited within this specification, or relevant portions thereof, are incorporated herein by reference.

In order that the present invention may be more readily understood, certain terms are first defined below. Additional definitions for the following terms and other terms are set forth throughout the specification.

"Affinity": As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

"Affinity matured" (or "affinity matured antibody"), as used herein, refers to an antibody with one or more alterations in one or more CDRs thereof which result an improvement in the affinity of the antibody for antigen, compared to a parent antibody which does not possess those alteration(s). In some embodiments, affinity matured antibodies will have nanomolar or even picomolar affinities for a target antigen. Affinity matured antibodies may be produced by any of a variety of procedures known in the art. Marks et al., 1992, BioTechnology 10:779-783 describes affinity maturation by $V_H$ and $V_L$ domain shuffling. Random mutagenesis of CDR and/or framework residues is described by: Barbas et al., 1994, Proc. Nat. Acad. Sci. U.S.A 91:3809-3813; Schier et al., 1995, Gene 169: 147-155; Yelton et al., 1995, J. Immunol. 155: 1994-2004; Jackson et al., 1995, J. Immunol. 154(7):3310-9; and Hawkins et al., 1992, J. Mol. Biol. 226:889-896.

"Amelioration", as used herein, refers to the prevention, reduction or palliation of a state, or improvement of the state of a subject. Amelioration includes, but does not require complete recovery or complete prevention of a disease, disorder or condition (e.g., radiation injury).

"Animal", as used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by DV. In some embodiments, an animal may be a transgenic animal, genetically engineered animal, and/or a clone.

"Antibody", as used herein, has its art understood meaning and refers to an immunoglobulin (Ig) that binds specifically to a particular antigen. As is known by those of ordinary skill in the art, antibodies produced in nature are typically comprised of four polypeptide chains, two heavy (H) chains and two light (L) chains. Each heavy and light chain is comprised of a variable region (abbreviated herein as HCVR or $V_H$ and LCVR or $V_L$, respectively) and a constant region. The constant region of a heavy chain comprises a $C_H1$, $C_H2$ and $C_H3$ domain (and optionally a $C_H4$ domain in the case of IgM and IgE). The constant region of a light chain is comprised of one domain, $C_L$. The $V_H$ and $V_L$ regions further contain regions of hypervariability, termed complementarity determining regions (CDRs), interspersed with regions that are more conserved, which are termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgM, IgD, IgG, IgA and IgE), class (e.g., IgG1, IgG2, IgG3, IgG4, IgA1 and IgA2) or subclass.

Antibody agent: As used herein, the term "antibody agent" refers to an agent that specifically binds to a particular antigen. In some embodiments, the term encompasses any polypeptide with immunoglobulin structural elements sufficient to confer specific binding. In various embodiments, suitable antibody agents may include, but are not limited to, monoclonal antibodies, polyclonal antibodies, humanized antibodies, primatized antibodies, chimeric antibodies, human antibodies, bi-specific or multi-specific antibodies, single domain antibodies (e.g., shark single domain antibodies (e.g., IgNAR or fragments thereof)), conjugated antibodies (i.e., antibodies conjugated or fused to other proteins, radiolabels, cytotoxins), Small Modular Immuno-Pharmaceuticals ("SMIPs™"), single chain antibodies, cameloid antibodies, antibody fragments, etc. In some embodiments, the term can refer to a stapled peptide. In some embodiments, the term can refer to an antibody-like binding peptidomimetic. In some embodiments, the term can refer to an antibody-like binding scaffold protein. In some embodiments, the term can refer to monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments, an included CDR is substantially identical to a reference CDR in that it is either identical in sequence or contains between 1-5 amino acid substitutions as compared with the reference CDR. In some embodiments, an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments, an included CDR is substantially identical to a reference CDR in that it shows at least 96%, 96%, 97%, 98%, 99%, or 100% sequence identity with the reference CDR. In some embodiments, an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an included CDR is substantially identical to a reference CDR in that at least one amino acid within the included CDR is substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain, which is homologous or largely homologous to an immunoglobulin-binding domain. In some embodiments, an antibody agent is or comprises a polypeptide that includes all CDRs found in a particular reference antibody chain or chains (e.g., heavy chain and/or light chain).

"Antibody component", as used herein, refers to a polypeptide element (that may be a complete polypeptide, or a portion of a larger polypeptide, such as for example a fusion polypeptide as described herein) that specifically binds to an epitope or antigen and includes one or more immunoglobulin structural features. In general, an antibody component is any polypeptide whose amino acid sequence includes elements characteristic of an antibody-binding region (e.g., an antibody light chain or variable region or one or more complementarity determining regions ("CDRs") thereof, or an antibody heavy chain or variable region or one or more CDRs thereof, optionally in presence of one or more framework regions). In some embodiments, an antibody component is or comprises a full-length antibody. In some embodiments, an antibody component is less than full-length but includes at least one binding site (comprising at least one, and preferably at least two sequences with structure of known antibody "variable regions"). In some embodiments, the term "antibody component" encompasses any protein having a binding domain, which is homologous or largely homologous to an immunoglobulin-binding domain. In particular embodiments, an included "antibody component" encompasses polypeptides having a binding domain that shows at least 99% identity with an immunoglobulin binding domain. In some embodiments, an included "antibody component" is any polypeptide having a binding domain that shows at least 70%, 75%, 80%, 85%, 90%, 95% or 98% identity with an immunoglobulin binding domain, for example a reference immunoglobulin binding domain. An included "antibody component" may have an amino acid sequence identical to that of an antibody (or a portion thereof, e.g., an antigen-binding portion thereof) that is found in a natural source. An antibody component may be monospecific, bi-specific, or multi-specific. An antibody component may include structural elements characteristic of any immunoglobulin class, including any of the human classes: IgG, IgM, IgA, IgD, and IgE. It has been shown that the antigen-binding function of an antibody can be performed by fragments of a full-length antibody. Such antibody embodiments may also be bispecific, dual-specific, or multi-specific formats specifically binding to two or more different antigens. Examples of binding fragments encompassed within the term "antigen-binding portion" of an antibody include (i) a Fab fragment, a monovalent fragment consisting of the $V_H$, $V_L$, $C_H1$ and $C_L$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_H$ and $V_L$ domains of a single arm of an antibody, (v) a dAb fragment (Ward et al., (1989) Nature 341:544-546), which comprises a single variable domain; and (vi) an isolated complementarity determining region (CDR). Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al., 1988, Science 242:423-426; and Huston et al., 1988, Proc. Natl. Acad. Sci. USA 85:5879-5883). In some embodiments, an "antibody component", as described herein, is or comprises such a single chain antibody. In some embodiments, an "antibody component" is or comprises a diabody. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. USA 90:6444-6448; Poljak, R. J., 1994, Structure 2(12):1121-1123). Such antibody binding portions are known in the art (Kontermann and Dubel eds., Antibody Engineering (2001) Springer-Verlag. New York. 790 pp. (ISBN 3-540-41354-5). In some embodiments, an antibody component is or comprises a single chain "linear antibody" comprising a pair of tandem Fv segments ($V_H$-$C_H1$-$V_H$-$C_H1$) which, together with complementary light chain polypeptides, form a pair of antigen binding regions (Zapata et al., 1995, Protein Eng. 8(10): 1057-1062; and U.S. Pat. No. 5,641,870). In some embodiments, an antibody component may have structural elements characteristic of chimeric or humanized antibodies. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some embodiments, an antibody component may have structural elements characteristic of a human antibody.

"Biological activity", as used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

"Bispecific antibody", as used herein, refers to a bispecific binding agent in which at least one, and typically both, of the binding moieties is or comprises an antibody component. A variety of different bi-specific antibody structures are known in the art. In some embodiments, each binding moiety in a bispecific antibody that is or comprises an antibody component includes $V_H$ and/or $V_L$ regions; in some such embodiments, the $V_H$ and/or $V_L$ regions are those found in a particular monoclonal antibody. In some embodiments, where the bispecific antibody contains two antibody component-binding moieties, each includes $V_H$ and/or $V_L$ regions from different monoclonal antibodies. In some embodiments, where the bispecific antibody contains two antibody component binding moieties, wherein one of the two antibody component binding moieties includes an immunoglobulin molecule having $V_H$ and/or $V_L$ regions that contain CDRs from a first monoclonal antibody, and one of the two antibody component binding moieties includes an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

"Bispecific binding agent", as used herein, refers to a polypeptide agent with two discrete binding moieties, each of which binds with a distinct target. In some embodiments, a bispecific binding agent is or comprises a single polypeptide; in some embodiments, a bispecific binding agent is or comprises a plurality of peptides which, in some such embodiments may be covalently associated with one another, for example by cross-linking. In some embodiments, the two binding moieties of a bispecific binding agent recognize different sites (e.g., epitopes) the same target (e.g., antigen); in some embodiments, they recognize different targets. In some embodiments, a bispecific binding agent is capable of binding simultaneously to two targets that are of different structure.

"Carrier", as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

"CDR", as used herein, refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Certain systems have been established in the art for defining CDR boundaries (e.g., Kabat, Chothia, etc.); those skilled in the art appreciate the differences between and among these systems and are capable of understanding CDR boundaries to the extent required to understand and to practice the claimed invention.

"CDR-grafted antibody", as used herein, refers to an antibody whose amino acid sequence comprises heavy and light chain variable region sequences from one species but in which the sequences of one or more of the CDR regions of $V_H$ and/or $V_L$ are replaced with CDR sequences of another species, such as antibodies having murine $V_H$ and $V_L$ regions in which one or more of the murine CDRs (e.g., CDR3) has been replaced with human CDR sequences. Likewise, a "CDR-grafted antibody" may also refer to antibodies having human $V_H$ and $V_L$ regions in which one or more of the human CDRs (e.g., CDR3) has been replaced with mouse CDR sequences.

"Chimeric antibody", as used herein, refers to an antibody whose amino acid sequence includes $V_H$ and $V_L$ region sequences that are found in a first species and constant region sequences that are found in a second species, different from the first species. In many embodiments, a chimeric antibody has murine $V_H$ and $V_L$ regions linked to human constant regions. In some embodiments, an antibody with human $V_H$ and $V_L$ regions linked to non-human constant regions (e.g., a mouse constant region) is referred to as a "reverse chimeric antibody".

"Combination therapy": As used herein, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens.

"Comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Corresponding to", as used herein designates the position/identity of an amino acid residue in a polypeptide of interest. Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids.

"Detection Agents", as described herein, refer to moieties or agents that are amenable to detection, for example, due to their specific structural and/or chemical characteristics, and/or their functional properties. Non-limiting examples of such agents include enzymes, radiolabels, haptens, fluorescent labels, phosphorescent molecules, chemiluminescent molecules, chromophores, luminescent molecules, photoaffinity molecules, colored particles or ligands, such as biotin. Many detection agents are known in the art, as are systems for their attachment to antibodies (see, for e.g., U.S. Pat. Nos. 5,021,236; 4,938,948; and 4,472,509, each incorporated herein by reference). Particular examples may include paramagnetic ions, radioactive isotopes, fluorochromes, NMR-detectable substances, X-ray imaging agents, among others. In some embodiments of the present invention, the conjugated detection agent is a diagnostic or imaging agent.

"Dosage form" and "unit dosage form", as used herein, the term "dosage form" refers to physically discrete unit of a therapeutic agent for a subject (e.g., a human patient) to be treated. Each unit contains a predetermined quantity of active material calculated or demonstrated to produce a desired therapeutic effect when administered to a relevant population according to an appropriate dosing regimen. For example, in some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). It will be understood, however, that the total dosage administered to any particular patient will be selected by a medical professional (e.g., a medical doctor) within the scope of sound medical judgment.

"Dosing regimen" (or "therapeutic regimen"), as used herein is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously (e.g., by infusion) over a predetermined period. In some embodiments, a therapeutic agent is administered once a day (QD) or twice a day (BID). In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

"Effector function" as used herein refers a biochemical event that results from the interaction of an antibody Fc region with an Fc receptor or ligand. Effector functions include but are not limited to antibody-dependent cell-mediated cytotoxicity (ADCC), antibody-dependent cell-mediated phagocytosis (ADCP), and complement-mediated cytotoxicity (CMC). In some embodiments, an effector function is one that operates after the binding of an antigen, one that operates independent of antigen binding, or both.

"Effector cell" as used herein refers to a cell of the immune system that expresses one or more Fc receptors and mediates one or more effector functions. In some embodiments, effector cells may include, but may not be limited to, one or more of monocytes, macrophages, neutrophils, dendritic cells, eosinophils, mast cells, platelets, large granular lymphocytes, Langerhans' cells, natural killer (NK) cells, T-lymphocytes, B-lymphocytes and may be from any organism including but not limited to humans, mice, rats, rabbits, and monkeys.

"Engineered" as used herein refers, in general, to the aspect of having been manipulated by the hand of man. For example, in some embodiments, a polynucleotide may be considered to be "engineered" when two or more sequences, that are not linked together in that order in nature, are manipulated by the hand of man to be directly linked to one another in the engineered polynucleotide. In some particular such embodiments, an engineered polynucleotide may comprise a regulatory sequence that is found in nature in operative association with a first coding sequence but not in operative association with a second coding sequence, is linked by the hand of man so that it is operatively associated with the second coding sequence. Alternatively or additionally, in some embodiments, first and second nucleic acid sequences that each encode polypeptide elements or domains that in nature are not linked to one another may be linked to one another in a single engineered polynucleotide. Comparably, in some embodiments, a cell or organism may be considered to be "engineered" if it has been manipulated so that its genetic information is altered (e.g., new genetic material not previously present has been introduced, or previously present genetic material has been altered or removed). As is common practice and is understood by those in the art, progeny of an engineered polynucleotide or cell are typically still referred to as "engineered" even though the actual manipulation was performed on a prior entity. Furthermore, as will be appreciated by those skilled in the art, a variety of methodologies are available through which "engineering" as described herein may be achieved. For example, in some embodiments, "engineering" may involve selection or design (e.g., of nucleic acid sequences, polypeptide sequences, cells, tissues, and/or organisms) through use of computer systems programmed to perform analysis or comparison, or otherwise to analyze, recommend, and/or select sequences, alterations, etc). Alternatively or additionally, in some embodiments, "engineering" may involve use of in vitro chemical synthesis methodologies and/or recombinant nucleic acid technologies such as, for example, for example, nucleic acid amplification [e.g., via the polymerase chain reaction], hybridization, mutation, transformation, transfection, etc, and/or any of a variety of controlled mating methodologies). As will be appreciated by those skilled in the art, a variety of established such techniques (e.g., for for recombinant DNA, oligonucleotide synthesis, and tissue culture and transformation [e.g., electroporation, lipofection, etc] are well known in the art and described in various general and more specific references that are cited and/or discussed throughout the present specification. See e.g., Sambrook et al., Molecular Cloning: A Laboratory Manual (2d ed., Cold Spring Harbor Laboratory Press, Cold Spring Harbor, N.Y. [1989]), which is incorporated herein by reference for any purpose.

"Epitope", as used herein, includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

"Excipient", as used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

"Fc ligand" as used herein refers to a molecule, preferably a polypeptide, from any organism that binds to the Fc region of an antibody to form an Fc-ligand complex. Fc ligands include but are not limited to FcγRIIA (CD32A), FcγRIIB (CD32B), FcγRIIIA (CD16A), FcγRIIIB (CD16B), FcγRI (CD64), FccRII (CD23), FcRn, C1q, C3, staphylococcal protein A, streptococcal protein G, and viral FcγR. Fc ligands may include undiscovered molecules that bind Fc.

"Fluorescent Label", as is understood in the art, is a moiety or entity that has fluorescent character and, in some embodiments, may be detectable based on such fluorescence. In some embodiments, a fluorescent label may be or may comprise one or more of Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

"Framework" or "framework region", as used herein, refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

"Host cell", as used herein, refers to a cell into which exogenous DNA (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-1 1 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3 A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

"Human antibody", as used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), for example in one or more CDRs and in particular CDR3.

"Humanized", as is known in the art, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$, hinge, $C_H2$, $C_H3$, and, optionally, a $C_H4$ region of a heavy chain constant region. In some embodiments, a humanized antibody only contains a humanized $V_L$ region. In some embodiments, a humanized antibody only contains a humanized $V_H$ region. In some certain embodiments, a humanized antibody contains humanized $V_H$ and $V_L$ regions.

"Improve," "increase" or "reduce," as used herein or grammatical equivalents thereof, indicate values that are relative to a baseline measurement, such as a measurement in the same individual prior to initiation of a treatment described herein, or a measurement in a control individual (or multiple control individuals) in the absence of the treatment described herein. A "control individual" is an individual afflicted with the same form of disease or injury as the individual being treated.

"In vitro", as used herein refers to events that occur in an artificial environment, e.g., in a test tube or reaction vessel, in cell culture, etc., rather than within a multi-cellular organism.

"In vivo", as used herein refers to events that occur within a multi-cellular organism, such as a human and a non-human animal. In the context of cell-based systems, the term may be used to refer to events that occur within a living cell (as opposed to, for example, in vitro systems).

"Isolated", as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

"$K_D$", as used herein, refers to the dissociation constant of a binding agent (e.g., an antibody or binding component thereof) from a complex with its partner (e.g., the epitope to which the antibody or binding component thereof binds).

"$k_{off}$", as used herein, refers to the off rate constant for dissociation of a binding agent (e.g., an antibody or binding component thereof) from a complex with its partner (e.g., the epitope to which the antibody or binding component thereof binds).

"$k_{on}$", as used herein, refers to the on rate constant for association of a binding agent (e.g., an antibody or binding component thereof) with its partner (e.g., the epitope to which the antibody or binding component thereof binds).

"Linker", as used herein, typically refers to a portion of a molecule or entity that connects two or more different regions of interest (e.g., particular structural and/or functional domains or moieties of interest). In some embodiments, a linker does not participate significantly in the relevant function of interest (e.g., so that presence or absence of the linker, in association with the relevant domain or moiety of interest does not materially alter the relevant function of the domain or moiety). In some embodiments, a linker in characterized by lack of defined or rigid structure. In some embodiments, particularly when one or more domains or moieties of interest is/are comprised of a polypeptide, a linker is or comprises a polypeptide. In some particular embodiments, a polypeptide (e.g., an engineered polypeptide) as described herein may have general structure S1-L-S2, wherein S1 and S2 are the moieties or domains of interest. In some embodiments, one or both of S1 and S2 may be or comprise a binding element (e.g., an antibody component) as described herein. In some embodiments, a polypeptide linker may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids long. In some embodiments, a polypeptide linker may have an amino acid sequence that is or comprises a sequence as described in Holliger, P., et al., 1993, Proc. Natl. Acad. Sci. USA 90:6444-6448 or Poljak, R. J., et al., 1994, Structure 2: 1121-1123. In some embodiments, a polypeptide linker may have an amino acid sequence that is or comprises GGGGSGGGGSGGGGS (i.e., [$G_4S$]$_3$) (SEQ ID NO: 8) or GGGGSGGGGSGGGGSGGGGSGGGGSGGGGS (i.e., [$G_4S$]$_6$) (SEQ ID NO: 9).

"Multivalent binding agent", as used herein, refers a binding agent capable of binding to two or more antigens, which can be on the same molecule or on different molecules. Multivalent binding agents as described herein are, in some embodiments, engineered to have the three or more antigen binding sites, and are typically not naturally occurring proteins. Multivalent binding agents as described herein refer to binding agents capable of binding two or more related or unrelated targets. Multivalent binding agents may be composed of multiple copies of a single antibody component or multiple copies of different antibody components. Such binding agents are capable of binding to two or more antigens and are tetravalent or multivalent binding agents. Multivalent binding agents may additionally comprise a therapeutic agent, such as, for example, an immunomodulator, toxin or an RNase. Multivalent binding agents as described herein are, in some embodiments, capable of binding simultaneously to at least two targets that are of different structure, e.g., two different antigens, two different epitopes on the same antigen, or a hapten and/or an antigen or epitope. In many embodiments, multivalent binding agents of the present invention are proteins engineered to have characteristics of multivalent binding agents as described herein. Multivalent binding agents of the present invention may be monospecific (capable of binding one antigen) or multispecific (capable of binding two or more antigens), and may be composed of two heavy chain polypeptides and two light chain polypeptides. Each binding site, in some embodiments, is composed of a heavy chain variable domain and a light chain variable domain with a total of six CDRs involved in antigen binding per antigen binding site.

"Nucleic acid", as used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

"Operably linked", as used herein, refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

"Paramagnetic Ion", as is understood in the art, refers to an ion with paramagnetic character. In some embodiments, a paramagnetic ion is one or more of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III).

"Payload", as used herein, refers to a moiety or entity that is delivered to a site of interest (e.g., to a cell, tissue, tumor, or organism) by association with another entity. In some embodiments, a payload is or comprises a detection agent. In some embodiments, a payload entity is or comprises a therapeutic agent. In some embodiments, a payload entity is or comprises a catalytic agent. Those of ordinary skill in the art will appreciate that a payload entity may be of any chemical class. For example, in some embodiments, a payload entity may be or comprise a carbohydrate, an isotope, a lipid, a nucleic acid, a metal, a nanoparticle (e.g., a ceramic or polymer nanoparticle), polypeptide, a small molecule, a virus, etc. To give but a few examples, in some embodiments, a therapeutic agent payload may be or comprise a toxin (e.g., a toxic peptide, small molecule, or isotope [e.g., radioisotope]); in some embodiments, a detection agent payload may be or comprise a fluorescent entity or agent, a radioactive entity or agent, an agent or entity detectable by binding (e.g., a tag, a hapten, a ligand, etc), a catalytic agent, etc.

"Physiological conditions", as used herein, has its art-understood meaning referencing conditions under which cells or organisms live and/or reproduce. In some embodiments, the term refers to conditions of the external or internal milieu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20 to 40° C., atmospheric pressure of 1, pH of 6 to 8, glucose concentration of 1 to 20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

"Polypeptide", as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30 to 40%, and is often greater than about 50%, 60%, 70%, 80%, 90%, 91%, 92%, 93%, 94%, 95%, 96%, 97%, 98%, 99% or more and/or includes at least one region (i.e., a conserved region that may in some embodiments may be or comprise a characteristic sequence element) that shows very high sequence identity, often greater than 90% or even 95%, 96%, 97%, 98%, or 99%. Such a conserved region usually encompasses at least three to four and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice-versa, and/or fragments may be present in a different order in the polypeptide of interest than in the parent), so that the polypeptide of interest is a derivative of its parent polypeptide "Prevent" or "prevention", as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

"Radioactive Isotope": The term "radioactive isotope" as used herein has its art-understood meaning referring to an isotope that undergoes radioactive decay. In some embodiments, a radioactive isotope may be or comprise one or more of actinium-225, astatine-211, bismuth-212, carbon-14, chromium-51, chlorine-36, cobalt-57, cobalt-58, copper-67, Europium-152, gallium-67, hydrogen-3, iodine-123, iodine-124, iodine-125, iodine-131, indium-111, iron-59, lead-212, lutetium-177, phosphorus-32, radium-223, radium-224, rhenium-186, rhenium-188, selenium-75, sulphur-35, technicium-99m, thorium-227, yttrium-90, and zirconium-89.

"Recombinant", as used herein, is intended to refer to polypeptides (e.g., antibodies or antibody components, or multispecific binding agents as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., 1997, TIB Tech. 15:62-70; Azzazy H., and Highsmith W. E., 2002, Clin. Biochem. 35:425-445; Gavilondo, J. V. and Larrick, J. W., 2002, BioTechniques 29: 128-145; Hoogenboom H., and Chames, P., 2000, Immunology Today 21:371-378), antibodies isolated from an animal (e.g., a mouse) that is transgenic for human immunoglobulin genes (see e.g., Taylor, L. D. et al., 1992, Nucl. Acids Res. 20:6287-6295; Little M. et al., 2000, Immunology Today 21:364-370; Kellermann S-A., and Green L. L., 2002, Current Opinion in Biotechnology 13:593-597; Murphy, A. J. et al., 2014, Proc. Natl. Acad. Sci. U.S.A. 111(14):5153-5158) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant antibody polypeptide is comprised of sequences found in the germline of a source organism of interest (e.g., human, mouse, etc.). In some embodiments, a recombinant antibody has an amino acid sequence that resulted from mutagenesis (e.g., in vitro or in vivo, for example in a transgenic animal), so that the amino acid sequences of the $V_H$ and $V_L$ regions of the recombinant antibodies are sequences that, while originating from and related to germline $V_H$ and $V_L$ sequences, may not naturally exist within the germline antibody repertoire in vivo.

"Recovering", as used herein, refers to the process of rendering an agent or entity substantially free of other previously-associated components, for example by isolation, e.g., using purification techniques known in the art. In some embodiments, an agent or entity is recovered from a natural source and/or a source comprising cells.

"Reference", as used herein describes a standard, control, or other appropriate reference against which a comparison is made as described herein. For example, in some embodiments, a reference is a standard or control agent, animal, individual, population, sample, sequence, series of steps, set of conditions, or value against which an agent, animal, individual, population, sample, sequence, series of steps, set of conditions, or value of interest is compared. In some embodiments, a reference is tested and/or determined substantially simultaneously with the testing or determination of interest. In some embodiments, a reference is a historical reference, optionally embodied in a tangible medium. Typically, as would be understood by those skilled in the art, a reference is determined or characterized under conditions comparable to those utilized in the assessment of interest.

"Risk", as will be understood from context, "risk" of a disease, disorder, and/or condition comprises likelihood that a particular individual will develop a disease, disorder, and/or condition (e.g., a radiation injury). In some embodiments, risk is expressed as a percentage. In some embodiments, risk is from 0, 1, 2, 3, 4, 5, 6, 7, 8, 9, 10, 20, 30, 40, 50, 60, 70, 80, 90 and up to 100%. In some embodiments risk is expressed as a risk relative to a risk associated with a reference sample or group of reference samples. In some embodiments, a reference sample or group of reference samples have a known risk of a disease, disorder, condition and/or event (e.g., a radiation injury). In some embodiments a reference sample or group of reference samples are from individuals comparable to a particular individual. In some embodiments, relative risk is 0, 1, 2, 3, 4, 5, 6, 7, 8, 9, 10 or more.

"Specific binding", as used herein, refers to a binding agent's ability to discriminate between possible partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

"Subject", as used herein, means any mammal, including humans. In certain embodiments of the present invention the subject is an adult, an adolescent or an infant. In some embodiments, terms "individual" or "patient" are used and are intended to be interchangeable with "subject". Also contemplated by the present invention are the administration of the pharmaceutical compositions and/or performance of the methods of treatment in-utero.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Substantial sequence homology", as used herein refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table 1 and 2.

TABLE 1

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

TABLE 2

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., 1990, J. Mol. Biol., 215(3): 403-410; Altschul et al., 1996, Methods in Enzymology 266:460-80; Altschul et al., 1997, Nucleic Acids Res. 25:3389-3402; Baxevanis et al., 1998, Bioinformatics: A Practical Guide to the Analysis of Genes and Proteins, Wiley; and Misener et al., (eds.), Bioinformatics Methods and Protocols (Methods in Molecular Biology, Vol. 132), Humana Press, 1999; all of the foregoing of which are incorporated herein by reference. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

"Substantial identity", as used herein refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., 1990, J. Mol. Biol., 215(3): 403-410; Altschul et al., 1996, Methods in Enzymology 266:460-80; Altschul et al., 1997, Nucleic Acids Res. 25:3389-3402; Baxevanis et al., 1998, Bioinformatics: A Practical Guide to the Analysis of Genes and Proteins, Wiley; and Misener et al., (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. In the context of a CDR, reference to "substantial identity" typically refers to a CDR having an amino acid sequence at least 80%, preferably at least 85%, at least 90%, at least 95%, at least 98% or at least 99% identical to that of a reference CDR.

"Surface plasmon resonance", as used herein, refers to an optical phenomenon that allows for the analysis of specific binding interactions in real-time, for example through detection of alterations in protein concentrations within a biosensor matrix, such as by using a BIAcore system (Pharmacia Biosensor AB, Uppsala, Sweden and Piscataway, N.J.). For further descriptions, see Jonsson, U., et al., 1993, Ann. Biol. Clin. 51:19-26; Jonsson, U., et al., 1991, Biotechniques 11:620-627; Johnsson, B., et al., 1995, J. Mol. Recognit. 8:125-131; and Johnnson, B., et al., 1991, Anal. Biochem. 198:268-277.

"Therapeutically effective amount", as used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

"Transformation", as used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

"Vector", as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

DETAILED DESCRIPTION OF CERTAIN EMBODIMENTS

The present invention demonstrates the successful construction of a multi-specific binding agent (e.g., bispecific antibody) that binds an established antigen on human colorectal cancers. In particular, the present disclosure specifically demonstrates the successful targeting of radioimmunotherapy in colorectal cancer using a bispecific antibody that binds to human A33 glycoprotein antigen and Benzyl-1,4,7,10-tetraazacyclododecane-1,4,7,10-tetraacetic acid (DOTA-Bn), provides a specific such bispecific antibody, and demonstrates its surprising usefulness and/or effectiveness.

Among other things, the present invention specifically provides the first successful therapeutic use of a bispecific antibody that targets the human A33 antigen, and furthermore provides an improved therapeutic methodology for a pretargeted radioimmunotherapy regimen for treatment of A33-expressing tumors. The present invention also provides "theranostic" (i.e., therapeutic and diagnostic) agents for the simultaneous scintigraphic imaging and radioimmunotherapy of A33-positive cancers, and specifically demonstrates surprising usefulness and/or effectiveness thereof.

A33, a glycoprotein antigen on human colorectal cancers with restricted normal tissue expression, is retained on the tumor cell surface after antibody binding for extended periods of time, in contrast to the rapid physiologic turnover of normal gut epithelium—a therapeutic index based on tissue retention unique to gut antigens. Radioimmunoscintigraphy and radioimmunotherapy (RIT) of advanced colorectal cancer ("CRC") using directly conjugated antibodies (e.g. $^{131}$I-huA33) has yielded suboptimal tumor dose and therapeutic index (Welt et al., 1994, J. Clin. Oncol. 12:1561-1571). The present invention encompasses the recognition that both of these deficiencies can be overcome using a multi-step pretargeted RIT (PRIT) approach where a bispecific tetravalent huA33-C825 bispecific antibody construct with high affinity for Benzyl-1,4,7,10-tetraazacyclododecane-N,N',N'',N'''-tetraacetic acid (DOTA-Bn)-radiometal complexes is first targeted to the tumor. The present disclosure specifically demonstrates that subsequent to clearing unbound huA33-C825 bispecific antibody from circulation, $^{177}$Lu-radiolabeled DOTA-Bn hapten is injected to deliver the tumorcidal dose of PRIT to the A33-positive tumor. To give one specific example, the present disclosure demonstrates that in human colorectal tumor models of SW1222, mice with established subcutaneous tumors can be cured with minimal toxicity to normal tissues including bone marrow and kidney.

Without wishing to be bound by theory, we note that data provided herein demonstrate that, in some embodiments, a PRIT regimen that employs a dual-cycle dose of a huA33-C825 bispecific antibody resulted in an tremendous effect on tumor volume as compared to the same PRIT regimen that employed a single-cycle dose. Moreover, the present disclosure demonstrates, among other things, that such dual-cycle dosing of a huA33-C825 bispecific antibody as described herein yielded a complete response in approximately 80% of test subjects. Also demonstrated herein are treatments with additional cycles, which showed highly efficient responses, for example a 3 cycle dosing regimin was curative for 10/10 mice without detectable toxicity in target organs (marrow spleen and kidney). Thus, the present disclosure, in at least some embodiments, embraces the development of an improved PRIT regimen using a bispecific antibody format that effectively targets the human A33 glycoprotein antigen to achieve enhanced tumor targeting and/or tumor ablation with minimal to no clinical or histological radiation toxicity.

Human Colorectal Cancer

The human A33 antigen is a transmembrane glycoprotein having a molecular weight of 43 kD (213 amino acid polypeptide), and is expressed in more than 95% of human colon cancers with restricted normal expression (colon and bowel epithelium) and minimal shedding into circulation. Initially a murine monoclonal antibody (A33) and later a humanized version (huA33) was developed (King et al., 1995, British J. Cancer 72:1364-1372), and found to have ideal specificity, affinity, and antibody-antigen uptake and internalization properties for use as a targeting agent for radioisotopes for diagnosis and therapy. In a clinical study of $^{124}$I-huA33 imaging in colorectal cancer patients, differential clearance between antigen-positive tumor and intestine led the authors to conclude that an alternative multi-step approach including initial administration with a non-radioactive bispecific A33 antibody form (or "pretargeting"), followed with a radiolabeled hapten may be preferred (O'Donoghue et al., 2011, J. Nucl. Med. 52:1878-1885). The high tumor persistence of radioiodine forms of A33 (e.g., $^{125I\text{-}}$A33) prompted extensive investigation of the internalization properties of the A33 antibody-antigen complex, showing that anti-A33 antibodies reside on the surface for extended periods of time, making such an antibody, in some embodiments, particularly well suited for a pretargeting approach (Ackerman et al., 2008, Mol. Cancer Ther. 7(7):2233-2240), in particular, when the normal expression in the gut is allowed to turnover before a last ligand step. The unique physiology of the gut epithelium to shed over one to three days carrying with it antigens and bound antibodies is critical if the target antigen is expressed on these normal cells (Scott et al., 2005, Clin. Cancer Res. 11:4810-4817). As described herein, in PRIT, unbound antibodies are cleared from the blood using a clearing agent (CA) before a last cytotoxic ligand step. The natural shedding of normal gut cells is functionally equivalent to a clearing step in the gut. Pretargeted radioimmunotherapy (PRIT) directed at a variety of other tumor-associated antigens has been investigated for colorectal cancer, including CEA (hMN-14-anti-DTPA-indium+$^{131}$I-di-DTPA-indium hapten and recently, anti-CEACAMS-anti-histamine-succinyl-glycine "TF2" with $^{177}$Lu-IMP288 hapten), TAG-72 (CC49 scFv-streptavidin+$^{90}$Y-DOTA-biotin), Ep-CAM (NR-LU-10-SA with $^{90}$Y-DOTA-biotin).

Using antibodies to target poisons to tumors, e.g., radioimmunotherapy (RIT) with directly conjugated antibodies, has so far been met with limited success due in part to suboptimal tumor dose and therapeutic index (TI). Further, because of normal tissue bystander toxicity, dose escalation is not feasible and therefore such therapy results in limited anti-tumor effect. Thus, the present invention is based on the recognition that because the human A33 glycoprotein antigen is present in colorectal cancers and possesses unique retention properties, a PRIT methodology that achieves log-fold higher TI and complete remissions of established xenografts without toxicity to any major organs could be developed to effectively target human A33 on tumor cells using a bispecific antibody (referred to herein as huA33-C825) having a first antigen-binding site that binds human A33 and a second antigen-binding site with high affinity for DOTA-Bn (metal) complex (e.g., specificity through the single chain Fv (scFv) referred to as C825). As described herein, a PRIT methodology was improved in vivo by titrating doses of huA33-C825, a dextran-based clearing agent (dextran-CA), and a $^{177}$Lu-radiolabeled DOTA-Bn hapten ($^{177}$Lu-DOTA-Bn) using a subcutaneous colorectal cancer xenograft model of SW1222.

As described herein, bispecific binding agents of the present invention offer dual functionality in diagnostic imaging/dosimetry and therapeutic applications. Targeted radiation therapy, called radioimmunotherapy (RIT), can deliver sufficient radiation to overcome any tumor resistance, as long as the TI is favorable. Current radiolabeled IgG drugs (e.g. $^{90}$Y-Zevalin) have suboptimal TI of 3:1, borderline for curative therapy where hematological toxicity is dose limiting. The present invention is encompasses the recognition that in pretargeted RIT (PRIT) an antibody targeting step is separate from the payload step. The present disclosure appreciates one potential additional advantage of PRIT over conventional MT in that in some embodiments, PRIT may facilitate patient care. In some embodiments, an initial infusion of cold antibody, and in some embodiments an administration of a clearing agent, can be performed in a physician's office (e.g., in the office of a managing physician). In some embodiments, only a step of radiolabeled DOTA-Bn (typically performed subsequent to one or more, and in some embodiments, all, other steps), would need to be done by a nuclear medicine trained physician, and the patient may then be returned to his or her physician's care, once radioactivity has cleared from the body (<24 hours). Therefore, by taking advantage of the unique pharmacokinetics of large and small ligands, the present inventors demonstrate herein that PRIT can be highly effective. The present invention specifically demonstrates that using a fully humanized PRIT system that exploits DOTA-Bn (Bn=benzyl) has significant curative potential in a mouse xenograft model. As TIs improve by >10-fold, no clinical or histologic toxicities are observed. As theranostics, PRIT dosimetry using either PET or SPECT has yielded highly reproducible dose estimates. While radioisotopes provide initial proof of principle, PRIT may be applicable to any payloads linked to DOTA-Bn, including nanoparticles, peptides, toxins, drugs and viruses. The present inventors have applied their PRIT method to target the human A33 antigen because of its high mortality in the United States. For example, A33-positive tumors are involved in high mortality in colorectal cancer (49700 annual deaths), gastric cancer (10720 annual deaths), and pancreatic cancer (39590 annual deaths). Currently, no curative therapy is available for any of these metastatic cancers.

As described herein, the present inventors have developed a bispecific antibody termed huA33-C825 using the variable region sequences of humanized antibody A33 (King et al., 1995, Brit. J. Cancer 72:1364-1372) and C825, a murine scFv antibody with high affinity for benzyl-1,4,7,10-tetraazacyclododecane-N,N',N",N'"-tetraacetic acid (DOTA-Bn)-radiometal complexes (Orcutt el al., 2011, Nucl. Med. Biol. 38:223-233), to demonstrate an improved PRIT methodology in mice bearing established s.c. SW1222 human colorectal carcinoma xenografts. We note that data provided herein specifically demonstrates that using such an improved PRIT as described herein provides tumor-to-normal tissues ratios of 105:1 (blood) and 18:1 (kidney) at 24 hours (h) post-injection (p.i.). Further, as described herein, biodistribution of $^{177}$Lu-DOTA-Bn from 2-120 h p.i., estimated absorbed doses (cGy/MBq) to tumor, blood, liver, spleen, and kidney for PRIT were 65.8, 0.9 (therapeutic index (TI): 73), 6.3 (TI: 10), 6.6 (TI: 10), and 5.3 (TI: 12), respectively. Thus, in some embodiments, the PRIT regimen employing the huA33-C825 bispecific antibody described herein provides an improved therapeutic index and optimal tumor dose in the treatment of a human colorectal xenograft. We also note that data provided herein specifically demonstrates that dual-cycle PRIT treatment (66.6 or 111 MBq $^{177}$Lu-DOTA-Bn, see Table 7) of established tumors produced 9/9 complete responses and 2/9 alive without recurrence at more than 140 d. Further, in the other 7, the time to reach tumor size of 500 mm$^3$ were 27±26 d for 66.6 MBq and 40±6 d for 111 MBq, compared to 13±2 d for non-treated mice. There were no clinical or histologic evidence of radiation induced toxicities. Thus, the data provided herein confirms that bispecific antibodies described herein represent cancer therapeutics characterized by improved efficacy and safety profiles, and a multi-step PRIT approach, as described herein, could deliver safe and effective radiation using the 0-emitting isotope $^{177}$Lu to ablate established colorectal tumors.

Humanized Antibodies

In some embodiments, antibodies for use in accordance with the present invention are monoclonal antibodies, and/or in some embodiments may be humanized versions of cognate anti-A33 antibodies that were prepared in other species. In some embodiments, a humanized antibody is one which some or all of the amino acids of a human immunoglobulin light or heavy chain that are not required for antigen binding (e.g., the constant regions and the framework regions of the variable domains) are used to substitute for the corresponding amino acids from the light or heavy chain of a cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. In some embodiments, one or more residues in the human framework regions can be changed to residues at the corresponding positions in the murine antibody so as to preserve the binding affinity of the humanized antibody to the antigen. Such a change is sometimes called "back mutation." Similarly, forward mutations may be made to revert back to murine sequence for a desired reason, e.g. stability or affinity to antigen. Humanized antibodies generally are less likely to elicit an immune response in humans as compared to chimeric human antibodies because the former contain considerably fewer non-human components.

In some embodiments, a humanized antibody is produced by recombinant DNA technology. Alternatively or additionally, suitable methods for making humanized antibodies of the present invention are described in, e.g., EP0239400; Jones et al., 1986, Nature 321:522-525; Riechmann et al., 1988, Nature 332:323-327; Verhoeyen et al., 1988, Science 239:1534-1536; Queen et al., 1989, Proc. Nat. Acad. Sci. U.S.A. 86:10029; U.S. Pat. No. 6,180,370; and Orlandi et al., 1989, Proc. Natl. Acad. Sci. U.S.A. 86:3833; the disclosures of all of which are incorporated by reference herein in their entireties. Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs, encoding the CDRs are inserted into the corresponding regions of a human antibody heavy or light chain variable domain coding sequences, attached to human constant region gene segments of a desired isotype (e.g., γ1 for $C_H$ and κ for $C_L$), are gene synthesized. The humanized heavy and light chain genes are co-expressed in mammalian host cells (e.g., CHO or NSO cells) to produce soluble humanized antibody. To facilitate large-scale production of antibodies, it is often desirable to select for a high expressor using a DHFR gene or GS gene in the producer line. These producer cell lines are cultured in bioreactors, or hollow fiber culture system, or WAVE technology, to produce bulk cultures of soluble antibody, or to produce transgenic mammals (e.g., goats, cows, or sheep) that express the antibody in milk (see, e.g., U.S. Pat. No. 5,827,690).

As described herein, multi-specific binding agents (e.g., bispecific antibodies) were engineered utilizing sequences and/or components found in the humanized antibody A33 described in King et al., 1995 (supra). Other murine anti-A33 antibodies may be humanized (e.g., as described herein) and may be employed in the engineering of multi-specific binding agents as described herein. For example, cDNAs encoding variable regions of light and/or heavy chains of one or more (typically only one) candidate murine anti-A33 antibody(ies) are used to construct vectors for expression of murine-human chimeras in which the murine anti-A33 antibody variable regions are linked to human IgG1 (for heavy chain) and human kappa (for light chain) constant regions, as described previously. Alternatively or additionally, in some embodiments, novel forms of humanized anti-A33 antibodies with variant glycosylation can be created, for example in order to enhance binding to the Fc receptor and enhance antigen affinity if so desired.

In some embodiments, in order to produce humanized anti-A33 antibodies, human acceptor framework domains can be chosen by homology matching to human germline sequences. Using such chosen human acceptor frameworks, the light and heavy chain variable domains are designed and a number of variants/versions of each can be generated and expressed.

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and International Patent Application Publications WO 98/46645, WO 98/60433, WO 98/24893, WO 98/16664, WO 96/34096, WO 96/33735, and WO 91/10741; each of which is incorporated herein by reference in its entirety. The techniques of Cole et al. (1985, Monoclonal Antibodies and Cancer Therapy, ed. R. A. Reisfeld & S. Sell, pp. 77-96, New York, Alan R. Liss) and Boerder et al. (1991) J. Immunol, 147(1):86-95), are also available for the preparation of human monoclonal antibodies.

Human antibodies produced using other techniques but retaining the variable regions of the anti-A33 antibody of the present invention are included herein. Alternatively or additionally, human antibodies can also be produced using transgenic mice which are incapable of expressing functional endogenous mouse immunoglobulins, but which can express human immunoglobulin genes (e.g., see Lonberg and Huszar, 1995, Int. Rev. Immunol. 13:65-93; Taylor, L. D., et al., 1992, Nucl. Acids Res. 20:6287-6295; Kellermann S-A., and Green L. L., 2002, Current Opinion in Biotechnology 13:593-597; Little M. et al., 2000, Immunol. Today 21:364-370; Murphy, A. J. et al., 2014, Proc. Natl. Acad. Sci. U.S.A. 111(14):5153-5158). For a detailed discussion of this technology for producing human antibodies and human monoclonal antibodies and protocols for producing such antibodies, see, e.g., International Patent Application Publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,886,793; 5,916,771; 5,939,598; and 8,502,018, which are incorporated by reference herein in their entirety.

Still further, human monoclonal antibodies could be made by immunizing mice transplanted with human peripheral blood leukocytes, splenocytes or bone marrows (e.g., Trioma techniques of XTL). Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1988, Biotechnol. 12:899-903).

As used herein, an "anti-A33 antibody", "anti-A33 antibody portion," or "anti-A33 antibody fragment" and/or "anti-A33 antibody variant" and the like may, in some embodiments, refer to a polypeptide-containing entity that comprises at least a portion of an immunoglobulin that binds to A33, and in particular refers to an entity including a polypeptide that at least one complementarity determining region (CDR) of a heavy or light chain or a ligand binding portion thereof (and typically containing all CDRs found in a relevant chain or portion thereof) found in any of the particular monoclonal antibodies described herein that to A33. In some embodiments, the term refers to an entity that includes such a polypeptide that includes not only such CDRs, but also other sequences found in a heavy chain or light chain variable region, a heavy chain or light chain constant region, a framework region, or any portion thereof, of non-murine origin, preferably of human origin, which can be incorporated into an antibody of the present invention. In some particular embodiments, the term "anti-A33 antibody", as will be clear from context, is used to refer collectively or individually to huA33, hA33, A33, humanized antibody A33, humanized A33, and combinations thereof, and/or relevant fragments or components, domains, or regions thereof, such as single chain variable fragments (e.g., huA33 scFv, hA33 scFv, A33 scFv, and combinations thereof).

In some embodiments, a humanized antibody is capable of modulating, decreasing, antagonizing, mitigating, alleviating, blocking, inhibiting, abrogating and/or interfering with at least one cell function in vitro, in situ and/or in vivo, wherein said cell expresses human A33. As a non-limiting example, a suitable anti-A33 antibody, specified portion or variant binds with high affinity to an epitope, in particular a peptide epitope, of human A33.

Antibody fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')2 heavy chain portion can be designed to include DNA sequences encoding the $C_H1$ domain and/or hinge region of the heavy chain. Various portions of antibodies can be joined together chemically by conventional techniques, or can be prepared as a contiguous protein using genetic engineering techniques.

In some embodiments, chimeric or humanized antibodies for use in accordance with the present invention include those wherein the CDRs are found in one or more of the anti-A33 antibodies described herein and at least a portion, or the remainder of the antibody is found in or derived from one or more human antibodies. Thus, for example, in some embodiments, the human part of the antibody may include the framework, $C_L$, $C_H$ domains (e.g., $C_H1$, $C_H2$, $C_H3$), hinge, $V_L$, $V_H$ regions which are substantially non-immunogenic in humans. Those skilled in the art, reading the present disclosure, will appreciate that, in some embodiments, a "human part" of an antibody utilized as described herein, may in some embodiment may not show 100% identity with the corresponding sequence found in a relevant source human antibody. In some embodiments, as many of the human amino acid residues as possible found in the source human antibody are retained in order for the immunogenicity to be negligible, however, in various embodiments, the human residues may be modified as necessary or otherwise desired to support the antigen binding site formed by the CDRs while simultaneously maximizing the humanization of the antibody. Such changes or variations, in some embodiments, retain or reduce the immunogenicity in humans or other species relative to non-modified antibodies.

Those of ordinary skill in the art, reading the present disclosure, will appreciate that an antibody agent provided by the present invention, including one that is a humanized antibody and/or that utilizes a humanized antibody sequence elements as described herein, can be produced by a non-human animal or prokaryotic or eukaryotic cell that is capable of expressing functionally rearranged human immunoglobulin (e.g., heavy chain and/or light chain) genes. Further, when the antibody agent is a single chain antibody, it can comprise a linker peptide that is not found in native human antibodies. For example, an Fv can comprise a linker peptide, such as two to about twenty glycine or other amino acid residues, preferably 8-15 glycine or other amino acid residues, which connects the variable region of the heavy chain and the variable region of the light chain. Such linker peptides are considered to be of human origin.

Antibody humanization can be performed by, for example, by synthesizing a combinatorial library comprising the six CDRs of a non-human target monoclonal antibody fused in frame to a pool of individual human frameworks. A human framework library that contains genes representative of all known heavy and light chain human germline genes can be utilized. Resulting combinatorial libraries can be screened for binding to antigens of interest. Such an approach can allow for screening and/or selection of particularly favorable (e.g., in terms of maintaining the binding activity to the parental antibody) combinations of fully human frameworks. Humanized antibodies can then be further optimized by a variety of techniques.

Antibody humanization can be used to evolve mouse or other non-human antibodies into "fully human" antibodies. Resulting antibody(ies) may contain only human sequence and no mouse or non-human antibody sequence, while maintaining similar binding affinity and specificity as the starting antibody.

In some embodiments, anti-A33 humanized antibodies for use in accordance with the present invention comprise a variant Fc region, wherein said variant Fc region comprises at least one amino acid modification relative to a wild-type Fc region (or the parental Fc region), such that said molecule has an altered affinity for an Fc receptor (e.g., an FcγR), provided that said variant Fc region does not have a substitution at positions that make a direct contact with Fc receptor based on crystallographic and structural analysis of Fc-Fc receptor interactions such as those disclosed by Sondermann et al. (2000, Nature, 406:267-273, which is incorporated herein by reference in its entirety). Examples of positions within the Fc region that make a direct contact with an Fc receptor such as an FcγR are amino acids 234-239 (hinge region), amino acids 265-269 (B/C loop), amino acids 297-299 (C'/E loop), and amino acids 327-332 (F/G) loop. In some embodiments, the anti-A33 antibodies of the present invention comprising variant Fc regions comprise modification of at least one residue that makes a direct contact with an FcγR based on structural and crystallographic analysis.

In some embodiments, an anti-A33 antibody for use in accordance with the present invention is a humanized A33 antibody with an altered affinity for activating and/or inhibitory receptors, having variant Fc regions with one or more amino acid modifications, wherein said one or more amino acid modification is a substitution at position 297 with alanine; in some embodiments, a substitution at 239D, 330L, 332E to enhance FcR affinity; in some embodiments, a substitution at 322K to reduce or eliminate FcR binding. In some embodiments, anti-A33 antibodies for use in accordance with the present invention have an Fc region with variant glycosylation as compared to a parent Fc region; in some embodiments, variant glycosylation includes absence of fucose; in some embodiments, variant glycosylation results from expression in GnT1-deficient CHO cells. In some embodiments, the present invention provides bispecific binding agents having a humanized A33 antibody component that comprises a variant Fc region characterized by a K322A substitution. In some embodiments a provided bispecific binding agent includes an antibody component that shows variant glycosylation (e.g., is aglycosylated) as compared with a parent antibody from which the component may be derived; in some such embodiments, such a variant may be or comprise a variant Fc region characterized by the K322A substitution. In some embodiments, such variant components (e.g., variant Fc regions) result in a complete elimination of complement activation and FcR binding, which otherwise may damage tumor cell membrane prior to addition of a clearing agent in pre-targeted radioimmunotherapy as described herein.

In some embodiments, the present invention provides and/or utilizes antibodies or antibody agents comprising a variant Fc region (i.e., an Fc region includes one or more additions, deletions, and/or substitutions relative to an appropriate reference Fc) that is characterized in that its alter effector function altered and/or its affinity for an FcR is enhanced or diminished relative to the reference Fc. These variations are within the skill of a person in the art.

Therefore, among other things, the present invention provides multi-specific binding agents (e.g., antibody agents) comprising variant Fc regions that bind with a greater affinity to one or more FcγRs. Such agents preferably mediate effector function more effectively as discussed infra. In some embodiments, the present invention provides multi-specific binding agents (e.g., antibody agents) comprising a variant Fc region that bind with a weaker affinity to one or more FcγRs. Reduction or elimination of effector function is desirable in certain cases for example in the case of antibodies whose mechanism of action involves blocking or antagonism but not killing of the cells bearing a target antigen. Further, elimination of effector function is desirable, in some embodiments, when making bispecific antibodies as discussed infra. Reduction or elimination of effector function would be desirable in cases of autoimmune disease where one would block FcγR activating receptors in effector cells (This type of function would be present in the host cells). Generally, increased effector function may be directed to tumor and foreign cells; in some embodiments, effector function may be directed away from tumor cells.

Fc variants for use in accordance present invention may be combined with other Fc modifications, including but not limited to modifications that alter effector function. The invention encompasses combining an Fc variant as described herein with other Fc modifications to provide additive, synergistic, or novel properties in antibodies or Fc fusions. In some such embodiments, Fc variants may enhance the phenotype of the modification with which they are combined. For example, if an Fc variant is combined with a mutant known to bind FcγRIIIA with a higher affinity than a comparable molecule comprising a wild type Fc region, the combination with the mutant results in a greater fold enhancement in FcγRIIIA affinity.

In some embodiments, in accordance with the present invention Fc variants as described herein are incorporated into an antibody or Fc fusion to generate an engineered agent that comprises one or more Fc glycoforms (i.e., one or more Fc polypeptides to which one or more carbohydrates is covalently attached) to a molecule comprising an Fc region wherein the carbohydrate composition of the glycoform differs chemically from that of a parent molecule comprising an Fc region.

In some embodiments, a multi-specific binding agent (e.g., an antibody agent) as described herein may include an Fc variant that shows variant glycosylation and/or may be expressed in a glycosylation deficient cell line (e.g., a GnT1-deficient CHO cell) such an Fc region of the agent is produced lacking glycosylation as compared to an appropriate reference Fc region (e.g., a wild type), or an Fc region expressed in a cell line not deficient in glycosylation.

In some embodiments, antibodies utilized in accordance with the present invention, may have a modified glycosylation site relative to an appropriate reference antibody that binds to an antigen of interest (e.g., A33), preferably without altering the functionality of the antibody, e.g., binding activity to the antigen. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. For example, an Fc-glycoform (huA33-IgG1n) that lacks certain oligosaccharides including fucose and terminal N-acetylglucosamine may be produced in special CHO cells and exhibit enhanced ADCC effector function.

In some embodiments, the present invention encompasses methods of modifying the carbohydrate content of an antibody of the invention by adding or deleting a glycosylation site. Methods for modifying the carbohydrate content of antibodies are well known in the art and are included within the present invention, see, e.g., U.S. Pat. No. 6,218,149; EP0359096B1; U.S. Patent Publication No. US 2002/0028486; International Patent Application Publication WO 03/035835; U.S. Patent Publication No. 2003/0115614; U.S. Pat. Nos. 6,218,149; 6,472,511; all of which are incorporated herein by reference in their entirety. In some embodiments, the present invention includes methods of modifying the carbohydrate content of an antibody (or relevant portion or component thereof) by deleting one or more endogenous carbohydrate moieties of the antibody. In some certain embodiments, the present invention includes deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTIII), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al., 1999, Nat. Biotechnol. 17:176-180; Davies et al., 2001, Biotechnol. Bioeng. 74:288-294; Shields et al., 2002, J. Biol. Chem. 277:26733-26740; Shinkawa et al., 2003, J. Biol. Chem. 278:3466-3473; U.S. Pat. No. 6,602,684; U.S. patent application Ser. No. 10/277,370; U.S. patent application Ser. No. 10/113,929; International Patent Application Publications WO 00/61739A1; WO 01/292246A1; WO 02/311140A1; WO 02/30954A1; POTILLEGENT™ technology (Biowa, Inc. Princeton, N.J.); GLYCOMAB™ glycosylation engineering technology (GLYCART biotechnology AG, Zurich, Switzerland); each of which is incorporated herein by reference in its entirety. See, e.g., International Patent Application Publication WO 00/061739; EA01229125; U.S. Patent Application Publication No. 2003/0115614; Okazaki et al., 2004, JMB, 336:1239-49, each of which is incorporated herein by reference in its entirety.

Multivalent Binding Agents

As those skilled in the art are aware, a multivalent binding agent is a molecular entity or complex that includes binding components that bind specifically to two or more targets (e.g., epitopes). Such multivalent binding agents find a variety of uses in the art, including therapeutic uses. To give but one example, as those skilled in the art are aware, multivalent binding agents have been engineered to facilitate killing of tumor cells by directing (or recruiting) cytotoxic T cells to a tumor site. Examples of tumor antigens include, but are not limited to, alpha fetoprotein (AFP), CA15-3, CA27-29, CA19-9, CA-125, calretinin, carcinoembryonic antigen, CD34, CD99, CD117, chromogranin, cytokeratin, desmin, epithelial membrane protein (EMA), Factor VIII, CD31 FL1, glial fibrillary acidic protein (GFAP), gross cystic disease fluid protein (GCDFP-15), HMB-45, human chorionic gonadotropin (hCG), inhibin, keratin, CD45, a lymphocyte marker, MART-1 (Melan-A), Myo Dl, muscle-specific actin (MSA), neurofilament, neuron-specific enolase (NSE), placental alkaline phosphatase (PLAP), prostate-specific antigen, S100 protein, smooth muscle actin (SMA), synaptophysin, thyroglobulin, thyroid transcription factor-1, tumor M2-PK, and vimentin.

In some embodiments, multivalent binding agents for use in accordance with the present invention are bispecific binding agents. In many embodiments, such bispecific binding agents are capable of binding to tumor cells. In many embodiments, such bispecific binding agents are capable of binding to human colorectal cancer cells via an A33 antigen expressed in the tumor cell surface.

In some embodiments, multivalent binding agents (e.g., bispecific binding agents) provided by the present invention are or comprise antibody components. A variety of technologies are known in the art for designing, constructing, and/or producing multispecific binding agents comprising antibody components.

For example, multivalent binding agents have been constructed that either utilize the full immunoglobulin framework (e.g., IgG), single chain variable fragment (scFv), or combinations thereof. Bispecific binding agents composed of two scFv units in tandem has been shown to be a clinically successful bispecific antibody format. In the case of anti-tumor immunotherapy, bispecific binding agents that comprise two single chain variable fragments (scFvs) in tandem have been designed such that an scFv that binds a tumor antigen is linked with an scFv that engages T cells by binding CD3. In this way, T cells are recruited to a tumor site in the hope that they can mediate killing of the tumor cells making up the tumor by the cytotoxic properties that certain T cells have. An example of such a bispecific binding agent has been made that targets CD19 and CD3 for lymphoma (termed Bispecific T cell Engaging, or BiTE; e.g., see Dreier et al., 2003, J. Immunol. 170:4397-4402; Bargou et al., 2008, Science 321:974-977), which has been successful in preventing tumor growth in animal xenograft studies. In human studies, this bispecific binding agent demonstrated objective tumor response, including five partial and two complete remissions.

Exemplary bispecific binding agents include those with a first antibody component specific for a tumor antigen and a second antibody component specific for a small molecule hapten (e.g., DTPA, IMP288, DOTA, DOTA-Bn, DOTA-desferrioxamine, Biotin, fluorescein, or those disclosed in Goodwin, D. A. et al., 1994, Cancer Res. 54(22):5937-5946, herein incorporated by reference). Bispecific binding agents can be made, for example, by combining heavy chains and/or light chains that recognize different epitopes of the same or different antigen. In some embodiments, by molecular function, a bispecific binding agent binds one antigen (or epitope) on one of its two binding arms (one $V_H/V_L$ pair), and binds a different antigen (or epitope) on its second arm (a different $V_H/V_L$ pair). By this definition, a bispecific binding agent has two distinct antigen binding arms (in both specificity and CDR sequences), and is monovalent for each antigen to which it binds.

In some embodiments, bispecific binding agents of the present invention are characterized by the ability to bind simultaneously to two targets that are of different structure. In some embodiments, bispecific binding agents of the present invention have at least one component that specifically binds to, for example, a B-cell, T-cell, myeloid, plasma, or a mast cell antigen or epitope and at least one other component that specifically binds to a targetable conjugate that bears a therapeutic or diagnostic agent.

Bispecific binding agents (e.g., bispecific antibodies) of the present invention are based on the particular insight that certain formats may be more beneficial for certain targets (e.g., a tumor antigen) when employed in multi-step pretargeted radioimmunotherapy (PRIT) methodology that targets human A33 antigen. For example, bispecific antibodies provided herein utilize a combination of a full IgG and an scFv. Such bispecific antibodies demonstrate bivalent binding via the IgG component (e.g., anti-A33) and bivalent binding via the scFv component (e.g., anti-DOTA-Bn). As described herein, bispecific antibodies having this format first bind to an A33-positive tumor cell via the IgG component (e.g., anti-A33) and excess antibody is cleared from the blood via a clearing agent (CA; e.g., a dextran-based clearing agent). This is followed by a step that includes the use of a radiolabeled small molecule hapten (e.g., $^{177}$Lu-DOTA-Bn). Exemplary radiolabeled small molecules include radiolanthanides, e.g., yttrium and lutetium (e.g., $^{86}$Y, $^{90}$Y and $^{177}$Lu) as well as $^{124}$I and $^{131}$I. Further, bispecific antibodies of the present invention provide both diagnostic and therapeutic tumor targeting features.

In various embodiments, a bispecific binding agent (e.g., a bispecific antibody) according to the present invention is composed of a first binding component and a second binding component. In many embodiments, first and second binding components of a bispecific binding agent as described herein are each composed of antibody components characterized by different specificities. In many embodiments, antibody components are selected from Table 8.

In various embodiments, a bispecific binding agent according to the present invention comprises a first binding component, a second binding component. In various embodiments, a bispecific binding agent according to the present invention comprises a first binding component, a second binding component and a linker that is connected to both the first and second binding component (e.g., positioned between the first and second binding components).

In various embodiments, first and/or second binding components as described herein comprise or are antibody components. In various embodiments, first and/or second binding components as described herein comprise a linker sequence.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second binding components). In some embodiments, a linker is employed in a bispecific binding agent described herein based on specific properties imparted to the bispecific binding agent such as, for example, a reduction in aggregation and/or an increase in stability. In some embodiments, a bispecific binding agent of the present invention comprises a $G_4S$ linker. In some certain embodiments, a bispecific binding agent of the present invention comprises a (GIS)$_n$ linker, wherein n is 1, 2, 3, 4, 5, 6, 7, 8, 9, 10, 11, 12, 13, 14, 15 or more.

In various embodiments, first and/or second binding components as described herein comprise or are immunoglobulins (e.g., IgGs). In various embodiments, first and/or second binding components binding components as described herein comprise or are antibody fragments (e.g., scFvs). In various embodiments, first binding components as described herein comprise or are immunoglobulins and second binding components comprise or are antibody fragments. In some certain embodiments, first binding components are immunoglobulins and second binding components are antibody fragments. In some certain embodiments, first binding components are IgGs and second binding components are scFvs.

In some certain embodiments, a bispecific binding agent according to the present invention comprises an immunoglobulin, which immunoglobulin comprises a heavy chain and a light chain, and an scFv. In some certain embodiments, scFvs are linked to the C-terminal end of the heavy chain of the immunoglobulin. In some certain embodiments, scFvs are linked to the C-terminal end of the light chain of the immunoglobulin. In various embodiments, scFvs are linked to heavy or light chains via a linker sequence.

In some embodiments, a bispecific binding agent of the present invention comprises one or more sequences that are at least about 50% (e.g., at least about 55%, 60%, 65%, 70%, 75%, 80%, 85%, 90%, 95%, 96%, 97%, 98%, or 99%) identical to one or more sequences that appear in Table 8.

In some embodiments, a bispecific binding agent of the present invention comprises one or more sequences that are substantially identical to one or more sequences that appears in Table 8.

In some embodiments, a bispecific binding agent of the present invention comprises one or more sequences that are identical to one or more sequences that appears in Table 8.

In some embodiments, a bispecific binding agent of the present invention is selected from one or more sequences that appear in Table 8. In some certain embodiments, a bispecific binding agent of the present invention is selected from two sequences that appear in Table 8, for example, a heavy chain and a light chain sequence.

In various embodiments, a first binding component of a bispecific binding agent as described herein comprises an antibody component having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an antibody component that appears in Table 8.

In various embodiments, a first binding component of a bispecific binding agent as described herein comprises an antibody component having a sequence that is substantially identical to an antibody component that appears in Table 8.

In various embodiments, a first binding component of a bispecific binding agent as described herein comprises an antibody component having a sequence that is identical to an antibody component that appears in Table 8.

In various embodiments, a second binding component of a bispecific binding agent as described herein comprises an antibody component having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an antibody component that appears in Table 8.

In various embodiments, a second binding component of a bispecific binding agent as described herein comprises an antibody component having a sequence that is substantially identical to an antibody component that appears in Table 8.

In various embodiments, a second binding component of a bispecific binding agent as described herein comprises an antibody component having a sequence that is identical to an antibody component that appears in Table 8.

As described herein, the present inventors provide an improved multi-step PRIT method in immunocompromised mice bearing s.c. A33-positive human colorectal tumors (SW1222) using a bispecific antibody termed huA33-C825. Such methodology includes i.v. injection of various doses of huA33-C825 and a dextran-based CA, followed with injection of $^{177}$Lu-DOTA-Bn theranostic (i.e., diagnostic and therapeutic) hapten for simultaneous scintigraphic imaging and radioimmunotherapy. The present invention specifically describes biodistribution studies that provide optimum huA33-C825 and CA doses, followed with a series of additional biodistribution studies to determine the tumor uptake as a function of $^{177}$Lu-DOTA-Bn doses (~2.0-111.0 MBq) to serve as a practical and dosimetric guide for PRIT studies. Also, as described herein, tumors and kidneys were excised at 24 hours post injection of $^{177}$Lu-DOTA-Bn at three different dose levels (11.1, 55.0, and 111.0 MBq) to examine ex vivo the $^{177}$Lu-activity microdistribution via autoradiography, as well as correlate the $^{177}$Lu-activity with the xenograft and tissue morphology via hematoxylin and eosin staining. Further, the estimated absolute SW1222 tumor uptake of huA33-C825 24 h p.i. of 0.25 mg/mouse based on radioactive tracer studies with $^{131}$I-huA33-C825 was ~90 pmol/g of tumor. Therefore, the present invention demonstrates that if a single huA33-C825 molecule has the capacity to bind two molecules of $^{177}$Lu-DOTA-Bn (thus maximum $^{177}$Lu-DOTA-Bn binding capacity of 180 pmol/g tumor), the estimated maximum occupancy is (11 pmol $^{177}$Lu-DOTA-Bn/180 pmol=0.061 or ~6%). Thus, the present invention specifically demonstrates that the improved PRIT method was effective without any associated adverse radiation response. Further, the present invention specifically demonstrates that, at least in some embodiments, immunocompromised mice with established s.c. human colorectal xenografts of could be cured with minimal toxicity to normal tissues including bone marrow and kidney using an improved multi-step PRIT method employing an anti-A33/anti-DOTA-Bn (metal) bispecific antibody termed huA33-C825, a dextran-based CA, and $^{177}$Lu-DOTA-Bn.

SW1222 stands out among commonly investigated human colorectal carcinomas (e.g., LS174T) as a relatively well-differentiated and vascularized tumor. While permitting homogeneous distribution of targeted antibodies (Emir et al., 2007, Cancer Res. 15; 67(24):11896-11905), these tumors are also relatively radioresistant. As described herein, the A33 antigen is highly expressed in more than 95% of human colon cancers with restricted normal expression and minimal shedding into circulation. There has been no successful clinical therapeutic targeting of the A33 antigen in human colorectal cancer. Bispecific antibodies as described herein demonstrate affinity to A33 and a DOTA-Bn (metal), which facilitates tumor uptake of a radiolabeled lutetium (e.g., $^{177}$Lu) and successful delivery of targeted radioimmunotherapy to A33-positive tumors. Also, bispecific binding proteins employing humanized A33 antibodies as described herein are capable of bivalent binding to A33 and bivalent binding to DOTA-Bn which results in enhanced potency for killing A33$^+$ tumors and increased safety from a lack of catastrophic radiation response. As such, the PRIT strategy employing the format of the bispecific binding proteins described herein represents a unique approach for enhanced tumor killing, reduced adverse effects, and demonstrates a potent therapeutic for the treatment of several A33-positive cancers.

Targets

Among other things, the present invention encompasses the recognition that multispecific binding agents, and particularly bispecific binding agents such as bispecific antibodies, are particularly useful and/or effective to facilitate cell killing. In particular, the present invention demonstrates that activity of multivalent binding agents that bind specifically to both a target-cell-associated epitope (e.g., a tumor antigen) and a small molecule hapten (e.g., a DOTA-Bn [metal]) can be an effective immunotherapy for colon cancers.

For example, in some embodiments of the present invention, a multivalent binding agent binds specifically to a tumor-cell-associated epitope and a small molecule hapten. In accordance with such embodiments, the multivalent binding agent can facilitate binding of the agent to one or both of its target epitopes and/or can enhance killing of the target tumor cell as mediated by radioimmunotherapy via the small molecule hapten.

In some embodiments, target cells to be killed include, for example, cells that express a tumor antigen (e.g., a A33-positive tumor). Those of ordinary skill in the art will be aware of appropriate target epitopes on such cells to which multivalent binding agents as described herein desirably bind.

Nucleic Acid Construction and Expression

Humanized antibodies and multispecific binding agents (e.g., bispecific antibodies) as described herein may be produced from nucleic acid molecules using molecular biological methods known to the art. Nucleic acid molecules are inserted into a vector that is able to express the fusion proteins in when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the present invention under control of transcriptional/translational control signals. These methods may include in vitro recombinant DNA and synthetic techniques and in vivo recombination (See Sambrook et al. Molecular Cloning, A Laboratory Manual, Cold Spring Harbor Laboratory; Current Protocols in Molecular Biology, Eds. Ausubel, et al, Greene Publ. Assoc., Wiley-Interscience, NY).

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element that are known in the art.

Nucleic acid constructs include regions that encode multispecific binding proteins generated from antibodies and/or antibody components. Typically, such multispecific binding proteins will be generated from $V_H$ and/or $V_L$ regions. After identification and selection of antibodies exhibiting desired binding and/or functional properties, variable regions of each antibody are isolated, amplified, cloned and sequenced. Modifications may be made to the $V_H$ and $V_L$ nucleotide sequences, including additions of nucleotide sequences encoding amino acids and/or carrying restriction sites, deletions of nucleotide sequences encoding amino acids, or substitutions of nucleotide sequences encoding amino acids. The antibodies and/or antibody components may be generated from human, humanized or chimeric antibodies.

Nucleic acid constructs of the present invention are inserted into an expression vector or viral vector by methods known to the art, and nucleic acid molecules are operatively linked to an expression control sequence.

Where appropriate, nucleic acid sequences that encode humanized antibodies and multi-specific binding agents as described herein may be modified to include codons that are optimized for expression in a particular cell type or organism (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding antibody components, in whole or in part, may include an altered sequence to optimize codon usage for a particular cell type (e.g., a eukaryotic or prokaryotic cell).

For example, the coding sequence for a humanized heavy (or light) chain variable region as described herein may be optimized for expression in a bacterial cells. Alternatively, the coding sequence may be optimized for expression in a mammalian cell (e.g., a CHO). Such a sequence may be described as a codon-optimized sequence.

An expression vector containing a nucleic acid molecule is transformed into a suitable host cell to allow for production of the protein encoded by the nucleic acid constructs. Exemplary host cells include prokaryotes (e.g., E. coli) and eukaryotes (e.g., a COS or CHO cell). Host cells transformed with an expression vector are grown under conditions permitting production of a humanized antibody or multispecific binding agent of the present invention followed by recovery of the humanized antibody or multispecific binding agent.

Humanized antibodies and/or multispecific binding agents of the present invention may be purified by any technique, which allows for the subsequent formation of a stable antibody or binding agent molecule. For example, not wishing to be bound by theory, antibodies and/or multispecific binding agents may be recovered from cells either as soluble polypeptides or as inclusion bodies, from which they may be extracted quantitatively by 8M guanidinium hydrochloride and dialysis. In order to further purify antibodies and/or multispecific binding agents of the present invention, conventional ion exchange chromatography, hydrophobic interaction chromatography, reverse phase chromatography or gel filtration may be used. Humanized antibodies and/or multispecific binding agents of the present invention may also be recovered from conditioned media following secretion from eukaryotic or prokaryotic cells.

Screening and Detection Methods

Humanized antibodies and/or multispecific binding agents of the present invention may also be used in in vitro or in vivo screening methods where it is desirable to detect and/or measure one or more activities of a cell or cells (e.g., apoptosis or cell growth). Screening methods are well known to the art and include cell-free, cell-based, and animal assays. In vitro assays can be either solid state or soluble target molecule detection may be achieved in a number of ways known to the art, including the use of a label or detectable group capable of identifying a humanized antibody or a multispecific binding agent which is bound to a target molecule (e.g., cell surface antigen). Detectable labels may be used in conjunction with assays using humanized antibodies or multispecific binding agents of the present invention.

Therapeutic Agents

Humanized antibodies and/or multivalent binding agents of the present invention may be utilized as therapeutic agents. In some embodiments, as will be understood in the art, they are utilized without further modification. In some embodiments, they may be incorporated into a composition or formulation as described herein. In some embodiments, they may be chemically associated or linked (e.g., conjugated) with one or more other agents or entities, e.g., with a payload.

A variety of technologies for conjugating antibody agents, or components thereof, with other moieties or entities are well known in the art and may be utilized in accordance with the practice of the present invention. To give but one example, radioactively-labeled antibody agents may be produced according to well-known technologies in the art.

For instance, monoclonal antibodies can be iodinated by contact with sodium and/or potassium iodide and a chemical oxidizing agent such as sodium hypochlorite, or an enzymatic oxidizing agent, such as lactoperoxidase. Antibody agents may be labeled with technetium-99m by ligand exchange process, for example, by reducing pertechnate with stannous solution, chelating the reduced technetium onto a Sephadex column and applying the antibody to this column. In some embodiments, provided antibody agents are labeled using direct labeling techniques, e.g., by incubating pertechnate, a reducing agent such as SNC12, a buffer solution such as sodium-potassium phthalate solution, and the antibody. Intermediary functional groups which are often used to bind radioisotopes which exist as metallic ions to antibody are diethylenetriaminepentaacetic acid (DTPA), or ethylene diaminetetracetic acid (EDTA), or 1,4,7,10-tetraazacyclododecane-1,4,7,10-tetraacetic acid (DOTA), or p-aminobenzyl-DOTA (DOTA-Bn). Radioactive isotopes may be detected by, for example, dosimetry.

Therapeutic Methods

The ability of humanized antibodies and/or multi-specific binding agents of the present invention to exhibit high affinity binding for one of the target antigens makes them therapeutically useful for efficiently targeting cells expressing the target antigen. Thus, it some embodiments, it may be desirable to increase the affinity of a humanized antibody or multi-specific binding agent for one target antigen and not the other target antigen that is also bound by the multi-specific binding agent (or an Fc receptor in the case of a humanized antibody). For example, in the context of tumor killing, certain conditions may benefit from an increase or decrease in affinity to a tumor antigen but not to a second antigen. Thus, it may be beneficial to increase the binding affinity of a humanized antibody or multi-specific binding agent to a tumor antigen in a patient having a tumor that expresses the tumor antigen through the use of a humanized antibody or multi-specific binding agent as described herein.

The present invention provides a humanized antibody and/or multi-specific binding agent as described herein as a therapeutic for the treatment of patients having a tumor that expresses an antigen that is capable of being bound by such a multi-specific binding agent. Such humanized antibodies and/or multi-specific binding agents may be used in a method of treatment of the human or animal body, or in a method of diagnosis.

Administration

The present invention provides methods of administering an effective amount of a therapeutic active described herein (e.g., a humanized antibody or multi-specific binding agent) to a subject in need of treatment.

Humanized antibodies or multi-specific binding agents as described herein may be administered through various methods known in the art for the therapeutic delivery of agents, such as proteins or nucleic acids can be used for the therapeutic delivery of a humanized antibody or multi-specific binding agent or a nucleic acid encoding a humanized antibody or multi-specific binding agent of the present invention for killing or inhibiting growth of target cells in a subject, e.g., cellular transfection, gene therapy, direct administration with a delivery vehicle or pharmaceutically acceptable carrier, indirect delivery by providing recombinant cells comprising a nucleic acid encoding a multi-specific binding agent of the present invention.

Various delivery systems are known and can be used to administer a humanized antibody or multi-specific binding agent of the present invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Routes of administration can be enteral or parenteral and include, but are not limited to, intravenous, subcutaneous, intramuscular, parenteral, transdermal, or transmucosal (e.g., oral or nasal). In some embodiments, multi-specific binding agents of the present invention are administered intravenously. In some embodiments, multispecific binding agents of the present invention are administered subcutaneously. In some embodiments, multi-specific binding agents are administered together with other biologically active agents.

Those of ordinary skill in the art, reading the present disclosure, will readily appreciate that therapy with a therapeutic active described herein (e.g., with a humanized antibody or multi-specific binding agent), as described herein, may in certain embodiments be combined with other therapies, and particularly including other anti-tumor therapies. In some embodiments, such other anti-tumor therapies may be or comprise, for example administration of one or more chemotherapeutic agents, immunomodulatory agents, radiation therapy, high-frequency ultrasound therapy, surgery, etc.

In some embodiments, relative timing of administration of a therapeutic active described herein (e.g., a humanized antibody or multi-specific binding agent) and another therapy with which it is combined may be selected to optimize effect.

To give but a few examples, in some embodiments, a therapeutic active as described herein is administered under conditions and for a period of time (e.g., according to a dosing regimen) sufficient for it to saturate tumor cells. In some embodiments, unbound therapeutic active is removed from the blood stream after administration; in some such embodiments, such removal occurs (e.g., is permitted to occur) prior to administration of another agent.

In some particular embodiments, a therapeutic active as described herein is administered in combination with another agent that targets DOTA-Bn. In some such embodiments, the another agent carries a payload. In some embodiments, the payload may be or comprise a therapeutic agent payload (e.g., a toxic payload). In some embodiments the payload may be or comprise a detection agent payload.

In some particular embodiments, a therapeutic active described herein (e.g., a humanized antibody or multi-specific binding agent) as described herein is administered so that tumor cells are saturated, and subsequently a second agent, that targets DOTA-Bn (and may carry a payload) is administered. Optionally, at least one third agent that targets DOTA-Bn (e.g., and may carry a different payload) is administered.

In some embodiments, second and, optionally, third agents are administered a period of time after administration of a therapeutic active described herein, which period of time may be sufficient to permit clearance of unbound therapeutic agent. In some embodiments, second and, optionally third agents are administered without further administration of the therapeutic agent. For example, in some embodiments, a therapeutic active as described herein is administered according to a regimen that includes at least one cycle of: (i) administration of the therapeutic agent (optionally so that relevant tumor cells are saturated); (ii) administration of a second and, optionally at least one third agent (e.g., that targets DOTA-Bn, and may optionally carry a payload); (iii) optional additional administration of the second and/or third agents, without additional administration of the therapeutic agent. In some embodiments, a therapeutic regimen may comprise multiple such cycles; in some embodiments, a regimen may comprise 1, 2, 3, 4, 5, 6, 7, 8, 9, 10 or more cycles.

In some embodiments, a therapeutic regimen comprises only a single cycle that includes administration of the therapeutic agent; in some embodiments such a therapeutic regimen may comprise one or more cycles that include steps (ii) and, optionally, (iii) but do not include additional administrations of the therapeutic agent.

In some embodiments, prior administration of a therapeutic agent as described herein permits combination therapy in which the agent with which the therapeutic agent is combined shows a broader therapeutic index than it does when administered alone (i.e., without the prior administration of a therapeutic agent as described herein). In some embodiments, such a broader therapeutic index is at least a log fold improved.

Pharmaceutical Compositions

The present invention further provides pharmaceutical compositions comprising humanized antibodies or multi-specific binding agents of the present invention and a pharmaceutically acceptable carrier or excipient. The composition, if desired, can also contain one or more additional therapeutically active substances.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

A pharmaceutical composition in accordance with the present invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by the United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

General considerations in the formulation and/or manufacture of pharmaceutical agents may be found, for example, in Remington: The Science and Practice of Pharmacy 21st ed., Lippincott Williams & Wilkins, 2005 (incorporated herein by reference).

Kits

The present invention further provides a pharmaceutical pack or kit comprising one or more containers filled with at least one humanized antibody or multi-specific binding agent (e.g., a bispecific antibody) as described herein. Kits may be used in any applicable method, including, for example, therapeutically or diagnostically. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Other features of the invention will become apparent in the course of the following descriptions of exemplary embodiments, which are given for illustration of the invention and are not intended to be limiting thereof.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. In Vitro Characterization of huA33-C825

Among other things, the present invention encompasses the insight that the humanized antibody A33 (huA33) was of particular interest for constructing multi-specific binding agents (e.g., a bispecific antibody). Without wishing to be bound by any particular theory, the present inventors proposed that suboptimal tumor dose and therapeutic index observed for radiolabeled monospecific huA33 (e.g., $^{131}$I-huA33) could be overcome by employing huA33 in a multi-specific format.

This Example describes production of bispecific antibodies composed of a first antigen-binding site based on humanized antibody A33 and a second antigen-binding site that binds to a small molecule hapten (e.g., benzyl-1,4,7,10-tetraazacyclododecane-1,4,7,10-tetraacetic acid [DOTA-Bn]). The data presented herein describes the successful production of bispecific antibodies (termed huA33-C825) to target colorectal cancer cells. As described herein, an anti-DOTA-Bn single chain Fv fragment (ScFv) based on a affinity matured 2D12.5 antibody was linked to the carboxyl end of a humanized A33 light chain. A major drawback in the development of antibody agents for pretargeted radio-immunotherapy (PRIT) has been radiation overexposure in normal tissues, immunogenicity, suboptimal tumor dose and a low therapeutic index. As demonstrated below, bispecific antibodies of the present invention overcome such deficiencies and provide for effective PRIT possibilities for cancers expressing the human A33 antigen such as colorectal cancer.

Exemplary biochemical purity analysis of huA33-C825 by SE-HPLC is set forth in FIG. 1. SE-HPLC showed a major peak (90% by UV analysis) with an approximate MW of 210 KDa, as well as some minor peaks assumed to be aggregates removable by gel filtration. The bispecific antibody remained stable by SE-HPLC and Biacore after multiple freeze and thaw cycles. Binding affinity was measured by Biacore T100. Exemplary results are set forth in Table 3. Exemplary sensorgrams are set forth in FIG. 2.

TABLE 3

| Antigen | Agent | $k_{on}$ (1/Ms) | $k_{off}$ (1/s) | $K_D$ (M) |
|---|---|---|---|---|
| Human A33 | huA33-IgG1 | 6.14E+05 | 1.05E−03 | 1.71E−09 |
|  | huA33-C825 | 9.15E+04 | 5.81E−03 | 6.35E−08 |
| BSA-DOTA-Bn(Y) | hu3F8-C825 | 1.60E+04 | 3.37E−04 | 2.12E−08 |
|  | huA33-C825 | 1.90E+04 | 2.20E−04 | 1.16E−08 |

Figure 2A:
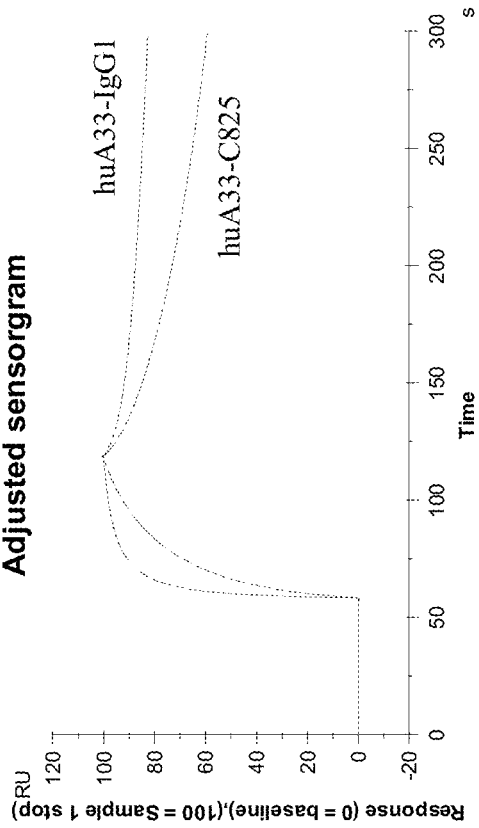
FIGS. 2A-2B show exemplary Biacore sensorgrams of antibody binding to (FIG. 2A) human A33 antigen and (FIG. 2B) BSA-(Y)-DOTA-Bn.
Figure 2B:
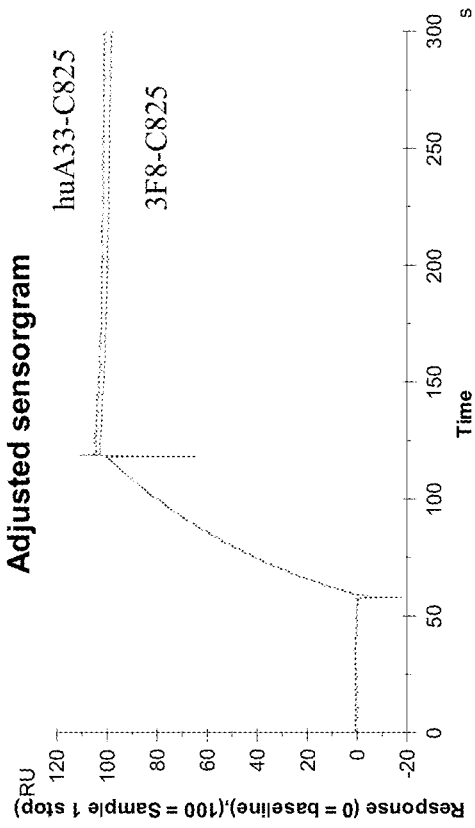
Figures 3A, 3B:
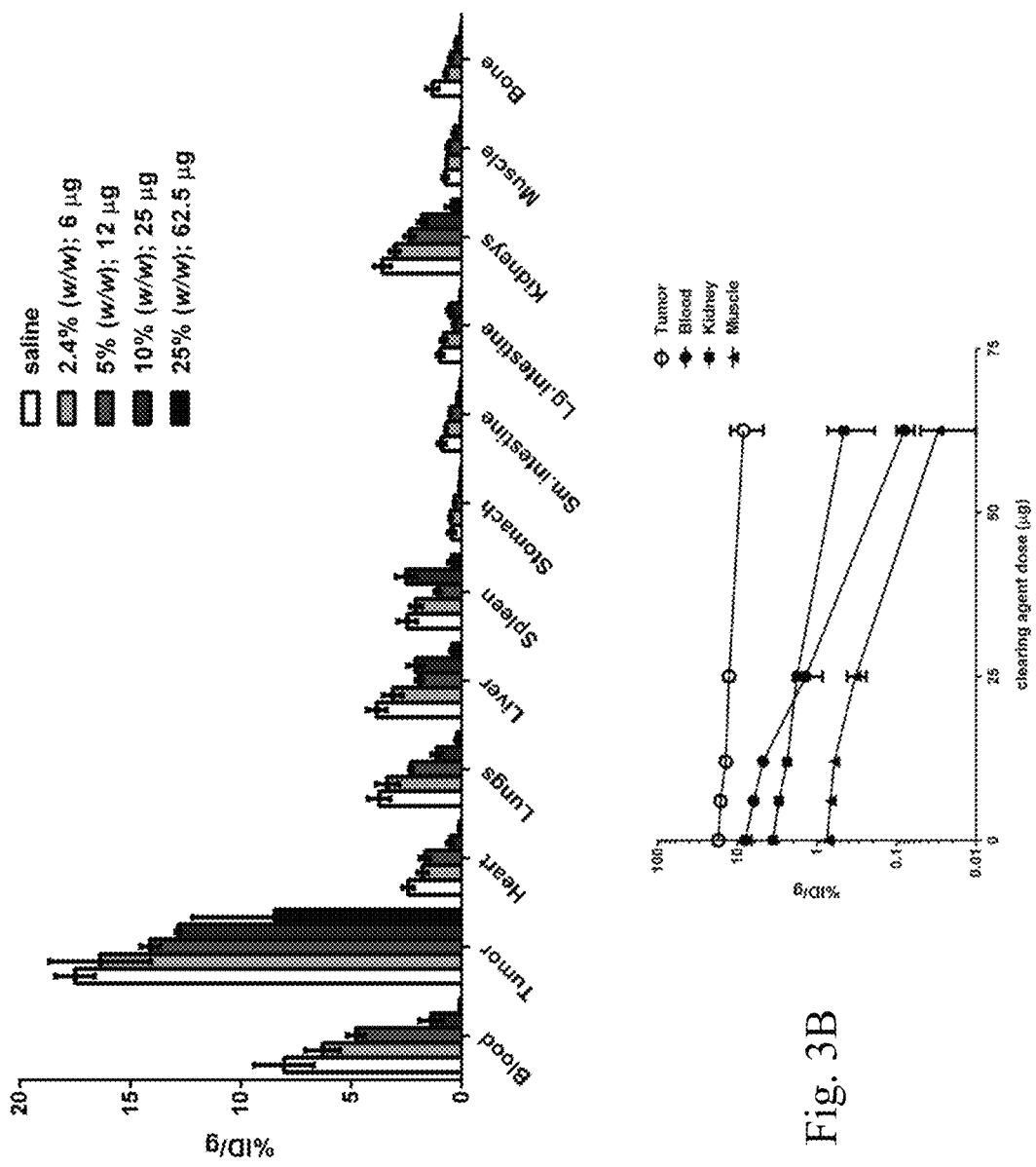
FIGS. 3A-3D show exemplary (FIG. 3A) activity of Lutetium-177 for tumor and various normal tissues among different doses of clearing agent (CA) and control (saline), (FIG. 3B) activity of Lutetium-177 at various concentrations of CA, (FIG. 3C) tumor-to-organ ratios at various concentrations of CA, and (FIG. 3D) activity of Lutetium-177 at hours post injection. Activity is expressed as percent injected dose per gram tissue (% ID/g). There is prolonged retention in the tumor over multiple hours and rapid clearance from other tissues.
Figure 3C:
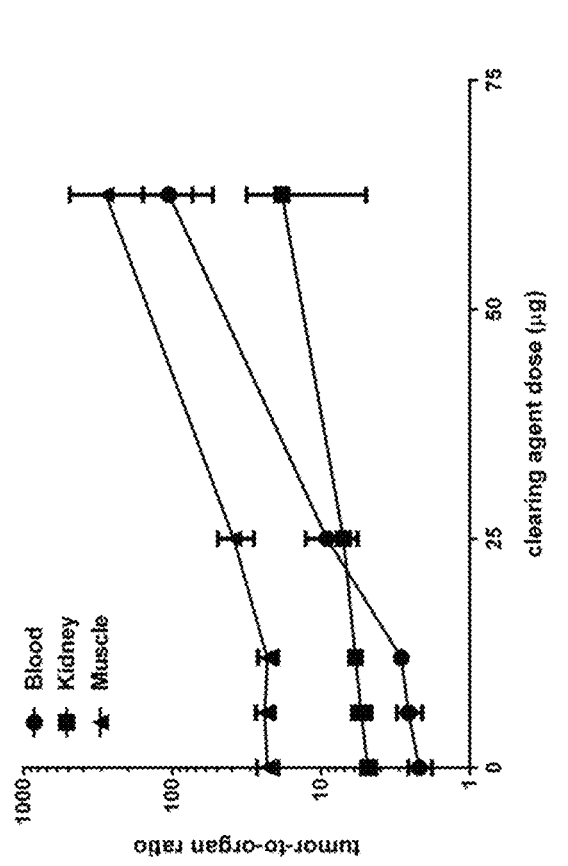
Figure 3D:
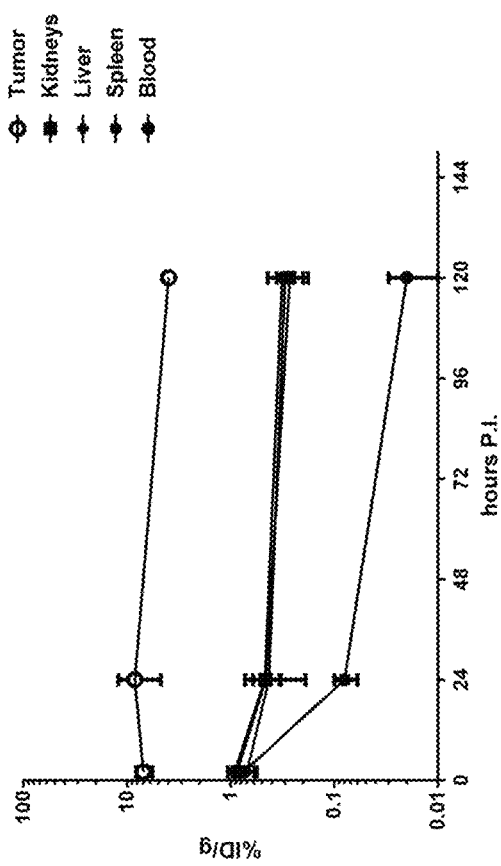

As shown in this Example, huA33-C825 demonstrated a lower affinity for the human A33 antigen as compared to the monospecific huA33 antibody ($K_D$ of 63.5 nM v. 1.71 nM, FIG. 2A). HuA33-C825 retained high binding affinity for BSA-(Y)-DOTA-Bn ($K_D$ of 11.6 nM) as compared to a control bispecific antibody having a first antigen-binding site that does not bind the A33 antigen and a second antigen-binding site that binds DOTA-Bn (metal) ($K_D$ of 21.2 nM, FIG. 2B). Taken together, this Example demonstrates the construction of a bispecific antibody that binds the human A33 antigen and a small-molecule hapten (e.g., DOTA-Bn) that retains high affinity for both targets. Further, the reduction in affinity to the human A33 antigen observed in huA33-C825 provides for a faster clearance as compared to parental huA33-IgG1 antibody.

Example 2. Optimization of PRIT with huA33-C825, Dextran-Clearing Agent (Dextran-CA) and $^{177}$Lu-DOTA-Bn This Example demonstrates the efficacy of a multi-specific binding agent (e.g., a bispecific antibody) for pretargeted radioimmunotherapy (PRIT) for A33-positive tumors. In particular, this Example describes the optimization of tumor targeting in a pretargeted radioimmunotherapy (PRIT) protocol in SW1222-tumor bearing rodents employing the bispecific antibody described in Example 1 as a function of the amount of a clearing agent (CA). As shown below, with increasing doses a progressive increase in therapeutic index is observed, but also a reduction in absolute tumor uptake.

A 0.25 mg/mouse dose of huA33-C825 was selected based on pilot biodistribution studies in SW1222-tumor bearing mice at 24 h p.i. of $^{177}$Lu-DOTA-Bn using 0.1-0.6 mg of huA33-C825 (0.48-2.86 nmol), and fixed ratios of CA and $^{177}$Lu-DOTA-Bn (5.6 MBq), showing a plateau of ~15-18% ID/g for the $^{177}$Lu-activity concentration in tumor at 0.25-0.6 mg huA33-C825. Next, additional biodistribution experiments were performed to optimize the CA dose during PRIT with 0.25 mg (1.19 nmol) as the huA33-C825 dose. Groups of tumor-bearing mice (n=3 to 4 per group) with were injected with huA33-C825, followed 24 h later with either: saline (i.e. vehicle), 2.4% (w/w, with respect to 0.25 mg huA33-C825 dose), 5% (w/w), 10% (w/w), or 25% (w/w) CA doses (0-62.5 µg/mouse). After an additional 4 h, mice were injected with 5.6 MBq of $^{177}$Lu-DOTA-Bn, and sacrificed 24 h later for biodistribution analysis. Exemplary optimization of clearing agent is shown in FIGS. 3A-3D. Exemplary $^{177}$Lu-DOTA-Bn activities in SW1222 tumor and various normal tissues for the groups of mice given 25% (w/w) dose of CA is shown in FIGS. 4A-4D.

Figure 4A:
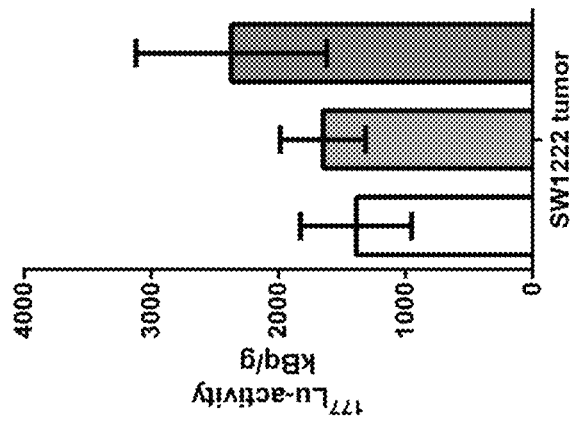
FIGS. 4A-4D show exemplary tumor uptake of $^{177}$Lu-DOTA-Bn at 24 hours post injection as a function of radioactivity in the treatment of mice bearing a human colon cancer xenograft (SW1222)
Figure 4B:
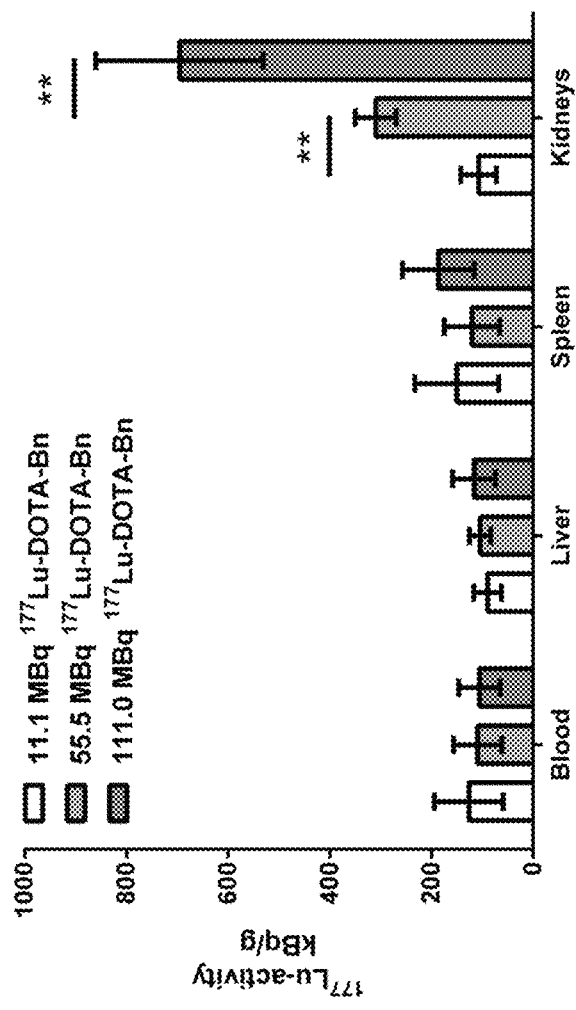
Figure 4C:
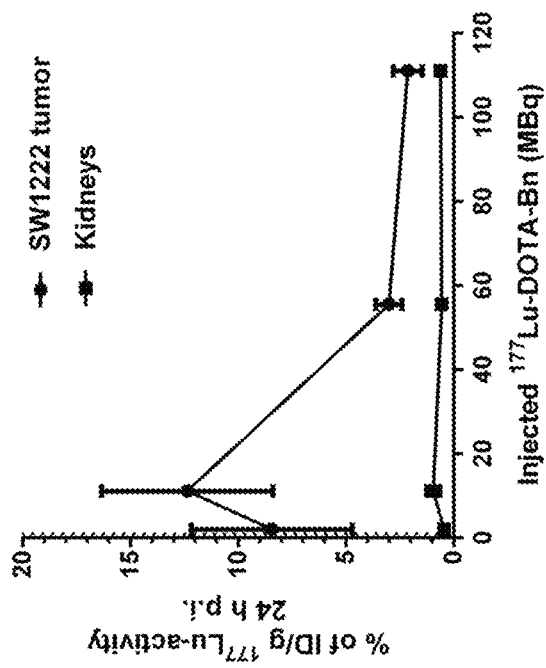
Figure 4D:
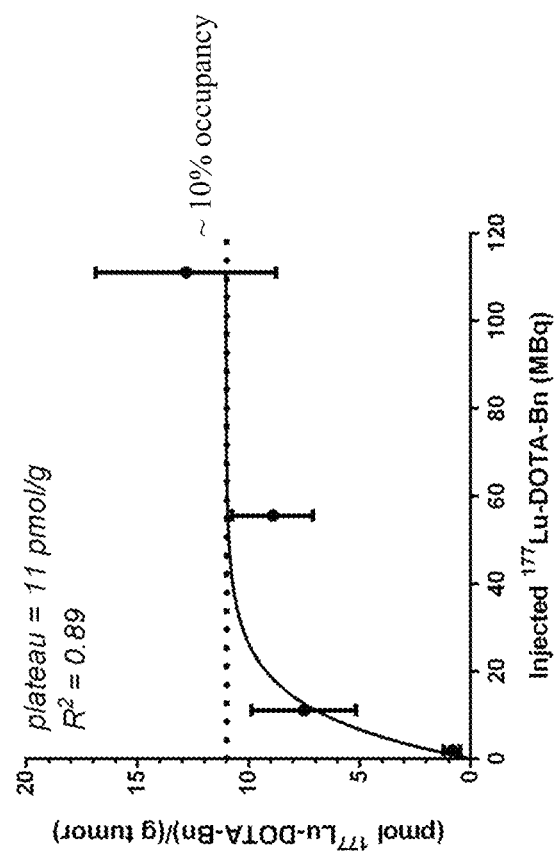

As expected, the CA dose had a significant impact on the circulating (i.e., blood) $^{177}$Lu-activity (from ~8 to 0.1% ID/g for saline (no CA) to 25% (w/w), respectively). In addition, the CA dose appeared to reduce the capacity for subsequent $^{177}$Lu-DOTA-Bn uptake at the tumor. The highest CA dose tested (25% (w/w)) was considered optimum since the tumor-to-normal organ ratios for the tissues with the highest radiosensitivity (blood and kidney) were highest compared to lower CA doses, although at the expense of a reduction in the $^{177}$Lu-DOTA-Bn tumor uptake compared with PRIT with saline (~50% less uptake). Specifically, the tumor uptake (as % ID/g, average±standard error of the mean) of $^{177}$Lu-DOTA-Bn was 17.51±0.90 (n=3) and 8.46±3.74 (n=4), for saline and at the 65 µg dose level (25% (w/w)) for CA, respectively. For saline, the tumor-to-organ ratios for blood, kidney, and muscle were 2.2±0.4, 4.9±0.6, and 23.2±3.8, respectively. At the 65 µg CA dose level (25% (w/w)) for CA, the tumor-to organ ratios for blood, kidney, and muscle were 105.8±52.3, 18.4±13.4, and 282.1±208.7, respectively. Next, $^{177}$Lu-DOTA-Bn dose titration studies were performed using the optimized PRIT doses for huA33-C825 and CA. For $^{177}$Lu-DOTA-Bn dose titration studies, the $^{177}$Lu-activity biodistribution data for tumor and critical select tissues (blood, liver, spleen, and kidneys) was compared between $^{177}$Lu-DOTA-Bn dose groups as both % ID/g and absolute uptake (kBq/g; see FIGS. 4A, 4B). Finally, a single-time point biodistribution experiment at 24 h p.i. of $^{131}$I-trace labeled huA33-C825 (0.39-0.40 MBq with cold huA33-C825 added to 1.19 nmol) was performed in SW1222-tumor bearing mice to estimate the absolute antibody uptake of huA33-C825 in tumor (as pmol/g) during PRIT. Exemplary tabulated values are set forth in Table 4 (data is presented as mean±SD). Exemplary tumor uptake calculations are shown in FIG. 4D.

As shown in this Example, the $^{131}$I-huA33-C825 uptake in tumor (average±standard deviation) was 3.71±0.97% ID/g. This corresponds to an absolute huA33-C825 uptake of 44 pmol/g (taking into account ~50% immunoreactive fraction, then 88 pmol/g).

TABLE 4

Biodistribution study at 24 h p.i. following i.v. injection of $^{131}$I-A33-C825 (0.39-0.40 MBq, 0.25 mg/1.19 nmol) into SW1222 tumor-bearing mice (n = 5).

| Tissues | 24 hr |
|---|---|
| Blood | 5.05 ± 0.97 |
| Heart | 2.10 ± 0.31 |
| Lungs | 2.35 ± 0.52 |
| Liver | 2.04 ± 0.53 |
| Spleen | 1.36 ± 0.30 |
| Stomach | 6.92 ± 3.06 |
| Small Intestine | 0.98 ± 0.35 |
| Large Intestine | 0.83 ± 0.40 |
| Kidneys | 1.77 ± 0.31 |
| Muscle | 0.49 ± 0.06 |
| Bone | 0.71 ± 0.20 |
| Tumor | 3.71 ± 0.97 |
| Tumor size (g) | 0.86 ± 0.34 |

Example 3. Biodistribution and Absorbed Dose Calculation

HuA33-C825 described in the prior Examples was tested for its in vivo efficacy. Biodistribution of radiolabeled DOTA-Bn and estimates of absorbed doses in mice implanted with SW1222 tumor cells were determined.

In this Example, PRIT was carried out in groups of A33-positive SW1222 tumor-bearing mice with the optimum doses of huA33-C825 and CA, followed with 2.0 MBq (~10 pmol) of $^{177}$Lu-DOTA-Bn and biodistribution studies were carried out from 2-120 h p.i. of $^{177}$Lu-DOTA-Bn to determine the $^{177}$Lu-activity residence time in tumor and various normal tissues.

Briefly, $^{177}$Lu-activity in tumor and various normal tissues determined using a biodistribution assay following PRIT with optimum A33-C825 (0.25 mg/mouse) and dextran-clearing agent doses (25% (w/w), 62.5 µg) and 2.0 MBq (~10 pmol) of $^{177}$Lu-DOTA-Bn. Groups of SW1222 tumor-bearing mice (n=4 to 5) were given 250 µg of huA33-C825, followed 24 h later with 25% (w/w) (62.5 µg) dextran-clearing agent, and after an additional 4 h, 2.0 MBq (~10 pmol) of 177Lu-DOTA-Bn. A single group of animals was sacrificed at 2, 24, and 120 h p.i. of $^{177}$Lu-DOTA-Bn for biodistribution analysis. These data were used as described in the Materials and Methods to estimate absorbed doses for radioimmunotherapy with $^{177}$Lu-DOTA-Bn (Table 5).

For tumor, $^{177}$Lu-uptake occurred very rapidly following administration, with an average of 7.0% ID/g at 2 h p.i. Maximum tumor uptake was 8.5% ID/g at 24 h p.i. and decreased by approximately half to 4.0% ID/g over the next 96 h at 120 h p.i. Peak kidney, liver, spleen and blood uptake was observed at 2 h p.i. (0.87, 0.70, 0.92, and 0.75% ID/g, respectively; average values), and decreased (also average values) to 0.27 (3.2-fold reduction compared to peak uptake), 0.30 (2.3-fold reduction), 0.32 (2.9-fold reduction), and 0.02 (37.5-fold reduction) % ID/g (also average values), respectively.

Exemplary estimates of absorbed doses for tumor and select normal tissue in female athymic mice carrying s.c. A33 positive-colorectal cancer tumors for PRIT including the optimum huA33-C825 and dextran-clearing agent doses are set forth in Table 6. For each target region, the absorbed dose was calculated as the product of the $^{177}$Lu equilibrium dose constant for non-penetrating radiations (i.e. beta rays) and the target regions $^{177}$Lu cumulated activity, assuming complete local absorption of the $^{177}$Lu beta rays and ignoring the gamma ray and non-self dose contributions.

TABLE 5

| Tissue | 2 hr (n = 5) | 24 hr (n = 4) | 120 hr (n = 5) |
|---|---|---|---|
| Blood | 0.75 ± 0.16 | 0.08 ± 0.02 | 0.02 ± 0.01 |
| Heart | 0.30 ± 0.05 | 0.11 ± 0.03 | 0.05 ± 0.01 |
| Lungs | 0.59 ± 0.10 | 0.21 ± 0.07 | 0.06 ± 0.02 |
| Liver | 0.70 ± 0.14 | 0.43 ± 0.09 | 0.30 ± 0.03 |
| Spleen | 0.92 ± 0.15 | 0.47 ± 0.14 | 0.32 ± 0.12 |
| Stomach | 0.15 ± 0.03 | 0.04 ± 0.01 | 0.02 ± 0.01 |
| Small Intestine | 0.14 ± 0.02 | 0.05 ± 0.01 | 0.02 ± 0.00 |
| Large Intestine | 0.17 ± 0.03 | 0.05 ± 0.01 | 0.04 ± 0.02 |
| Kidneys | 0.87 ± 0.09 | 0.46 ± 0.27 | 0.27 ± 0.09 |
| Muscle | 0.12 ± 0.01 | 0.03 ± 0.02 | 0.02 ± 0.00 |
| Bone | 0.09 ± 0.02 | 0.03 ± 0.02 | 0.03 ± 0.00 |
| Tumor | 6.99 ± 1.24 | 8.46 ± 3.74 | 3.99 ± 0.44 |
| Tumor size (g) | 1.31 ± 0.50 | 1.08 ± 0.45 | 0.98 ± 0.32 |
| Tumor-to-tissue ratios | 2 hr (n = 5) | 24 hr (n = 4) | 120 hr (n = 5) |
| Blood | 9.3 ± 2.6 | 107.2 ± 54.0 | 181.0 ± 62.1 |
| Heart | 23.7 ± 6.1 | 78.1 ± 41.3 | 78.6 ± 22.3 |
| Lungs | 11.8 ± 3.0 | 40.2 ± 22.4 | 64.4 ± 25.0 |
| Liver | 10.0 ± 2.7 | 19.5 ± 9.5 | 13.5 ± 2.2 |
| Spleen | 7.6 ± 1.8 | 18.0 ± 9.7 | 12.5 ± 4.8 |
| Stomach | 46.6 ± 13.5 | 225.0 ± 113.5 | 166.2 ± 50.5 |
| Small Intestine | 49.7 ± 11.6 | 182.0 ± 91.8 | 210.5 ± 43.9 |
| Large Intestine | 41.5 ± 11.2 | 177.8 ± 89.8 | 104.3 ± 49.2 |
| Kidneys | 8.1 ± 1.7 | 18.3 ± 13.4 | 14.8 ± 4.9 |
| Muscle | 58.6 ± 12.4 | 285.3 ± 212.8 | 249.4 ± 58.6 |
| Bone | 78.0 ± 22.4 | 293.8 ± 211.5 | 149.5 ± 31.0 |

TABLE 6

| Tissues | cGy/MBq | Therapeutic Index |
|---|---|---|
| Blood | 0.9 | 73 |
| Tumor | 65.8 | |
| Heart | 1.4 | 47 |
| Lung | 1.8 | 37 |
| Liver | 6.3 | 10 |
| Spleen | 6.6 | 10 |
| Stomach | 0.6 | 110 |
| Small Intestine | 0.5 | 132 |
| Large Intestine | 0.8 | 82 |
| Kidneys | 5.3 | 12 |
| Muscle | 0.3 | 219 |
| Bone | 0.6 | 110 |

As shown in Table 6, the estimated absorbed doses of $^{177}$Lu-DOTA-Bn (as cGy/MBq) for blood, tumor, liver, spleen, and kidneys were 0.9, 65.8, 6.3, 6.6, and 5.3 respectively. Further, for a single-cycle treatment, a therapeutic index of 73 for tumor to blood, and 12 for kidney, indicates curative ranges for tumor targeting, with no major toxicity expected. Indeed, no toxicity was observed out to 140 days in the subjects with durable responses.

Tumor uptake after PRIT assessed by PET imaging demonstrated similar results as the biodistribution assay above with both the $^{86}$Y-DOTA-Bn and $^{177}$Lu-DOTA-Bn isotypes (data not shown).

Example 4. In Vivo Therapy Study

This Example illustrates the in vivo efficacy of a huA33-C825 bispecific antibody in pretargeted radioimmunotherapy to mediate a reduction in tumor burden in mice bearing A33-positive cancer cells. In particular, this Example describes effect of single- and dual-cycle therapy on tumor burden in SW1222-tumor bearing mice.

During the first therapy study, 5 groups of tumor-bearing mice (n=6 to 8 per group) were treated with either: vehicle (i.e., untreated, n=8, TV$_7$: 76±15 mm$^3$), 33.3 MBq $^{177}$Lu-DOTA-Bn alone (vehicle given during bispecific antibody and CA injections, n=6, TV$_7$: 116±23 mm$^3$), single-cycle IgG-C825 PRIT+33.3 MBq $^{177}$Lu-DOTA-Bn (n.s. IgG-C825 given in place of huA33-C825, n=8 TV$_7$: 100±10 mm$^3$), or single-cycle huA33-C825 PRIT+either 11.1 MBq or 33.3 MBq $^{177}$Lu-DOTA-Bn (both n=8, TV$_7$: 103±17 mm$^3$ and TV$_7$: 93±15 mm$^3$, respectively). The estimated absorbed doses to tumor for single-cycle huA33-C825 PRIT+either 11.1 MBq or 33.3 MBq $^{177}$Lu-DOTA-Bn were 730 and 2190 cGy, respectively (based on absorbed dose estimates from Table 6). The inventors observed that the relative tumor uptake decreased as the $^{177}$Lu-DOTA-Bn dose was increased during treatment, which may indicate approaching possible saturation at the tumor. This may impact estimated absorbed tumor dose. If an estimated 7% ID/g is used for peak tumor uptake (i.e., to account for reduced relative tumor uptake with the higher $^{177}$Lu-DOTA-Bn dose) following PRIT+33.3 MBq $^{177}$Lu-DOTA-Bn dose, then an estimated tumor absorbed dose of ~1800 cGy may be more accurate, overall suggesting an effective dose range of 1800-2200 cGy. Exemplary tumor response (represented as tumor volume [mm$^3$]) among mice from each $^{177}$Lu-DOTA-Bn treatment group is set forth in FIG. 5. The groups of tumor-bearing mice receiving either no treatment, treatment consisting of either 33.3 MBq $^{177}$Lu-DOTA-Bn alone, or single-cycle IgG-C825 PRIT+33.3 MBq $^{177}$Lu-DOTA-Bn showed no tumor responses. Scintigraphy of the two latter groups given $^{177}$Lu-DOTA-Bn showed minimal activity in the tumor region. In contrast, groups treated with single-cycle huA33-C825 PRIT+either 11.1 MBq or 33.3 MBq $^{177}$Lu-DOTA-Bn showed a slight growth delay of the tumors up to ~15 days following treatment, but produced no CR. For comparison, on day 23 post tumor-inoculation (16 days following $^{177}$Lu-DOTA-Bn injection), the tumor volumes (as average±SEM) were 1398±206 (n=8), 1051±167 (n=5), 877±109 (n=7), 694±138 (n=8), and 495±76 (n=8) for no treatment, 33.3 MBq $^{177}$Lu-DOTA-Bn alone, single-cycle IgG-C825 PRIT+33.3 MBq $^{177}$Lu-DOTA-Bn, or single-cycle huA33-C825 PRIT+either 11.1 MBq or 33.3 MBq $^{177}$Lu-DOTA-Bn, respectively. Within 30 days post tumor-inoculation, the average tumor size of all groups was >1250 mm$^3$, and the study was terminated. Similar results were observed with a higher dose single cycle huA33-C825 PRIT+$^{177}$Lu-DOTA-Bn treatment with 111.1 MBq $^{177}$Lu-DOTA-Bn (data not shown).

In a second therapy study, dual-cycle huA33-C825 PRIT treatment was investigated. Exemplary tumor response (represented as tumor volume [mm$^3$]) among mice receiving dual-cycle treatment is set forth in FIGS. 6A-6D.

Figure 6A:
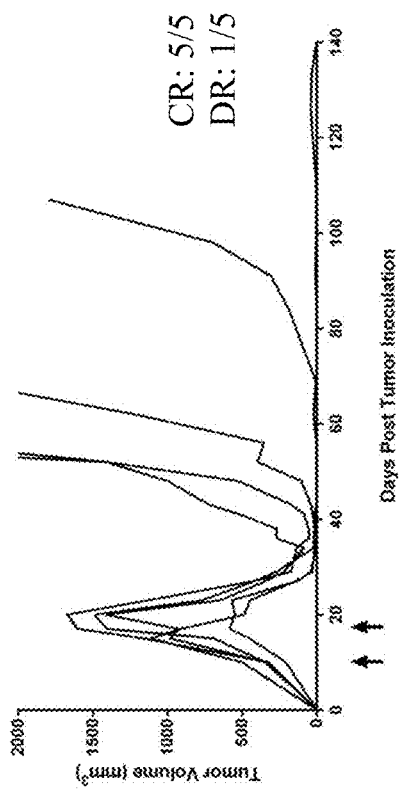
FIGS. 6A-6D show exemplary tumor growth measurements (mm$^3$) in mice receiving dual-cycle PRIT.
Figure 6B:
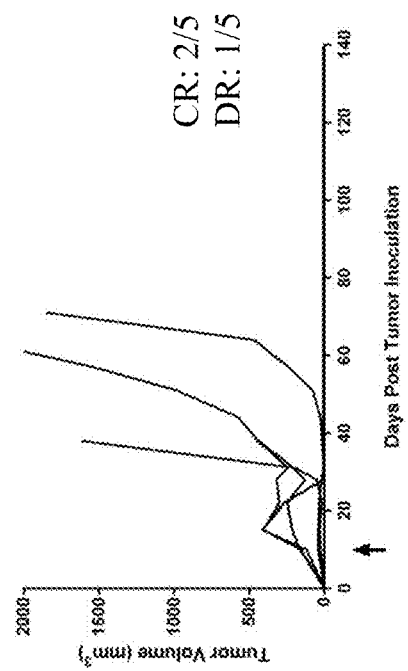
Figure 6C:
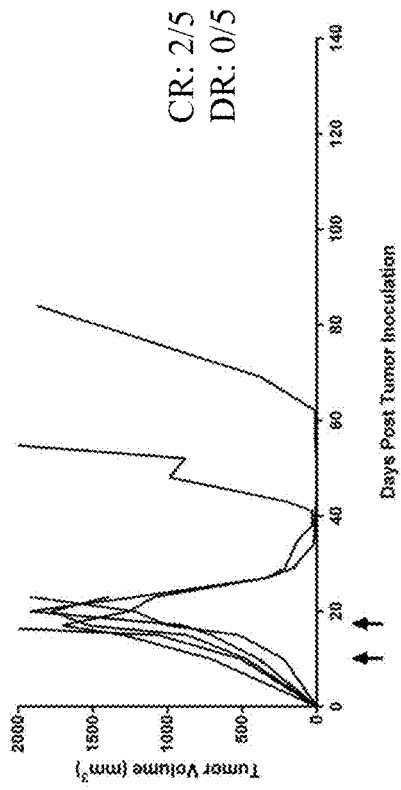
Figure 6D:
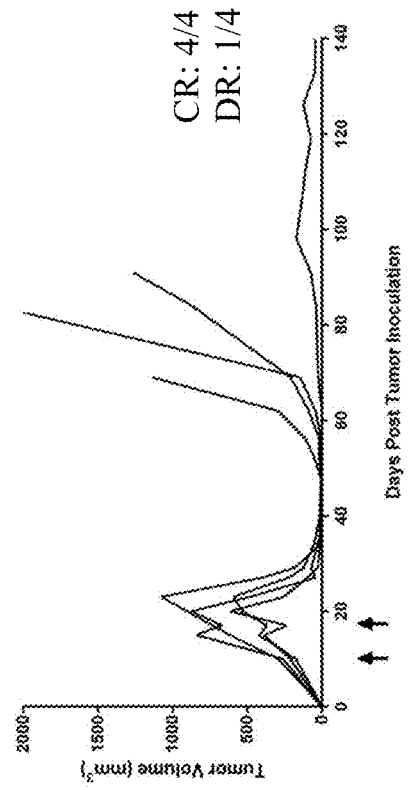
Figure 7:
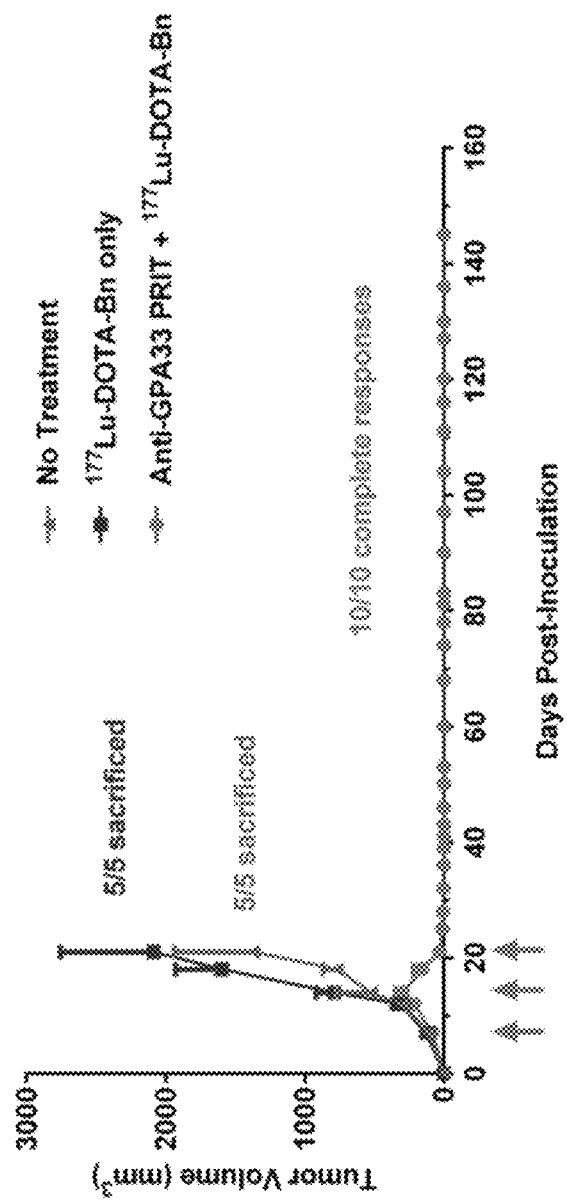
FIG. 7 shows an exemplary tumor response curve summarizing results of a DOTA-PRIT multi-cycle therapy study with nude mice bearing SW1222-colon cancer tumors. Three treatment arms are depicted: no treatment (triangles), $^{177}$Lu-DOTA-Bn only (squares), and a DOTA-PRIT treatment of 3 cycles of with 55 MBq of $^{177}$Lu-DOTA-Bn/cycle (165 MBq total administered activity; circles and each treatment indicated by arrows below the x-axis).

When mice were given either no treatment (n=5/TV$_{10}$: 314±77 mm$^3$), all mice required sacrifice within 30 days due to excessive tumor burden, and the time to reach 500 mm$^3$ was 13±2 d. Treatment with two cycles of PRIT+11.1 MBq $^{177}$Lu-DOTA-Bn (total $^{177}$Lu-DOTA-Bn dose 22.2 MBq; estimated tumor dose 1460 cGy) (n=5/TV$_{10}$: 462±179 mm$^3$), 2/5 animals showed CR (FIG. 6A). In the recurrent tumors, the time to reach 500 mm³ was 9 d (TV$_{10}$: 391 mm³) or 36 d (TV$_{10}$: 712 mm³). Treatment with 2 cycles of PRIT+33.3 MBq $^{177}$Lu-DOTA-Bn (total $^{177}$Lu-DOTA-Bn dose 66.6 MBq; estimated tumor dose 3600-4400 cGy) (n=5/344±105 mm³) produced CR (FIG. 6B) in 5/5 animals. In these recurrent tumors, the time to reach 500 mm³ was 12 d (TV$_{10}$: 325 mm³), 65 d (TV$_{10}$: 502 mm³), 7 d (TV$_{10}$: 341 mm³), and 23 d (TV$_{10}$: 345 mm³), and a single mouse had a tumor size of <10 mm³ at time of sacrifice. Treatment with two cycles of PRIT+55.5 mCi $^{177}$Lu-DOTA-Bn (total $^{177}$Lu-DOTA-Bn dose 111.0 MBq; estimated tumor dose: 2580 cGy, based on peak tumor uptake of 3% ID/g) (n=4/236±54 mm³) produced CR in 4/4 animals (FIG. 6C). In these recurrent tumors, the time to reach 500 mm³ was 34 d (TV$_{10}$: 295 mm³), 45 d (TV$_{10}$: 263 mm³), and 42 d (TV$_{10}$: 175 mm³), and a single mouse had a tumor size of 44 mm³ at time of sacrifice. Following treatment with two cycles of PRIT+33.3 mCi $^{177}$Lu-DOTA-Bn (total $^{177}$Lu-DOTA-Bn dose: 66.6 MBq), the average recurrence time to 500 mm³ was 27±26 d. For treatment with two cycles of PRIT+55.5 MBq $^{177}$Lu-DOTA-Bn (total $^{177}$Lu-DOTA-Bn dose: 111 MBq), the average recurrence time to 500 mm³ was 40±6 d. Exemplary estimates of absorbed radiation doses (represented in Gy units) for each treatment regimen is set forth in Table 7.

no radiation-induced toxicity. For 1/3 mice, the liver showed extramedullary hematopoiesis, and the liver was normal for the other two within the group. For 1/3 mice, the spleen (white pulp) showed follicular lymphoid hyperplasia, and the spleen was normal for the other two within the group. For the mice treated with two cycles of PRIT+55.5 MBq, a single mouse was submitted seven weeks following treatment, while the other two were submitted nine weeks following treatment. All three of these mice showed a CR, followed by reoccurrence of tumor, and required sacrifice due to excessive tumor burden. For 3/3 mice, the kidney, bone marrow, and liver were normal. For 1/3 mice, the spleen (white pulp) showed follicular lymphoid hyperplasia, and the spleen was normal for the other two within the group.

This Example just confirms, among other things, that huA33-C825 effectively reduce tumor burden (i.e., reduce tumor growth) in vivo and provide for effective PRIT.

Example 6. Curative Theranostic Prit

This Example documents use of humanized A33 bispecific antibodies described in prior Examples, and, among other things, demonstrates treatments using these antibodies can be curative. Specifically, it demonstrates theranostic

TABLE 7

| Treatment Group | Tumor | Blood | Kidney | Complete Response | Cures at 40 d post-treatment |
|---|---|---|---|---|---|
| Controls | | | | | |
| non-pretargeted 11.1 MBq | | | | 0/5 | 0/5 |
| non-pretargeted 33.3 MBq | | | | 0/6 | 0/6 |
| IgG-C825 + 11.1 MBq | | | | 0/5 | 0/5 |
| IgG-C825 + 33.3 MBq | | | | 0/7 | 0/7 |
| Single-cycle | | | | | |
| huA33-C825 + 11.1 MBq | 7.3 | 0.1 | 0.6 | 0/8 | 0/8 |
| huA33-C825 + 33.3 MBq | 21.9 | 0.3 | 1.8 | 0/8 | 0/8 |
| Dual-cycle | | | | | |
| huA33-C825 + 11.1 MBq (×2); 22.2 MBq | 14.6 | 0.2 | 1.2 | 2/5 | 1/5 |
| huA33-C825 + 33.3 MBq (×2); 66.6 MBq | 43.8 | 0.6 | 3.5 | 5/5 | 2/5 |
| huA33-C825 + 55.5 MBq (×2); 111.0 MBq | 73.0 | 1.0 | 5.9 | 4/4 | 2/4 |
| Triple-cycle | | | | | |
| huA33-C825 + 55.5 MBq (×3); 165.0 MBq | 140 | 1.5 | 8.8 | 10/10 | 10/10 |

Similar trends for survival were observed in animals at 140 days post-treatment (data not shown).

Example 5. Toxicity

This Example illustrates the in vivo toxicity of humanized A33 bispecific antibodies described in the prior Examples.

Briefly, a total of six mice treated with either two cycles of PRIT+11.1 MBq of $^{177}$Lu-DOTA-Bn (n=3) or two cycles of PRIT+1.5 mCi of $^{177}$Lu-DOTA-Bn (n=3) were submitted for anatomic pathology assessment of kidney, bone marrow, liver, and spleen up to 9 weeks following treatment. The 3/5 mice that showed no CR during after treatment with two cycles of PRIT+0.3 mCi of $^{177}$Lu-DOTA-Bn were submitted five days following injection of the second $^{177}$Lu-DOTA-Bn dose (i.e., following treatment). These mice did not show any reduction in tumor size following treatment, and required sacrifice due to excessive tumor burden. In 3/3 mice, the kidney and bone marrow were normal, suggesting curative treatment regimens that included additional treatment cycles with increased total amounts of administered activity.

Nude mice bearing established SW1222 s.c. xenografts (n=20; tumor volume=102±40 mm³; average±standard deviation (SD)) underwent treatment (n=5-10/group) with either: no treatment (n=5), $^{177}$Lu-DOTA-Bn only (n=5), or a three-cycle PRIT regimen consisting of anti-GPA33 PRIT+55 MBq of $^{177}$Lu-DOTA-Bn (n=10; total: 165 MBq). Serial nanoSPECT/CT imaging was conducted on five randomly selected mice undergoing DPRIT up to 160 hours post-injection of the first cycle of $^{177}$Lu-DOTA-Bn for dosimetry calculations.

DPRIT induced complete tumor response in 10/10 mice (controls: 10/10 dead at 21 days post-tumor inoculation), with tumor-free survival of all treated animals at 100 days and no obvious toxicities. Necropsy of 5/10 mice at 100 days verified cures, as well as showed no remarkable histopathologic findings of evaluation of kidney, liver, spleen, and bone/marrow (data not shown). Dosimetry estimates of $^{177}$Lu-radiation exposure to tumor following cycle 1 was 4556±637 rads (n=5, average±SD). Based on these data, a first-order approximation of the total $^{177}$Lu-radiation exposure to tumor following curative DPRIT (i.e., 3 cycles) was 14000 rads (with radiation doses to blood and kidney of 150 rads (therapeutic index (TI): 93) and 875 rads (TI: 16), respectively).

Lutetium-177 nanoSPECT/CT imaging of three-cycle PRIT regimen treated animals showed high contrast with visible uptake in tumors and minimal tissue background (data not shown). TI~70:1. Detection of tumors of 10 mg or less, based on non-invasive in vivo cross-sectional imaging in living mice was observed. This Example just confirms, among other things, that huA33-C825 effectively reduce tumor burden in vivo and that a PRIT-based theranostic may have curative effects and/or be used to detect small tumors.

Example 7. Theranostic "Real-Time" Simultaneous Treatment and Image-Guided Dosimetry This Example documents in vivo response to a theranostic DOTA-PRIT regimen using humanized A33 bispecific antibodies described in the prior Examples and demonstrates treatment efficacy via simultaneous treatment and image-guided dosimetry. Specifically, nanoSPECT/CT was utilized for high-resolution quantitative imaging of mice undergoing $^{177}$Lu-DPRIT treatment for "real-time" dosimetry.

Figure 8:
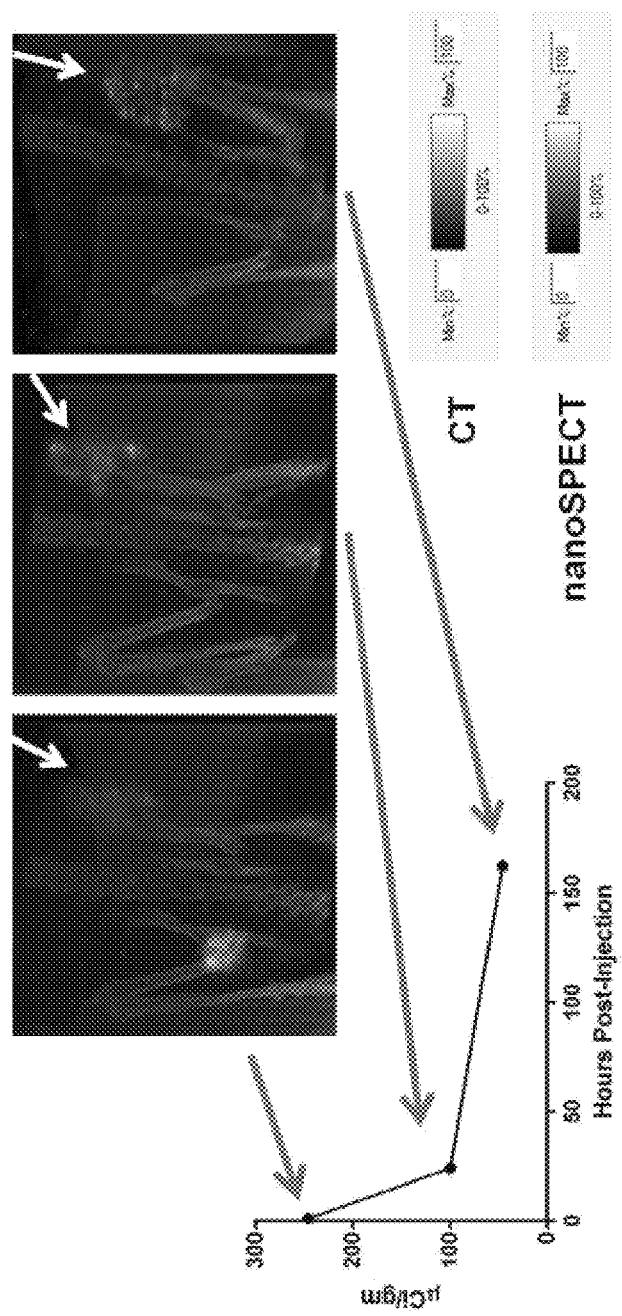
FIG. 8 shows exemplary maximum intensity nanoSPECT/CT images and activity concentration in tumor over time. Images were collected from a SW1222-tumor bearing nude mouse treated with a single cycle of anti-GPA33 PRIT+55 MBq of $^{177}$Lu-DOTA-Bn and imaged by nanoSPECT/CT at 1, 24, and 160 hours post-injection of $^{177}$Lu-DOTA-Bn. Shown is the maximum intensity nanoSPECT/CT images of the lower flank region where the tumor is located. Activity concentration in tumor was determined by region-of-interest analysis of the calibrated images.

A SW1222-tumor bearing nude mouse (volume: 100 mm$^3$ according to Vernier caliper measurement) treated with a single cycle of anti-GPA33 PRIT+55 MBq of $^{177}$Lu-DOTA-Bn and imaged by nanoSPECT/CT at three times following injection of $^{177}$Lu-DOTA-Bn: at 1, 24, and 160 hours post-injection. Shown in FIG. 8 is the maximum intensity nanoSPECT/CT images of the lower flank region where the tumor is located. The images were decay corrected to the time of injection and calibrated using known activity standards. The activity concentration in tumor was determined using region-of-interest analysis of the calibrated images. This Example just confirms, among other things, that huA33-C825 effectively reduce tumor burden in vivo and that high-resolution quantitative imaging is one method that can be used to measure efficacy.

Materials and Methods for Examples

Tumor Cell Lines and Cell Culture Reagents

The human colorectal cancer cell line SW1222 was obtained by the Ludwig Institute for Cancer Immunotherapy (New York, N.Y.) and maintained by serial passage. The cells were cultured in Minimal Essential Medium supplemented with 10% heat inactivated fetal calf serum, 2.0 mM glutamine, 100 units/mL penicillin, and 100 units/mL streptomycin in a 37° C. environment containing 5% $CO_2$. Upon receipt of the cell line, cultures were established and cryopreserved in small aliquots to limit passages to less than three months, and periodically tested for *mycoplasma* according to manufacturer's specifications using a commercial kit (Lonza). For trypsinization during passage and harvesting of cells, a solution of 0.25% trypsin/0.53 mM EDTA in Hanks Buffered Salt Solution without calcium and magnesium was used.

Cloning and Expression of huA33-C825

HuA33-C825 was made using the platform previously described in Cheal, S. M. et al. (2014, Mol. Cancer Ther. 13(7), 10 pages) using the variable regions ($V_H$ and $V_L$) of humanized antibody A33 (huA33; King, D. J. et al., 1995, British J. Cancer 72:1364-1372). HuA33-C825 was produced in CHO cells in a mammalian expression vector and purified by protein A affinity chromatography as described (Cheal et al., supra).

Exemplary bispecific antibodies of the present invention are presented in Table 8 (huA33-C825: humanized A33 IgG1-murine C825 scFv; huA33-huC825: humanized A33 IgG1-humanized C825 scFv). For DNA sequences, leader sequences are presented as underlined text. For amino acid sequences, leader sequences are presented as underlined text, linker sequences are presented as bold text and variable region sequences are presented as italicized text.

TABLE 8

```
huA33-C825 light chain DNA
ATGGGCTGGTCCTGCATCATCCTGTTTCTGGTGGCTACCGCCACCGGCGACATCCAG
ATGACCCAGTCCCCCTCCTCCCTGTCCGTGTCTGTGGGCGACAGAGTGACCATCACA
TGCAAGGCCTCCCAGAACGTGCGGACCGTGGTGGCCTGGTATCAGCAGAAGCCTGG
CCTGGCCCCCAAGACCCTGATCTACCTGGCCTCTAACCGGCACACCGGCGTGCCCTC
CAGATTCTCCGGATCTGGCTCTGGCACCGACTTTACCTTCACCATCTCCAGCCTGCA
GCCCGAGGATATCGCCACCTACTTTTGCCAGCAGCACTGGTCCTACCCCTGACCTT
TGGCCAGGGCACCAAGGTGGAAGTGAAGAGAACCGTGGCCGCTCCCTCCGTGTTCA
TCTTCCCACCTTCCGACGAGCAGCTGAAGTCCGGCACCGCTTCTGTCGTGTGCCTGC
TGAACAACTTCTACCCCCGCGAGGCCAAGGTGCAGTGGAAGGTGGACAACGCCCTG
CAGTCCGGCAACTCCCAGGAATCCGTGACCGAGCAGGACTCCAAGGACAGCACCTA
CAGCCTGTCCTCCACCCTGACCCTGTCCAAGGCCGACTACGAGAAGCACAAGGTGT
ACGCCTGCGAAGTGACCCACCAGGGCCTGTCTAGCCCCGTGACCAAGTCTTTCAACC
GGGGCGAATGTGGCGGCGGAGGATCTGGCGGAGGCGGCTCTGCTTCTCACGTGAAG
CTGCAGGAAAGCGGCCCTGGACTGGTGCAGCCTTCCCAGTCTCTGTCCCTGACCTGC
ACCGTGTCCGGCTTCTCCCTGACCGATTACGGCGTGCACTGGGTGCGACAGTCTCCA
GGCAAGGGCCTGGAATGGCTGGGAGTGATTTGGAGCGGTGGCGGAACCGCCTACAA
CACCGCCCTGATCTCCCGCTGAACATCTACCGGGACAACTCCAAGAACCAGGTGTT
CCTGGAAATGAACTCCCTGCAGGCAGAGGACACCGCCATGTACTACTGCGCCAGAC
GGGGCTCCTACCCCTACAACTACTTCGACGCTTGGGGCTGCGGCACCACCGTGACAG
TGTCTAGCGGAGGTGGTGGATCTGGGGGCGGAGGTAGCGGAGGGGGAGGTTCTCAG
GCTGTCGTGATCCAGGAATCTGCCCTGACCACCCCCCCTGGCGAGACAGTGACACTG
ACCTGCGGATCTTCCACCGGCGCTGTGACCGCCTCCAACTACGCCAACTGGGTGCAG
GAAAAGCCCGACCACTGCTTCACCGGCCTGATCGGCGGCCACAACAACAGACCTCC
AGGCGTGCCAGCCCGGTTCTCCGGCTCTCTGATCGGAGATAAGGCCGCCCTGACAAT
CGCCGGCACCCAGACAGAGGACGAGGCTATCTACTTCTGCGCCCTGTGGTACAGCG
ACCACTGGGTCATCGGCGGAGGCACCAGACTGACCGTGCTGGGATAG (SEQ ID
NO: 1)
```

TABLE 8-continued huA33-C825 light chain amino acid
MGWSCIILFLVATATGDIQMTQSPSSLSVSVGDRVTITCKASQNVRTVVAWYQQKPGLAPKT
LIYLASNRHTGVPSRFSGSGSGTDFTFTISSLQPEDIATYFCQQHWSYPLTFGQGTKVEVKRTV
AAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGECGGGGSGGGGSASH
VKLQESGPGLVQPSQSLSLTCTVSGFSLTDYGVHWVRQSPGKGLEWLGVIWSGGGTAYNTALI
SRLNIYRDNSKNQVFLEMNSLQAEDTAMYYCARRGSYPYNYFDAWGCGTTVTVSSGGGGSG
GGGSGGGGSQAVVIQESALTTPPGETVTLTCGSSTGAVTASNYANWVQEKPDHCFTGLIGG
HNNRPPGVPARFSGSLIGDKAALTIAGTQTEDEAIYFCALWYSDHWVIGGGTRLTVLG (SEQ
ID NO: 2)

huA33-huC825 light chain amino acid (15 aa linker)
MGWSCIILFLVATATGDIQMTQSPSSLSVSVGDRVTITCKASQNVRTVVAWYQQKPGLAPKT
LIYLASNRHTGVPSRFSGSGSGTDFTFTISSLQPEDIATYFCQQHWSYPLTFGQGTKVEVKRTV
AAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGECTSGGGGSGGGGSG
GGGSHVQLVESGGGLVQPGGSLRLSCAASGFSLTDYGVHWVRQAPGKGLEWLGVIWSGGG
TAYNTALISRFTISRDNSKNTLYLQMNSLRAEDTAVYYCARRGSYPYNYFDAWGCGTLVTVSSG
GGGSGGGGSGGGGSQAVVTQEPSLTVSPGGTVTLTCGSSTGAVTASNYANWVQQKPGQCP
RGLIGGHNNRPPGVPARFSGSLLGGKAALTLLGAQPEDEAEYYCALWYSDHWVIGGGTKLTV
LG (SEQ ID NO: 3)

huA33-huC825 light chain amino acid (30 aa linker)
MGWSCIILFLVATATGDIQMTQSPSSLSVSVGDRVTITCKASQNVRTVVAWYQQKPGLAPKT
LIYLASNRHTGVPSRFSGSGSGTDFTFTISSLQPEDIATYFCQQHWSYPLTFGQGTKVEVKRTV
AAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGECTSGGGGSGGGGSG
GGGSHVQLVESGGGLVQPGGSLRLSCAASGFSLTDYGVHWVRQAPGKGLEWLGVIWSGGG
TAYNTALISRFTISRDNSKNTLYLQMNSLRAEDTAVYYCARRGSYPYNRFDAWGCGTLVTVSSG
GGGSGGGGSGGGGSGGGGSGGGGSGGGGSQAVVTQEPSLIVSPGGTVTLTCGSSTGAV
TASNYANWVQQKPGQCPRGLIGGHNNRPPGVPARFSGSLLGGKAALTLLGAQPEDEAEYYC
ALWYSDHWVIGGGTKLTVLG (SEQ ID NO: 4)

huA33-C825 heavy chain IgG1 DNA (aglycosylated)
ATGGGCTGGTCCTGCATCATCCTGTTTCTGGTGGCTACCGCCACCGGCGAGGTGCAG
CTGCTGGAATCTGGCGGAGGACTGGTGCAGCCTGGCGGCTCTCTGAGACTGTCTTGT
GCCGCCTCTGGCTTCGCCTTCTCCACCTACGACATGTCCTGGGTGCGACAGGCTCCT
GGCAAGGGCCTGGAATGGGTGGCCACAATCTCTTCCGGCGGCTCCTACACCTACTAC
CTGGACTCTGTGAAGGGCCGGTTCACCATCTCCCGGGACTCCTCCAAGAACACCCTG
TACCTGCAGATGAACTCCCTGCAGGCCGAGGACTCCGCCATCTACTACTGTGCCCCT
ACCACCGTGGTGCCCTTCGCTTATTGGGGCCAGGGCACCCTCGTGACCGTGTCCTCT
GCTTCTACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGAC
GGTGTCGTGGAACTCAGGCGCCCTGACCAGCGGCGTGCACACCTTCCCGGCCGTCCT
ACAGTCCTCAGGACTCTACTCCCTCAGCAGCGTGGTGACCGTGCCCTCCAGCAGCTT
GGGCACCCAGACCTACATCTGCAACGTGAATCACAAGCCCAGCAACACCAAGGTGG
ACAAGAGAGTTGAGCCCAAATCTTGTGACAAAACTCACACATGCCCACCGTGCCCA
GCACCTGAACTCCTGGGGGGACCGTCAGTCTTCCTCTTCCCCCCAAAACCCAAGGAC
ACCCTCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAATGC
CAAGACAAAGCCGCGGGAGGAGCAGTACGCCAGCACGTACCGTGTGGTCAGCGTCC
TCACCGTCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGGGCAGCC
CCGAGAACCACAGGTGTACACCCTGCCCCCATCCCGGGATGAGCTGACCAAGAACC
AGGTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCACTACACG
CAGAAGAGCCTCTCCCTGTCTCCGGGTAAATGA (SEQ ID NO: 5)

huA33-C825 heavy chain IgG1 amino acid (aglycosylated)
MGWSCHILFLVATATGEVQLLESGGGLVQPGGSLRLSCAASGFAFSTYDMSWVRQAPGKGL
EWVATISSGGSYTYYLDSVKGRFTISRDSSKNTLYLQMNSLQAEDSAIYYCAPTTVVPFAYWGQ
GTLVIVSSASTKGPSVFPLAPSSKSTSGGTAALGCLVKDYFPEPVTVSWNSGALTSGVHT
FPPAVLQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVHNAK
TKPREEQYASTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK (SEQ ID NO: 6)

huA33-C825 heavy chain IgG1 amino acid (aglycosylated, K322A)
MGWSCIILFLVATATGEVQLLESGGGLVQPGGSLRLSCAASGFAFSTYDMSWVRQAPGKGL
EWVATISSGGSYTYYLDSVKGRFTISRDSSKNTLYLQMNSLQAEDSAIYYCAPTIVVPFAYWGQ
GTLVTVSSASTKGPSVFPLAPSSKSTSGGTAALGCLVKDYFPEPVTVSWNSGALTSGVHT
FPPAVLQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVHNAK
TKPREEQYASTYRVVSVLTVLHQDWLNGKEYKCAVSNKALPAPIEKTISKAKGQPREPQ
VYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK (SEQ ID NO: 7)

Surface Plasmon Resonance Studies

Biacore T100 Biosensor, CM5 sensor chip, and related reagents were purchased from GE Healthcare. Recombinant human A33 protein was purchased from Novoprotein. A BSA-(Y)-DOTA-Bn conjugate was prepared as described (Cheal et al., supra). A33 and DOTA antigens were immobilized using the Amino Coupling kit (GE Healthcare). Purified bispecific antibodies and control antibodies were analyzed, and data were fit to a bivalent analyte model using the Biacore T100 evaluation software as described (Cheal et al., supra).

PRIT Reagents, Protocol and Xenograft Studies

All animal experiments were approved by the Institutional Animal Care and Use Committee of Memorial Sloan Kettering Cancer Center and institutional guidelines for the proper and humane use of animals in research were followed. Athymic nu/nu female mice (6-8 weeks old; Harlan Sprague Dawley) were allowed to acclimate in the vivarium for at least one week. Groups of animals were injected s.c. with A33-positive SW1222 in the left flank with $5 \times 10^6$ cells formulated 1:1 with Matrigel (BD Biosciences), and established tumors (100-900 mm$^2$) were observed in 7-10 days using the formula for the volume of an ellipsoid $V=4/3\pi$ (length/2×width/2×height/2). All reagents were given intravenously (i.v.) via the lateral tail vein. PRIT protocol included injections of: huA33-C825 [t=−28 h], followed 24 h later by CA (the CA is a 500 KDa dextran-(Y)-DOTA-Bn conjugate, prepared according to Orcutt et al. (2011, Nucl. Med. Biol. 38:223-233) and formulated in saline for injection; the substitution ratio of moles of (Y)-DOTA-Bn per moles of dextran was 61(Y)-DOTA-Bn/dextran) [t=−4 h], and $^{177}$Lu-DOTA-Bn (prepared as previously described by incubating aminobenzyl-DOTA(p-NH2-Bn-DOTA) from Macrocyclics and $^{177}$LuCl$_3$ (specific activity ~30 Ci/mg; Perkin Elmer) and formulating in saline for injection) after 4 h [t=0 h]. In addition, huA33-C825 was trace radiolabeled with I-131 to estimate tumor uptake during PRIT. The IODOGEN method (Cheal, S. et al., 2014, Mol. Cancer Ther. 13(7):1-10) was used to prepare $^{131}$I-huA33-C825 (final specific activity 95.5 MBq/mg, with cold huA33-C825 added to achieve desired mg dose, radiochemical purity >98% using size-exclusion high pressure liquid chromatography), and the in vitro cell binding immunoreactivity was evaluated using SW1222 cells essentially as described by Lindmo method (Lindmo, T. et al., 1990, J. Immunol. Meth. 126(2):183-189). For PRIT with non-specific IgG-C825, an equivalent mg dose of a GD2-targeted bispecific antibody (hu3F8-C825) was used in place of huA33-C825. For ex vivo biodistribution analysis, mice were euthanized by $CO_2$(g) asphyxiation, and tumor and selected organs were harvested, rinsed with water and allowed to air-dry, weighed and radioassayed by gamma scintillation counting (Perkin Elmer Wallac Wizard 3"). Count rates were background and decay corrected, converted to activities using a system calibration factor, normalized to the administered activity, and expressed as percent injected dose per gram (% ID/g). Differences in $^{177}$Lu-activity concentration in tumor and various tissues were analyzed by Student's unpaired t test when appropriate.

Estimation of Absorbed Doses

Groups of A33-positive SW1222 tumor-bearing mice (n=4-5) were given 0.25 mg of huA33-C825, CA (62.5 µg; 25% (w/w)), and 1.85-2.0 MBq (~10 pmol) of $^{177}$Lu-DOTA-Bn, and sacrificed at 2, 24, and 120 h p.i. For each tissue the non-decay-corrected time-activity concentration data were fit using Excel to a 1-component, a 2-component, or a more complex exponential function as appropriate, and analytically integrated to yield the cumulated activity concentration per unit administered activity (MBq-h/g per MBq). The $^{177}$Lu equilibrium dose constant for non-penetrating radiations (8.49 g-cGy/MBq-h) was used to estimate the tumor-to-tumor and select organ-to-organ self-absorbed doses, assuming complete local absorption of the $^{177}$Lu beta rays only and ignoring the gamma ray and non-self dose contributions. To determine the effect of the $^{177}$Lu-DOTA-Bn dose on the relative uptake of $^{177}$Lu-DOTA-Bn in tumor and select tissues with the highest absorbed doses (i.e., blood, liver, spleen, and kidneys), groups of SW1222 tumor-bearing female athymic nude mice (n=5/group) were given 0.25 mg (1.19 nmol) of huA33-C825 at t=−28 h and 62.5 µg of CA at t=−4 h, followed with either 11.1 MBq (11.14-11.40), 55.5 MBq (54.61-55.06 MBq), or 111 MBq (109.52-112.5 MBq). All groups were sacrificed at 24 h p.i. of $^{177}$Lu-DOTA-Bn (i.e., time of maximum tumor uptake) for biodistribution analysis of $^{177}$Lu-activity.

PET Imaging of PRIT+$^{86}$Y-DOTA-Bn

A single group of mice bearing A33-positive SW1222 tumors in the shoulder (n=5) were given 0.25 mg of huA33-C825, CA (62.5 µg; 25% (w/w)), and 8.6-8.8 MBq (~50 pmol) of $^{86}$Y-DOTA-Bn, and non-invasively imaged using a microPET Focus 120 (CTI Molecular Imaging, Inc. Knoxville, Tenn.) at approximately 2 and 20 h p.i. The following imaging acquisition parameters were used: energy window of 350-750 keV, coincidence timing window of 6 nsec, and an acquisition time of 20 min. The resulting list-mode data were sorted into 2D histograms by Fourier re-binning and transverse images reconstructed by filtered back-projection into a 128×128×95 matrix (reconstructed spatial resolution is 2.6 mm full-width half maximum (FWHM)). The image data were corrected for non-uniformity of response of the scanner, deadtime count losses, physical decay (to the time of injection), and the $^{86}$Y positron branching ratio. No attenuation, scatter, or partial-volume averaging correction was applied. An empirically determined system calibration factor (i.e. µCi/mL/cps/voxel) for mice was used to convert voxel count rates to activity concentrations. The resulting image data were then normalized to the administered activity to determine by region-of-interest analysis the percent of the injected dose per gram (% ID/g) of tissue corrected for radioactive decay to the time of injection. AsiPRO VM 5.0 software (Concorde Microsystems, Knoxville, Tenn.) was used to perform image and region of interest (ROI) analyses (as ROI maximum, % ID/g). The animals were sacrificed at 24 h p.i. for ex vivo biodistribution analysis.

Autoradiography and Immunohistochemistry

Frozen and OCT-embedded tumor and kidney from select mice administered huA33-C825 PRIT followed with either 11.1 (11.14-11.40), 55.5 (54.61-55.06), or 111 MBq (109.52-112.5 MBq) of $^{177}$Lu-DOTA-Bn (time of sacrifice: 24 hours p.i.) were cut into 10 µm sections using a cryostat (Avantik, Springfield, NJ), and immediately exposed to imaging plate (Fuji Photo Film, Kanagawa, Japan) for 72 h and subsequently scanned using Typhoon FLA 7000 scanner (GE, Pittsburgh, Pa.). The same sections underwent hematoxylin and eosin staining and were scanned under Olympus BX60 microscope equipped with controlled moving stage (Olympus, Central Valley, Pa.). Both autoradiogram and microscope images were processed and analyzed using ImageJ (NIH).

Therapy and Scintigraphy Studies

Groups of mice bearing established s.c. A33-positive SW1222 xenografts were injected with either huA33-C825 or non-specific (n.s.) IgG-C825 PRIT (i.e., single-cycle treatment, $^{177}$Lu-DOTA-Bn injection on day 7 post tumor-inoculation) or two cycles of PRIT (i.e., dual-cycle treatment study, $^{177}$Lu-DOTA-Bn injections given on day 10 and day 17 post tumor-inoculation). For the dual-cycle treatment study, the tumor volume on day 10-post tumor inoculation (TV10) is described (i.e., day of first $^{177}$Lu-DOTA-Bn injection) and expressed when appropriate as average±SD. The following definitions were used to describe treatment response: a complete response (CR) is defined as tumor shrinkage to <100 mm$^3$. A durable response (DR) was defined as survival at 140 days post treatment. Excessive tumor burden is defined as >2000 mm$^3$. For scintigraphy studies, select groups of A33-positive SW1222 tumor-bearing mice undergoing treatment were placed under anesthesia by gas inhalation before scanning in a nanoSPECT (Bioscan, Washington D.C.) at 20 hours p.i. for 30 minutes (~10$^5$ counts per image) using a low-energy high-resolution collimator and a window set at 208 keV. Images were reconstructed to a 256×256 matrix using Bioscan HiSPECT software and uploaded into ASIPro VM for analysis.

EQUIVALENTS

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

Having thus described several aspects of at least one embodiment of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

REFERENCES

Ackerman, M. E. et al., 2008, A33 antigen displays persistent surface expression, Cancer Immunol. Immunother. 57(7):1017-1027.

Ackerman, M. E. et al., 2008, Effect of antigen turnover rate and expression level on antibody penetration into tumor spheroids, Mol. Cancer Ther. 7(7):2233-2240.

Barendswaard, E. C. et al., 1998, Rapid and specific targeting of monoclonal antibody A33 to a colon cancer xenograft in nude mice, International J. Oncol. 12:45-53.

Carrasquillo, J. A. et al., 2011, $^{124}$I-huA33 Antibody PET of Colorectal Cancer, J. Nucl. Med. 52:1173-1180.

Cheal, S. M. et al., 2014, Preclinical Evaluation of Multistep Targeting of Diasialoganglioside GD2 Using an IgG-scFv Bispecific Antibody with High Affinity for GD2 and DOTA Metal Complex, Mol. Cancer Ther. 13(7):1-10.

Cheal, S. M. et al., 2014, Evaluation of glycodendron and synthetically-modified dextran clearing agents for multstep targeting of radioisotopes for molecular imaging and radioimmunotherapy, Mol. Pharm. 11(2):400-416.

El Emir, E. et al., 2007, Predicting Response to Radioimmunotherapy from the Tumor Microenvironment of Colorectal Carcinomas, Cancer Res. 67(24):11896-11905.

Goodwin, D. A. et al., 1994, Pharmacokinetics of pretargeted monoclonal antibody 2D12.5 and $^{88}$Y-Janus-2-(p-nitrobenzyl)-1,4,7,10-tetraazacyclododecanetetraacetic acid (DOTA) in BALB/c mice with KHJJ mouse adenocarcinoma: a model for $^{90}$Y radioimmunotherapy, Cancer Res. 54(22):5937-5946.

King, D. J. et al., 1995, Preparation and preclinical evaluation of humanised a33 immunoconjugates for radioimmunotherapy, British J. Cancer 72:1364-1372.

Lindmo, T. et al., 1990, Immunometric assay by flow cytometry using mixtures of two particle types of different affinity, J. Immunol. Meth. 126(2):183-189.

Orcutt, K. D. et al., 2010, A modular IgG-scFv bispecific antibody topology, Protein Engineering Design & Selection 23(4):221-228.

Orcutt, K. D. et al., 2011, Engineering an antibody with picomolar affinity to DOTA chelates of multiple radionuclides for pretargeted radioimmunotherapy and imaging, Nucl. Med. Biol. 38(2):223-233.

O'Donoghue, J. A. et al., 2011, $^{124}$I-huA33 antibody uptake is driven by a33 antigen concentration in tissues from colorectal cancer patients imaged by immuno-pet. J. Nucl. Med. 52:1878-1885.

Scott, A. M. et al., 2005, A phase I trial of humanized monoclonal antibody A33 in patients with colorectal carcinoma: biodistribution, pharmacokinetics, and quantitative tumor uptake, Clin. Cancer Res. 11(13):4810-4817.

Welt, S. et al., 1994, Phase I/II study of iodine 131-labeled monoclonal antibody A33 in patients with advanced colon cancer, J. Clin. Oncol. 12(8):1561-71.

Welt, S. et al., 2003, Phase I study of anticolon cancer humanized antibody A33, Clin. Cancer Res. 9:1338-1346.

We claim:

1. An isolated nucleic acid molecule comprising the nucleic acid sequence of SEQ ID NO: 1 or SEQ ID NO: 5.

2. An expression vector comprising the nucleic acid molecule of claim 1.

3. A host cell comprising the expression vector of claim 2.

* * * * *

SEQUENCE LISTING

<160> NUMBER OF SEQ ID NOS: 9

<210> SEQ ID NO 1
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgggctggt cctgcatcat cctgtttctg gtggctaccg ccaccggcga catccagatg    60
acccagtccc cctcctccct gtccgtgtct gtgggcgaca gagtgaccat cacatgcaag   120
gcctcccaga cgtgcggac cgtggtggcc tggtatcagc agaagcctgg cctggccccc   180
aagaccctga tctacctggc tctaaccgg cacaccggcg tgccctccag attctccgga   240
tctggctctg gcaccgactt taccttcacc atctccagcc tgcagcccga ggatatcgcc   300
acctacttt gccagcagca ctggtcctac cccctgacct ttggccaggg caccaaggtg   360
gaagtgaaga gaaccgtggc cgctcccctcc gtgttcatct cccaccttc cgacgagcag   420
ctgaagtccg gcaccgcttc tgtcgtgtgc ctgctgaaca acttctaccc ccgcgaggcc   480
aaggtgcagt ggaaggtgga caacgccctg cagtccggca actcccagga atccgtgacc   540
gagcaggact ccaaggacag cacctacagc ctgtcctcca ccctgaccct gtccaaggcc   600
gactacgaga gcacaaggt gtacgcctgc gaagtgaccc accagggcct gtctagcccc   660
gtgaccaagt ctttcaaccg gggcgaatgt ggcggcggag atctggcgg aggcggctct   720
gcttctcacg tgaagctgca ggaaagcggc cctggactgg tgcagccttc ccagtctctg   780
tccctgacct gcaccgtgtc cggcttctcc ctgaccgatt acggcgtgca ctgggtgcga   840
cagtctccag gcaagggcct ggaatggctg ggagtgattt ggagcggtgg cggaaccgcc   900
tacaacaccg ccctgatctc ccggctgaac atctaccggg acaactccaa gaaccaggtg   960
ttcctggaaa tgaactccct gcaggcagag gacaccgcca tgtactactg cgccagacgg  1020
ggctcctacc cctacaacta cttcgacgct tggggctgcg gcaccaccgt gacagtgtct  1080
agcggaggtg gtggatctgg gggcggaggt agcggagggg gaggttctca ggctgtcgtg  1140
atccaggaat ctgccctgac cacccccct ggcgagacag tgacactgac ctgcggatct  1200
tccaccggcg ctgtgaccgc ctccaactac gccaactggg tgcaggaaaa gcccgaccac  1260
tgcttcaccg gcctgatcgg cggccacaac aacagacctc aggcgtgcc agcccggttc  1320
tccggctctc tgatcggaga taaggccgcc ctgacaatcg ccggcaccca gacagaggac  1380
gaggctatct acttctgcgc cctgtggtac agcgaccact gggtcatcgg cggaggcacc  1440
agactgaccg tgctgggata g                                            1461
```

<210> SEQ ID NO 2
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Gly Trp Ser Cys Ile Ile Leu Phe Leu Val Ala Thr Ala Thr Gly
1               5                   10                  15

Asp Ile Gln Met Thr Gln Ser Pro Ser Ser Leu Ser Val Ser Val Gly
            20                  25                  30
```

```
Asp Arg Val Thr Ile Thr Cys Lys Ala Ser Gln Asn Val Arg Thr Val
             35                  40                  45

Val Ala Trp Tyr Gln Gln Lys Pro Gly Leu Ala Pro Lys Thr Leu Ile
 50                  55                  60

Tyr Leu Ala Ser Asn Arg His Thr Gly Val Pro Ser Arg Phe Ser Gly
 65                  70                  75                  80

Ser Gly Ser Gly Thr Asp Phe Thr Phe Thr Ile Ser Ser Leu Gln Pro
                 85                  90                  95

Glu Asp Ile Ala Thr Tyr Phe Cys Gln Gln His Trp Ser Tyr Pro Leu
                100                 105                 110

Thr Phe Gly Gln Gly Thr Lys Val Glu Val Lys Arg Thr Val Ala Ala
                115                 120                 125

Pro Ser Val Phe Ile Phe Pro Pro Ser Asp Glu Gln Leu Lys Ser Gly
            130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
210                 215                 220

Phe Asn Arg Gly Glu Cys Gly Gly Gly Ser Gly Gly Gly Gly Ser
225                 230                 235                 240

Ala Ser His Val Lys Leu Gln Glu Ser Gly Pro Gly Leu Val Gln Pro
                245                 250                 255

Ser Gln Ser Leu Ser Leu Thr Cys Thr Val Ser Gly Phe Ser Leu Thr
            260                 265                 270

Asp Tyr Gly Val His Trp Val Arg Gln Ser Pro Gly Lys Gly Leu Glu
        275                 280                 285

Trp Leu Gly Val Ile Trp Ser Gly Gly Thr Ala Tyr Asn Thr Ala
290                 295                 300

Leu Ile Ser Arg Leu Asn Ile Tyr Arg Asp Asn Ser Lys Asn Gln Val
305                 310                 315                 320

Phe Leu Glu Met Asn Ser Leu Gln Ala Glu Asp Thr Ala Met Tyr Tyr
                325                 330                 335

Cys Ala Arg Arg Gly Ser Tyr Pro Tyr Asn Tyr Phe Asp Ala Trp Gly
            340                 345                 350

Cys Gly Thr Thr Val Thr Val Ser Ser Gly Gly Gly Gly Ser Gly Gly
        355                 360                 365

Gly Gly Ser Gly Gly Gly Gly Ser Gln Ala Val Val Ile Gln Glu Ser
        370                 375                 380

Ala Leu Thr Thr Pro Pro Gly Glu Thr Val Thr Leu Thr Cys Gly Ser
385                 390                 395                 400

Ser Thr Gly Ala Val Thr Ala Ser Asn Tyr Ala Asn Trp Val Gln Glu
                405                 410                 415

Lys Pro Asp His Cys Phe Thr Gly Leu Ile Gly Gly His Asn Asn Arg
                420                 425                 430

Pro Pro Gly Val Pro Ala Arg Phe Ser Gly Ser Leu Ile Gly Asp Lys
            435                 440                 445
```

```
Ala Ala Leu Thr Ile Ala Gly Thr Gln Thr Glu Asp Glu Ala Ile Tyr
        450                 455                 460
Phe Cys Ala Leu Trp Tyr Ser Asp His Trp Val Ile Gly Gly Gly Thr
465                 470                 475                 480
Arg Leu Thr Val Leu Gly
                485

<210> SEQ ID NO 3
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Trp Ser Cys Ile Ile Leu Phe Leu Val Ala Thr Ala Thr Gly
1               5                   10                  15
Asp Ile Gln Met Thr Gln Ser Pro Ser Ser Leu Ser Val Ser Val Gly
                20                  25                  30
Asp Arg Val Thr Ile Thr Cys Lys Ala Ser Gln Asn Val Arg Thr Val
            35                  40                  45
Val Ala Trp Tyr Gln Gln Lys Pro Gly Leu Ala Pro Lys Thr Leu Ile
    50                  55                  60
Tyr Leu Ala Ser Asn Arg His Thr Gly Val Pro Ser Arg Phe Ser Gly
65                  70                  75                  80
Ser Gly Ser Gly Thr Asp Phe Thr Phe Thr Ile Ser Ser Leu Gln Pro
                85                  90                  95
Glu Asp Ile Ala Thr Tyr Phe Cys Gln Gln His Trp Ser Tyr Pro Leu
                100                 105                 110
Thr Phe Gly Gln Gly Thr Lys Val Glu Val Lys Arg Thr Val Ala Ala
            115                 120                 125
Pro Ser Val Phe Ile Phe Pro Pro Ser Asp Glu Gln Leu Lys Ser Gly
    130                 135                 140
Thr Ala Ser Val Val Cys Leu Leu Asn Asn Phe Tyr Pro Arg Glu Ala
145                 150                 155                 160
Lys Val Gln Trp Lys Val Asp Asn Ala Leu Gln Ser Gly Asn Ser Gln
                165                 170                 175
Glu Ser Val Thr Glu Gln Asp Ser Lys Asp Ser Thr Tyr Ser Leu Ser
            180                 185                 190
Ser Thr Leu Thr Leu Ser Lys Ala Asp Tyr Glu Lys His Lys Val Tyr
    195                 200                 205
Ala Cys Glu Val Thr His Gln Gly Leu Ser Ser Pro Val Thr Lys Ser
210                 215                 220
Phe Asn Arg Gly Glu Cys Thr Ser Gly Gly Gly Ser Gly Gly Gly
225                 230                 235                 240
Gly Ser Gly Gly Gly Gly Ser His Val Gln Leu Val Glu Ser Gly Gly
                245                 250                 255
Gly Leu Val Gln Pro Gly Gly Ser Leu Arg Leu Ser Cys Ala Ala Ser
            260                 265                 270
Gly Phe Ser Leu Thr Asp Tyr Gly Val His Trp Val Arg Gln Ala Pro
    275                 280                 285
Gly Lys Gly Leu Glu Trp Leu Gly Val Ile Trp Ser Gly Gly Gly Thr
290                 295                 300
Ala Tyr Asn Thr Ala Leu Ile Ser Arg Phe Thr Ile Ser Arg Asp Asn
305                 310                 315                 320
```

```
Ser Lys Asn Thr Leu Tyr Leu Gln Met Asn Ser Leu Arg Ala Glu Asp
            325                 330                 335

Thr Ala Val Tyr Tyr Cys Ala Arg Arg Gly Ser Tyr Pro Tyr Asn Tyr
        340                 345                 350

Phe Asp Ala Trp Gly Cys Gly Thr Leu Val Thr Val Ser Ser Gly Gly
    355                 360                 365

Gly Gly Ser Gly Gly Gly Ser Gly Gly Gly Ser Gln Ala Val
370                 375                 380

Val Thr Gln Glu Pro Ser Leu Thr Val Ser Pro Gly Gly Thr Val Thr
385                 390                 395                 400

Leu Thr Cys Gly Ser Ser Thr Gly Ala Val Thr Ala Ser Asn Tyr Ala
            405                 410                 415

Asn Trp Val Gln Gln Lys Pro Gly Gln Cys Pro Arg Gly Leu Ile Gly
        420                 425                 430

Gly His Asn Asn Arg Pro Pro Gly Val Pro Ala Arg Phe Ser Gly Ser
    435                 440                 445

Leu Leu Gly Gly Lys Ala Ala Leu Thr Leu Leu Gly Ala Gln Pro Glu
450                 455                 460

Asp Glu Ala Glu Tyr Tyr Cys Ala Leu Trp Tyr Ser Asp His Trp Val
465                 470                 475                 480

Ile Gly Gly Gly Thr Lys Leu Thr Val Leu Gly
            485                 490

<210> SEQ ID NO 4
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Trp Ser Cys Ile Ile Leu Phe Leu Val Ala Thr Ala Thr Gly
1               5                   10                  15

Asp Ile Gln Met Thr Gln Ser Pro Ser Ser Leu Ser Val Ser Val Gly
            20                  25                  30

Asp Arg Val Thr Ile Thr Cys Lys Ala Ser Gln Asn Val Arg Thr Val
        35                  40                  45

Val Ala Trp Tyr Gln Gln Lys Pro Gly Leu Ala Pro Lys Thr Leu Ile
    50                  55                  60

Tyr Leu Ala Ser Asn Arg His Thr Gly Val Pro Ser Arg Phe Ser Gly
65                  70                  75                  80

Ser Gly Ser Gly Thr Asp Phe Thr Phe Thr Ile Ser Ser Leu Gln Pro
                85                  90                  95

Glu Asp Ile Ala Thr Tyr Phe Cys Gln Gln His Trp Ser Tyr Pro Leu
            100                 105                 110

Thr Phe Gly Gln Gly Thr Lys Val Glu Val Lys Arg Thr Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190
```

```
Ser Thr Leu Thr Leu Ser Lys Ala Asp Tyr Glu Lys His Lys Val Tyr
            195                 200                 205

Ala Cys Glu Val Thr His Gln Gly Leu Ser Ser Pro Val Thr Lys Ser
        210                 215                 220

Phe Asn Arg Gly Glu Cys Thr Ser Gly Gly Gly Ser Gly Gly Gly
225                 230                 235                 240

Gly Ser Gly Gly Gly Ser His Val Gln Leu Val Glu Ser Gly Gly
                245                 250                 255

Gly Leu Val Gln Pro Gly Gly Ser Leu Arg Leu Ser Cys Ala Ala Ser
            260                 265                 270

Gly Phe Ser Leu Thr Asp Tyr Gly Val His Trp Val Arg Gln Ala Pro
        275                 280                 285

Gly Lys Gly Leu Glu Trp Leu Gly Val Ile Trp Ser Gly Gly Thr
    290                 295                 300

Ala Tyr Asn Thr Ala Leu Ile Ser Arg Phe Thr Ile Ser Arg Asp Asn
305                 310                 315                 320

Ser Lys Asn Thr Leu Tyr Leu Gln Met Asn Ser Leu Arg Ala Glu Asp
                325                 330                 335

Thr Ala Val Tyr Tyr Cys Ala Arg Arg Gly Ser Tyr Pro Tyr Asn Tyr
            340                 345                 350

Phe Asp Ala Trp Gly Cys Gly Thr Leu Val Thr Val Ser Ser Gly Gly
        355                 360                 365

Gly Gly Ser Gly Gly Gly Gly Ser Gly Gly Gly Gly Ser Gly Gly Gly
    370                 375                 380

Gly Ser Gly Gly Gly Gly Ser Gly Gly Gly Gly Ser Gln Ala Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ala Ser Asn Tyr Ala Asn
            420                 425                 430

Trp Val Gln Gln Lys Pro Gly Gln Cys Pro Arg Gly Leu Ile Gly Gly
        435                 440                 445

His Asn Asn Arg Pro Pro Gly Val Pro Ala Arg Phe Ser Gly Ser Leu
    450                 455                 460

Leu Gly Gly Lys Ala Ala Leu Thr Leu Leu Gly Ala Gln Pro Glu Asp
465                 470                 475                 480

Glu Ala Glu Tyr Tyr Cys Ala Leu Trp Tyr Ser Asp His Trp Val Ile
                485                 490                 495

Gly Gly Gly Thr Lys Leu Thr Val Leu Gly
            500                 505

<210> SEQ ID NO 5
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgggctggt cctgcatcat cctgtttctg gtggctaccg ccaccggcga ggtgcagctg      60
ctggaatctg gcggaggact ggtgcagcct ggcggctctc tgagactgtc ttgtgccgcc     120
tctggcttcg ccttctccac ctacgacatg tcctgggtgc acaggctcc tgcaagggc      180 ctggaatggg tggccacaat ctcttccggc ggctcctaca cctactacct ggactctgtg     240
```

```
aagggccggt tcaccatctc ccgggactcc tccaagaaca ccctgtacct gcagatgaac      300
tccctgcagg ccgaggactc cgccatctac tactgtgccc ctaccaccgt ggtgcccttc      360
gcttattggg gccagggcac cctcgtgacc gtgtcctctg cttctaccaa gggcccatcg      420
gtcttccccc tggcaccctc ctccaagagc acctctgggg gcacagcggc cctgggctgc      480
ctggtcaagg actacttccc cgaaccggtg acggtgtcgt ggaactcagg cgccctgacc      540
agcggcgtgc acaccttccc ggccgtccta cagtcctcag gactctactc cctcagcagc      600
gtggtgaccg tgccctccag cagcttgggc acccagacct acatctgcaa cgtgaatcac      660
aagcccagca acaccaaggt ggacaagaga gttgagccca aatcttgtga caaaactcac      720
acatgcccac cgtgcccagc acctgaactc ctggggggac cgtcagtctt cctcttcccc      780
ccaaaaccca aggacaccct catgatctcc cggacccctg aggtcacatg cgtggtggtg      840
gacgtgagcc acgaagaccc tgaggtcaag ttcaactggt acgtggacgg cgtggaggtg      900
cataatgcca agacaaagcc gcgggaggag cagtacgcca gcacgtaccg tgtggtcagc      960
gtcctcaccg tcctgcacca ggactggctg aatggcaagg agtacaagtg caaggtctcc     1020
aacaaagccc tcccagcccc catcgagaaa accatctcca aagccaaagg gcagccccga     1080
gaaccacagg tgtacaccct gcccccatcc cgggatgagc tgaccaagaa ccaggtcagc     1140
ctgacctgcc tggtcaaagg cttctatccc agcgacatcg ccgtggagtg ggagagcaat     1200
gggcagccgg agaacaacta caagaccacg cctcccgtgc tggactccga cggctccttc     1260
ttcctctaca gcaagctcac cgtggacaag agcaggtggc agcaggggaa cgtcttctca     1320
tgctccgtga tgcatgaggc tctgcacaac cactacacgc agaagagcct ctccctgtct     1380
ccgggtaaat ga                                                        1392

<210> SEQ ID NO 6
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Gly Trp Ser Cys Ile Ile Leu Phe Leu Val Ala Thr Ala Thr Gly
1               5                   10                  15

Glu Val Gln Leu Leu Glu Ser Gly Gly Gly Leu Val Gln Pro Gly Gly
            20                  25                  30

Ser Leu Arg Leu Ser Cys Ala Ala Ser Gly Phe Ala Phe Ser Thr Tyr
        35                  40                  45

Asp Met Ser Trp Val Arg Gln Ala Pro Gly Lys Gly Leu Glu Trp Val
    50                  55                  60

Ala Thr Ile Ser Ser Gly Gly Ser Tyr Thr Tyr Tyr Leu Asp Ser Val
65                  70                  75                  80

Lys Gly Arg Phe Thr Ile Ser Arg Asp Ser Ser Lys Asn Thr Leu Tyr
                85                  90                  95

Leu Gln Met Asn Ser Leu Gln Ala Glu Asp Ser Ala Ile Tyr Tyr Cys
            100                 105                 110

Ala Pro Thr Thr Val Val Pro Phe Ala Tyr Trp Gly Gln Gly Thr Leu
        115                 120                 125

Val Thr Val Ser Ser Ala Ser Thr Lys Gly Pro Ser Val Phe Pro Leu
    130                 135                 140
```

```
Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
            165                 170                 175

Gly Ala Leu Thr Ser Gly Val His Thr Phe Pro Ala Val Leu Gln Ser
        180                 185                 190

Ser Gly Leu Tyr Ser Leu Ser Ser Val Val Thr Val Pro Ser Ser Ser
    195                 200                 205

Leu Gly Thr Gln Thr Tyr Ile Cys Asn Val Asn His Lys Pro Ser Asn
210                 215                 220

Thr Lys Val Asp Lys Arg Val Glu Pro Lys Ser Cys Asp Lys Thr His
225                 230                 235                 240

Thr Cys Pro Pro Cys Pro Ala Pro Glu Leu Leu Gly Gly Pro Ser Val
            245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
290                 295                 300

Thr Lys Pro Arg Glu Glu Gln Tyr Ala Ser Thr Tyr Arg Val Val Ser
305                 310                 315                 320

Val Leu Thr Val Leu His Gln Asp Trp Leu Asn Gly Lys Glu Tyr Lys
            325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
450                 455                 460

<210> SEQ ID NO 7
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Trp Ser Cys Ile Ile Leu Phe Leu Val Ala Thr Ala Thr Gly
1               5                   10                  15

Glu Val Gln Leu Leu Glu Ser Gly Gly Gly Leu Val Gln Pro Gly Gly
            20                  25                  30

Ser Leu Arg Leu Ser Cys Ala Ala Ser Gly Phe Ala Phe Ser Thr Tyr
        35                  40                  45
```

```
Asp Met Ser Trp Val Arg Gln Ala Pro Gly Lys Gly Leu Glu Trp Val
 50                  55                  60

Ala Thr Ile Ser Ser Gly Gly Ser Tyr Thr Tyr Tyr Leu Asp Ser Val
 65                  70                  75                  80

Lys Gly Arg Phe Thr Ile Ser Arg Asp Ser Ser Lys Asn Thr Leu Tyr
                 85                  90                  95

Leu Gln Met Asn Ser Leu Gln Ala Glu Asp Ser Ala Ile Tyr Tyr Cys
            100                 105                 110

Ala Pro Thr Thr Val Val Pro Phe Ala Tyr Trp Gly Gln Gly Thr Leu
            115                 120                 125

Val Thr Val Ser Ser Ala Ser Thr Lys Gly Pro Ser Val Phe Pro Leu
130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
210                 215                 220

Thr Lys Val Asp Lys Arg Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
290                 295                 300

Thr Lys Pro Arg Glu Glu Gln Tyr Ala Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Ala Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
450                 455                 460
```

```
<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```